(12) United States Patent
Yang

(10) Patent No.: US 7,655,778 B2
(45) Date of Patent: Feb. 2, 2010

(54) SISP-1, A NOVEL P53 TARGET GENE AND USE THEREOF

(75) Inventor: Yoon-Sun Yang, Seoul (KR)

(73) Assignee: Curonix Co., Ltd., Seoul (KR)

( * ) Notice: Subject to any disclaimer, the term of this patent is extended or adjusted under 35 U.S.C. 154(b) by 18 days.

(21) Appl. No.: 11/679,803

(22) Filed: Feb. 27, 2007

(65) Prior Publication Data

US 2007/0237745 A1    Oct. 11, 2007

Related U.S. Application Data

(60) Provisional application No. 60/767,047, filed on Feb. 28, 2006.

(51) Int. Cl.
*C07H 21/02* (2006.01)
*C12N 15/00* (2006.01)
*C12N 5/00* (2006.01)

(52) U.S. Cl. .................... 536/23.1; 435/320.1; 435/325

(58) Field of Classification Search ................ 536/23.1; 435/320.1, 325
See application file for complete search history.

(56) References Cited

U.S. PATENT DOCUMENTS 6,953,799 B1    10/2005   Henry et al.
2003/0083482 A1  5/2003   Murphy

FOREIGN PATENT DOCUMENTS

WO    WO 00 12708 A       3/2000
WO    WO 2005031001  *    4/2005

OTHER PUBLICATIONS

Kennell, Principles and practices of nucleic acid hybridization. Progr. Nucleic Acid Res. Mol. Biol. 11: 259-301, 1971.*
Kato et al., Understanding the function—structure and function—mutation relationships of p53 tumor suppressor protein by high-resolution missense mutation analysis PNAS Jul. 8, 2003 vol. 100 No. 14 8424-8429.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-495.*
Wiley and Sons, Biochemistry 1990, p. 126-128.*
Kimchi-Sarfaty C et al., A "silent" polymorphism in the MDR1 gene changes substrate specificity.Science. Jan. 2007 26;315(5811):525-8.*
Fadeel, B., et al., "Apoptosis in Human Disease: A New Skin for the Old Ceremony?" Biochem Biophys Res. Commun., 266(3), 699-717 (1999).
Vogelstein, B. et al., "Surfing the p53 network," Nature 408, 307-310 (2000).
Velculescu, V.E., et al., "Biological and clinical importance of the p53 tumor suppressor gene," Clinical Chemistry 42:6, 858-868 (1996).
Levine, A.J., et al., "p53, the Cellular Gatekeeper for Growth and Division," Cell 88(3), 323-331 (1997).
Ko, L.J., "p53: puzzle and paradigm," Genes Dev. 10, 1054-1072 (1996).
Harms, K. et al "The common and distinct target genes of the p53 family transcription factors," Cell. Mol. Life Sci., 61 822-842 (2004).
Fesik, S.W., "Promoting Apoptosis As A Strategy For Cancer Drug Discovery," Nature, 5, 876-885, (Nov. 2005).
Wan, D., et al., "Large-scale cDNA transfection screening for genes related to cancer development and progression," Proc. Nat'l Acad. Sci. USA, 101 (44), 15724-15729 (2004).
Clark, H.F., et al., "The Secreted Protein Discovery Initiative (SPDI), a Large-Scale Effort to Identify Novel Human Secreted and Transmembrane Proteins: A Bioinformatics Assessment," Genome Res. 13, 2265-2270 (2003).
Prives, C., et al., Abstract of "The p53 pathway," J. Pathology, 187(1), 112-126 (1999).
Oren, M., "Regulation of the p53 Tumor Suppressor Protein," J. of Biological Chemistry, 276(51), 36031-36034 (1999).
Fortin, A., "The proapoptotic gene SIVA is a direct transcriptional target for the Tumor Suppressors p53 and E2F1," J. Bio. Chem., 279 (27), 28706-28714 (2004).
Sax, J.K., et al., "Identification and Characterization of the Cytoplasmic Protein TRAF4 as a p53-regulated Proapoptotic Gene," J. of Bio. Chem., 278 (38), 36435-36444 (2003).
Friedman, Paula N. et al., "The p53 protein is an unusually shaped tetramer that binds directly to DNA," Proc. Natl. Acad. Sci. USA, vol. 90, pp. 3319-3323, Apr. 1993.
Bian, J. et al, "p53CP, a putative p53 competing protein that specifically binds to the consensus p53 DNA binding sites: A third member of the p53 family?" Proc. Natl. Acad. Sci. USA vol. 94, pp. 14753-14758, Dec. 1997.
Wan, D., et al., "Large-scale cDNA transfection screening for genes related to cancer development and progression," PNAS, 101:44, Nov. 2, 2004, pp. 15724-15729.
NCBI GenBank AY265805.1.

* cited by examiner

*Primary Examiner*—Maria Leavitt
(74) *Attorney, Agent, or Firm*—Sughrue Mion, PLLC

(57) ABSTRACT

The present invention relates to a novel p53 target gene SISP-1 (Stress induced Secreted Protein 1) and a SISP-1 protein encoded by the gene. The SISP-1 protein of the present invention induces apoptosis by interaction with p53. The present invention provides the use of the gene/protein associated with treating abnormal apoptosis such as tumor.

5 Claims, 24 Drawing Sheets

FIG. 1 cDNA sequence:

```
gcgtcccgcc cgctccccgg caccagaagt tcctctgcgc gtccgacggc
gacatgggcg tccccacggc cctggaggcc ggcagctggc gctggggatc
cctgctcttc gctctcttcc tggctgcgtc cctaggtccg gtggcagcct
tcaaggtcgc cacgccgtat tccctgtatg tctgtcccga ggggcagaac
gtcaccctca cctgcaggct cttgggccct gtggacaaag ggcacgatgt
gaccttctac aagacgtggt accgcagctc gagggcgag gtgcagacct
gctcagagcg ccggcccatc cgcaacctca cgttccagga ccttcacctg
caccatggag gccaccaggc tgccaacacc agccacgacc tggctcagcg
ccacgggctg gagtcggcct ccgaccacca tgcaacttc tccatcacca
tgcgcaacct gaccctgctg gatagcggcc tctactgctg cctggtggtg
gagatcaggc accaccactc ggagcacagg gtccatggtg ccatggagct
gcaggtgcag acaggcaaag atgcaccatc caactgtgtg gtgtacccat
cctcctccca ggagagtgaa aacatcacgg ctgcagccct ggctacgggt
gcctgcatcg taggaatcct ctgcctcccc ctcatcctgc tcctggtcta
caagcaaagg caggcagcct ccaaccgccg tgcccaggag ctggtgcgga
tggacagcaa cattcaaggg attgaaaacc ccggctttga agcctcacca
cctgcccagg ggatacccga ggccaaagtc aggcaccccc tgtcctatgt
ggcccagcgg cagccttctg agtctgggcg gcatctgctt tcggagccca
gcaccccct gtctcctcca ggccccggag acgtcttctt cccatccctg
gaccctgtcc ctgactctcc aaactttgag gtcatctagc ccagctgggg
gacagtgggc tgttgtggct gggtctgggg caggtgcatt tgagccaggg
ctggctctgt gagtggcctc cttggcctcg gccctggttc cctccctcct
gctctgggct cagatactgt gacatcccag aagcccagcc cctcaacccc
tctggatgct acatggggat gctggacggc tcagcccctg ttccaaggat
tttggggtgc tgagattctc ccctagagac ctgaaattca ccagctacag
atgccaaatg acttacatct taagaagtct cagaacgtcc agcccttcag
cagctctcgt tctgagacat gagccttggg atgtggcagc atcagtggga
caagatggac actgggccac cctcccaggc accagacaca gggcacggtg
gagagacttc tccccgtgg ccgccttggc tccccgtttt gcccgaggc
tgctcttctg tcagacttcc tctttgtacc acagtggctc tggggccagg
cctgcctgcc cactggccat cgccaccttA cccagctgcc tcctaccagc
agtttctctg aagatctgtc aacaggttaa gtcaatctgg ggcttccact
gcctgcattc cagtccccag agcttggtgg tcccgaaacg ggaagtacat
attggggcat ggtggcctcc gtgagcaaat ggtgtcttgg gcaatctgag
gccaggacag atgttgcccc acccactgga gatggtgctg agggaggtgg
gtggggcctt ctgggaaggt gagtggagag gggcacctgc ccccgccct
ccccatcccc tactcccact gctcagcgcg ggccattgca agggtgccac
acaatgtctt gtccaccctg ggacacttct gagtatgaag cgggatgcta
ttaaaaacta catggggaaa caggtgcaaa aaaaaaaaaa aaaaaaaaa
```

MGVPTALEAGSWRWGSLLFALFLAASLGPVAAFKVATPYSLYVCPEGQNV
TLTCRLLGPVDKGHDVTFYKTWYRSSRGEVQTCSERRPIRNLTFQDLHLH
HGGHQAANTSHDLAQRHGLESASDHHGNFSITMRNLTLLDSGLYCCLVVE
IRHHHSEHRVHGAMELQVQTGKDAPSNCVVYPSSSQDSENITAAALATGA
CIVGILCLPLILLLVYKQRQAASNRRAQELVRMDSNIQGIENPGFEASPP
AQGIPEAKVRHPLSYVAQRQPSESGRHLLSEPSTPLSPPGPGDVFFPSLD
PVPDSPNFEVI$^{311}$

B

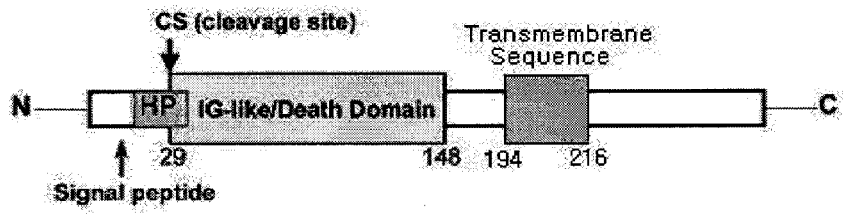

FIG. 3

P53 binding site in SISP-1 Promoter

AAACTGGCTCCAGCTTGCCTA
475bp upstream from the transcription
start site (C, G required nucleotides bolded)

FIG. 5
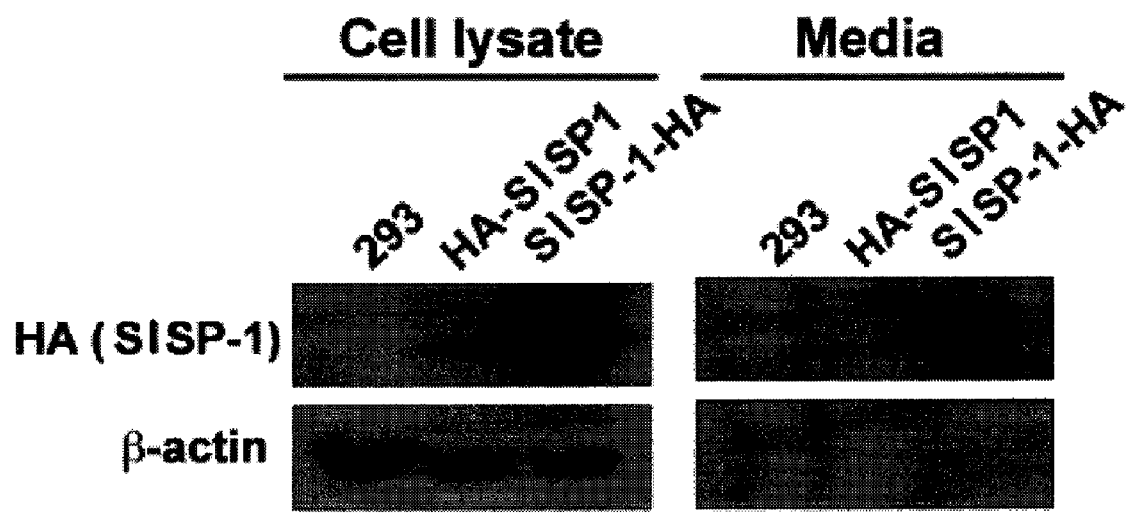
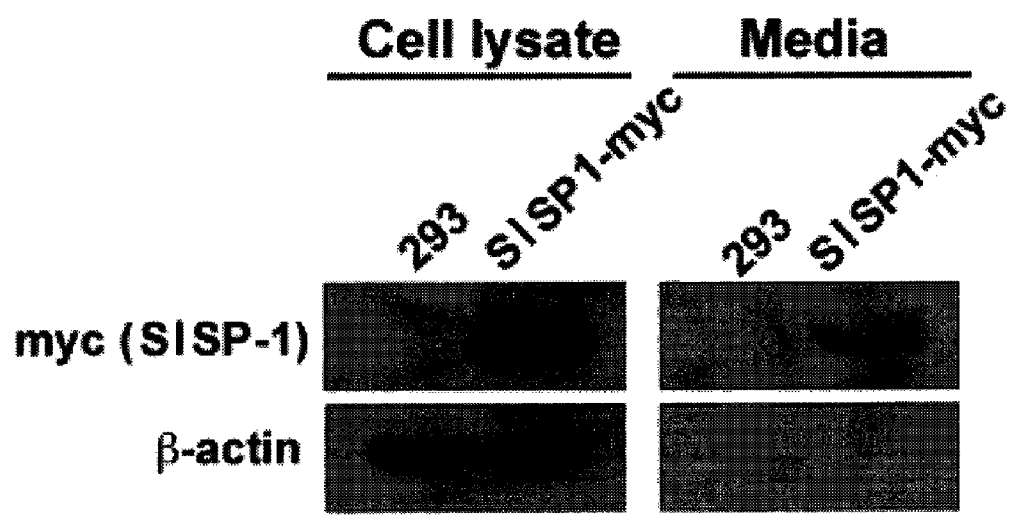

FIG. 12
SISP1 expression in normal human tissues and cells
A. DD1 expression in human tissues
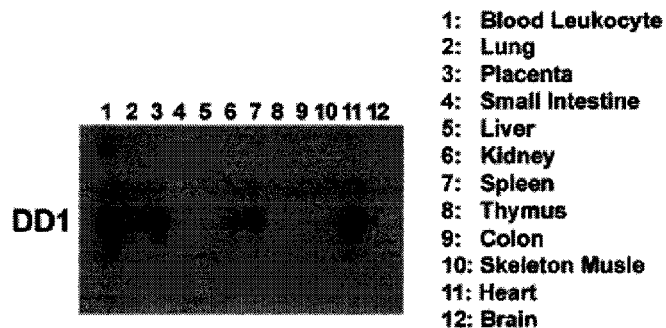
1: Blood Leukocyte
2: Lung
3: Placenta
4: Small Intestine
5: Liver
6: Kidney
7: Spleen
8: Thymus
9: Colon
10: Skeleton Musle
11: Heart
12: Brain
B. DD1 expression in human normal and tumor epithelial cells
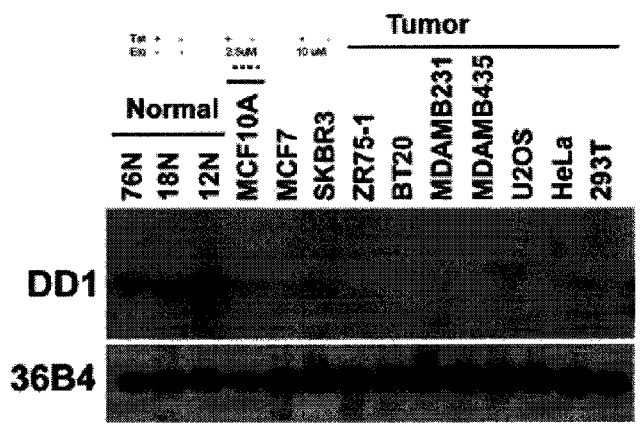

FIG. 13

SISP-1 Genomic Sequence (1/8)

```
   1 ggggcgggt gcctggagca cggcgctggg gccgcccgca gcgctcactc gctcgcactc
  61 agtcgcggga ggcttccccg cgccggccgc gtcccgcccg ctccccggca ccagaagttc
 121 ctctgcgcgt ccgacggcga catgggcgtc cccacggccc tggaggccgg cagctggcgc
 181 tggggatccc tgctcttcgc tctcttcctg gctgcgtccc taggtccggt ggcagccttc
 241 aaggtcgcca cgccgtattc cctgtatgtc tgtcccgagg ggcagaacgt caccctcacc
 301 tgcaggctct tgggccctgt ggacaaaggg cacgatgtga ccttctacaa gacgtggtac
 361 cgcagctcga ggggcgaggt gcagacctgc tcagagcgcc ggcccatccg caacctcacg
 421 ttccaggacc ttcacctgca ccatggaggc caccaggctg ccaacaccag ccacgacctg
 481 gctcagcgcc acgggctgga gtcggcctcc gaccaccatg gcaacttctc catcaccatg
 541 cgcaacctga ccctgctgga tagcggcctc tactgctgcc tggtggtgga gatcaggcac
 601 caccactcgg agcacagggt ccatggtgcc atggagctgc aggtgcagac aggcaaagat
 661 gcaccatcca actgtgtggt gtacccatcc tcctcccagg atagtgaaaa catcacggct
 721 gcagccctgg ctacgggtgc ctgcatcgta ggaatcctct gcctcccct catcctgctc
 781 ctggtctaca agcaaaggca ggcagcctcc aaccgccgtg cccaggagct ggtgcggatg
 841 gacagcaaca ttcaagggat tgaaaaaccc ggcttttgaag cctcaccacc tgcccagggg
 901 atacccgagg ccaaagtcag gcacccctg tcctatgtgg cccagcggca gccttctgag
 961 tctgggcggc atctgctttc ggagcccagc accccctgt ctcctccagg cccggagac
1021 gtcttcttcc catccctgga ccctgtccct gactctccaa actttgaggt catctagccc
1081 agctggggga cagtgggctg ttgtggctgg gtctgggca ggtgcatttg agccagggct
1141 ggctctgtga gtggcctcct tggcctcggc cctggttccc tccctcctgc tctgggctca
1201 gatactgtga catcccagaa gcccagcccc tcaaccctc tggatgctac atggggatgc
1261 tggacggctc agccctgtt ccaaggattt tggggtgctg agattctccc ctagagacct
1321 gaaattcacc agctacagat gccaaatgac ttacatctta agaagtctca gaacgtccag
1381 cccttcagca gctctcgttc tgagacatga gccttgggat gtggcagcat cagtgggaca
1441 agatggacac tgggccaccc tcccaggcac cagacacagg gcacggtgga gagacttctc
1501 ccccgtggcc gccttggctc ccccgttttg cccgaggctg ctcttctgtc agacttcctc
1561 tttgtaccac agtggctctg gggccaggcc tgcctgccca ctggccatcg ccaccttccc
1621 cagctgcctc ctaccagcag tttctctgaa gatctgtcaa caggttaagt caatctgggg
1681 cttccactgc ctgcattcca gtccccagag cttggtggtc ccgaaacggg aagtacatat
1741 tggggcatgg tggcctccgt gagcaaatgg tgtcttgggc aatctgaggc caggacagat
1801 gttgccccac ccactggaga tggtgctgag ggaggtgggt ggggccttct gggaaggtga
1861 gtggagaggg gcacctgccc cccgccctcc ccatccccta ctcccactgc tcagcgcggg
1921 ccattgcaag ggtgccacac aatgtcttgt ccaccctggg acacttctga gtatgaagcg
1981 ggatgctatt aaaaactaca tggggaaaca ggtgcaaacc ctggagatgg attgtaagag
2041 ccagtttaaa tctgcactct gctgctcctc ccccacccc accttccact ccatacaatc
2101 tgggcctggt ggagtcttcg cttcagagcc attcggccag gtgcgggtga tgttcccatc
2161 tcctgcttgt gggcatgccc tggctttgtt tttatacaca taggcaaggt gagtcctctg
2221 tggaattgtg attgaaggat tttaaagcag gggaggagag taggggcat ctctgtacac
2281 tctggggta aacagggaa ggcagtgcct gagcatgggg acaggtgagg tggggctggg
2341 cagaccccct gtagcgttta gcaggatggg ggcccaggt actgtggaga gcatagtcca
2401 gcctggcat ttgtctccta gcagcctaca ctggctctgc tgagctgggc ctgggtgctg
2461 aaagccagga tttggggcta ggcgggaaga tgttcgccca attgcttggg ggttggggg
2521 gatgaaaag gggagcacct ctaggctgcc tggcagcagt gagccctggg cctgtggcta
2581 cagccaggga accccacctg gacacatggc cctgcttcta agcccccag ttaggcccaa
2641 aggaatggtc cactgagggc ctcctgctct gcctgggctg ggccagggc tttgaggaga
2701 gggtaaacat aggcccggag atgggctga cacctcgagt ggccagaata tgcccaaacc
2761 ccggcttctc ccttgtccct aggcagaggg gggtcccttc ttttgttccc tctggtcacc
2821 acaatgcttg atgccagctg ccataggaag agggtgctgg ctggccatgg tggcacacac
2881 ctgtcctccc agcactttgc agggctgagg tggaaggacc gcttaagccc aggtgttcaa
2941 ggctgctgtg agctgtgttc gagccactac actccagcct ggggacggag caaaactttg
3001 cctcaaaaca aattttaaaa agaaagaaag aaggaaagag ggtatgtttt tcacaattca
3061 tgggggcctg catggcagga gtggggacag gacacctgct gttcctggag tcgaaggaca
3121 agcccacagc ccagattccg gttctcccaa ctcaggaaga gcatgccctg ccctctgggg
3181 aggctggcct ggccccagcc ctcagctgct gaccttgagg cagagacaac ttctaagaat
3241 ttggctgcca gaccccaggc ctggctgctg ctgtgtggag agggaggcgg cccgcagcag
3301 aacagccacc gcacttcctc ctcagcttcc tctggtgcgg ccctgccctc tcttctctgg
3361 acccttttac aactgaacgc atctggggctt cgtggtttcc tgttttcagc gaaatttact
```

FIG. 14

SISP-1 Genomic Sequence (2/8)

```
3421 ctctacaggg cctaatggag tgcccagggc ctgggaaggc attggtgagc ttcactggga
3481 ctagattctc caaagcctgg agtatgaagg gtgcatgggc tgcgtccagc tacctgtgag
3541 cccctgtagg ccctcacagt ctgaaatgcc catggaggtg cctacaggtt ctcttcttaa
3601 agttgtcagg agatggggac attgcaactt gaaggcaagc ctggccctgg gtttgcttat
3661 cttggtggat ctttcttaca tctgatcttt ttacattcgg tccattcact ttggctggcc
3721 atcaccaaag acaaagacag tggccaccat ctttctcatc agtaatccaa taatgaggtt
3781 gctctgctac ttaccaagcc aagcaagccc attcctttag cctttctgcg taggatctta
3841 tttcccatgg ggacctgggg tcaaaccctg cctctgctgt tcactcatca tgggaacaca
3901 aacacacact tcccctttgt ctgtgcaatg gacaggttgg gtgacgtggt ctcagtgagg
3961 ctgaccaccc tcctctgaag gttaattcca tgatggtgtt tccctagctt cagtcatttg
4021 cttatcacct ttgtgatctc tgcagtgtct gcctttcata atatttactt atttttttct
4081 ttaaatctac tcattctttt atttgagtat gtagatcttt aaaaggaaac tttttatcgc
4141 tgtcattagt ggaaagccag tatcacttgt cataaataga acaaaaccat aaaagaacgt
4201 aacaggaaaa ccatataagg gtattgaatt ctagttggaa actttagcct gggaaggctc
4261 ggagtctgaa aactgctgct ttcccttgca aaaattaaa ataaaataaa atttaaaaag
4321 aaaaggagat tagcaagtga gagaaagatg tttagagac atattagcat caaactgaga
4381 cttctctctt gatgtaatca ggactgaaat aattgtaaag ggataacct cttctatata
4441 tgattcaatg ttatttaatg taaaaccaaa agtaaaacta tgtggtagac gtggccaggc
4501 aagctgggct ttcattggtc atgacatttg tccgtcttca agaaggaggt ggggcctcca
4561 gtcagtcccc agctacctct attctctaga gagtagtcag atggcaccag acctccagag
4621 gctgactacc tgggttcaga tcctgacacc atcacttatt agttgtgagg ctgtgggcaa
4681 gatactaatc tctctgtgct tccgttttct catctgtaaa atggagatga tactagtacc
4741 tacctcatag ggtggaagga ttacataaac taatctatgt aaaagtgttt agaatgaggc
4801 cgagcacagt ggctcatgcc tgtaatccca gcactttggg aggctgaggt ggaggatct
4861 cttgaagcca ggagtttcaa gccaggggac cagcctggac aacataacga gaccccatca
4921 ctacgaaaaa tttaaaaatt agctgggcat agtggcatgt gtctgtagtc ctagttggga
4981 ggcaggggtg ggaggataac ttgagcccat gagttcgagg ttacagtggg ctatgatctc
5041 attgtcactg cattccagcc tgagtgaaga gcaagaccct agctcactaa agaaaaccaa
5101 ccaaacggcc aggcacagtg gctcactcct gtaatccag cacttgggga ggacgaggcg
5161 ggtggatcac atgaggtcag gagttcaaga ccagcctggc caacgtggtg aaaccccgtc
5221 tctactaaaa atacaaaaat tagccaggcg tggtggcggg tgcctgtagt cccagctact
5281 cgggaggctg aggcaggaga gttgcttcaa cctgggaggc ggaggttgca gtgagctgag
5341 attgcaccac tgaactccag cctgggcaac agagcgagac tccatctcaa acaacaacaa
5401 caacaacaac agcaacaaag ccaaccaaac aaacaagcac ttagaatgat gcctggcaca
5461 gagtagtagg gggcaaaaag acttgagctg gaccctgagg acgtcttcac agcatagaag
5521 cgtgagggtg gctggctgga gccgggagcc tgagctgcac acagtcctcc tccaaaaggg
5581 cctgggagt ctgggagggg ttcatccaca gaagcatcca cgggccggga cctctggcca
5641 gctgcctagg ccctccccgg ggaggcatgc tagcctccag ctccagcccc ggatgcacgg
5701 aggctttccc aaggtgctgg aagtgccgct tccttcaata gagcctggct tccccttccc
5761 agcccccttg gtctgatgtg aatggacact tcctgcgggg gcaggtatca ataaacacat
5821 ctgagatgcc ctttgtcctc actggccaga aagccccagg gcagacttgc tggcttcagg
5881 ccctgagcct atgccttgtg acgcttcctt tcttagcctt ggcagcccca gtcctgattg
5941 atccatgcct ctgtttccct ctgcatcttg ataaagacag aacatagtct tttcctacag
6001 ccccagcccc agcctgctgga ccatcctggg ggatggggcc tggcggggag ctggaaccag
6061 gtcccattct ctttgggatg tcctgtgaga ccaaggacgg gacctttgc atctagtgca
6121 gggccagcca cagcaggcaa ttaataactg tttacttgac aacctctagc agctggtcag
6181 agttcagctg tttgggtggg gcttcctagg cccgactaac caagcttggg tcccacctcc
6241 aaaggctagg gcgttgcctt ggcgactgtg ggctaagctc acgccccgtc atgaaaaata
6301 cacaggcctg tccacaccca cacacaccca tcccgtgcac actcacaggg gtcacccggg
6361 gcctgctggg tggagagagg tgaaggtcac aaaaactggc attctgagaa gatgccaaca
6421 agagctcctt tcccttgtac tgggacagaa acatctgagg gtgccacagc tagaaatctc
6481 aggcacaggt ccaggcccaa gttctgagca gatgcccctg atggaactct gcatccccac
6541 agcctccctg cctgggcctg gccatgttta ggaccttggt aaatatttgt ggaatgaaag
6601 aatgatgttt tcagcttggg tctgaggcag agcaggaatg ttgcacggag ggcgtggagg
6661 tcaatgcacg gtcagttcat ttttttctaaa tagctgaagg atgaggcatc agccccgcct
6721 gcccactgga gggttctgga gaggtggtg gctcttcctg tctgcagtgc tggcctgtcc
```

FIG. 15

SISP-1 Genomic Sequence (3/8)

```
 6781 aaggtgtgaa tctcagctca gtcacacagc gctgtgtggc cttgggcaag tcacttctct
 6841 gagtctgttt cctcatcttt aaaatgggga tgataccacc catgttgggg gtgttatgag
 6901 aactaaatgt gacaggtata agatgctcag caagagccta gcacataata catggtcata
 6961 agacagctct tccctcctgc ccacaggatt ttagagctgg cagccctcag gttaagatga
 7021 agaaacggag gctcagagaa gcgtgggatc tgcccaaggg cacacaatga gggcacaact
 7081 aagtggacac tgaggcccca ggacgttgca atccaagcga gagttttact cctgagactc
 7141 aggctttccc aggttcacgg cactcttcct ctaggtggcc ctgcctcctt acctggtggc
 7201 aggtggcggg tgcgggcgg ggggcctggg tcttgacagc agcacggcaa ctggacggtt
 7261 cccgcctggc acatgctcag gcccaggccc cgggtcattt tcctgtccca catgcttttg
 7321 gccaccctgg agccaggggc tttcctcccc acccacttt cccggtctcc gacaatgacc
 7381 caggtgtcca aaaggatctg ctcctgacaa taagcaacat cctctcgcca aagaattgta
 7441 attttagccg ggctgcacag cttccctgac aacacacagg catgtgcaca gatgtggagt
 7501 ccgcgggca cgtgcaggcc cctctgcgtg ctgtgcgctg ccctctccc ccatgccatg
 7561 ccttcgagtg tcctcctaac gacaggctgc tgtgggcctt gtcccagctg gagtctcaga
 7621 cacagtaaat ggggtgtttt ctggccttcc ctccctcccc aggacaaacc cctgtggacc
 7681 cttggtttgt cctgtccctc tggcttgtcc tggaccctct cctgtctggc ctcttgctt
 7741 gaaaactgaa catcctcccc tgctcccaa acttgaatcc taagacagct ttttctaaa
 7801 aggggaacaa ctcctttggg acctgtggga tgggtggcca gtgtgtgagg ggtggggagg
 7861 tgtggggat tgagcaatgc cccctctccc gtactccctg aactctgctt tctctctgat
 7921 gcacccaccc gccgtgcatc tcaaggaagt tgcctccagg ggagaacatc ccttccctac
 7981 tgctgcgggt gctatggta caatcctggg gtcattaacc ccattgctta gaccctgagg
 8041 gctcccagcc tggtgccctg ccccaccttg ttcacaggga cactcaggcc aacaaccacg
 8101 ctagccccac ttgtccacac ctctgtccac ttgagggccc caacccccac ccagctcagc
 8161 tttgcgcatc ttgctttggc tgccagctct actctgcctg ccctgccata ccctcctctg
 8221 gcctgcagcc ccgtgtctgc tgagccagcc ctttggccag cccccaaggt atgtgtgctg
 8281 gtggtaaata ctaccgtagc tgaagctgga gctgaattca gctcccagcc ctgggtggc
 8341 tctggggtag gaggtgatgt caggcaaagg gagaaagggg cagaagctgg gagaggtgct
 8401 ggtgggacct gccacatggc ctgctgggga aggggcagc acagggcccc cttggggcag
 8461 gttttgtttc ttcctgggag tacgtgggag agcccttcc ctaggtcctc ctcacttctg
 8521 tttcccggca gagccatagt tttgcagcta cacccaccc actcaggtgt gaaggggaag
 8581 tccaggccag cacggacaaa accagggca cagccaagct tcctgggcct ccttttccac
 8641 tgagcctgct gcaggggtaa gggcagtggg ttagcagagg agagttggct agtccctgca
 8701 ctgccaggct ttccctgggg acctgggtg gatcatctcc tctcttgagt ctgtgggtca
 8761 gatttgtagc ataatggtt tgggcagtag agtcccatgc cagctagccc aagaagccac
 8821 actcattcat cacaaactca aatgtccaca ggaccaagaa accacggtga gagagtgaag
 8881 caggccaggt ggaattatta gggagtagta cggacggact ctggcgaact ggagtgccgg
 8941 tgccccccaa aagctgctac tgagccccag ctgacagttg ccctgtggga aagctggttt
 9001 agcattatct tctgattttc taaggagagc tggaagtcag aatttttcatg tcaaattcct
 9061 ggttttttaaa tgttgccatc tcaagaaaat taaaaagatt ttgaggatcc aatgaaatat
 9121 gtgtgaaggc tggatgtggc ctgtgggctc ccagtttctg gccttttttt tcatcagtat
 9181 agtgtctatg tgtctgagtt taattctagc tctagcactt gcttgctgtg tgatcatcag
 9241 tgagttacgt aagttctctg tgccttagtt tcttcatcag tgcaatggga ataaaaacaa
 9301 taccttatgg cattgttaga tatgcccatg aaaaccttag cgtagtgcac aacacatgct
 9361 gtgtcttctt attacggttc tgcctagatc ctgcgttacc tgaagtcccc catgctccag
 9421 gctttgagat catacccctc ggaactttgg aacttcagtc caaccacttt ccctttctgg
 9481 gtctctgtgt ttctgcctga aaaggagacc tgtatcttgc caaagaagtt ctgaaatctc
 9541 tgctcaccct gacaatgact ccaaaaatct ggggctccca gacttggctc tctgcctaaa
 9601 actccactct tgcagacatg ccgtttgggg ctttggtgcc tttggagact ctcctttaaa
 9661 cacaagcgcc ccaggatcgg atcacaagtt gttatcagtc attcacacct tagcaggaaa
 9721 gactttaaag ctggcttctc catcccactg tgcttctcac tcctaggagg cacttcttga
 9781 cttgctgaat gaattagaga cctgtctagc tcccaagtac aagcgccga ctactcgcat
 9841 ggcacttaca gaacacttca tgtgaattat tactaaccgt tgcctcaact ctgccaggga
 9901 gatgttttca tttctgggaa aaacatctgt gagtgaggag tcgggctca gcgtctaagt
 9961 ggctcacagc tactggtcca gtacaggctg ccagctcca gaagccccac caggctgcct
10021 ccctcctggc tgggcaaggc tttcagctct tccagtgggt cccagcctgc cgccgagggt
10081 cctgggctct aagggcaggg aaggggcatc tgaaggagga tgtggcatta tattggttct
10141 gggcaatgcc cctggctggg gcaatgaaaa ggatgtatca gtttggattc tgtacatagt
```

FIG. 16

```
SISP-1 Genomic Sequence (4/8)

10201 tctaaccctc cttccctctc tgctagaccc acaacagcct gacatgccat ttaaaataaa
10261 aataccactg gccgggcgta gtgggtcaca cttgtaatcc caagactttg agaggccaag
10321 gcaggagaat tgcttgaagc caggagttca aggtcagcct gggcaacaga gggagactcc
10381 gtctcaaaaa caaataaata aataaaata acaccaacgc ataataatta tagctatccc
10441 tcagatgtct gcagagggca ttagagctca catcttgtgt tctcatcttt ccctcatcta
10501 gtcctttgc aaccctgcat tgtagccaat agttttctca ctgcacagag gaggaaactg
10561 aggctcatac agttagatag aaacgcggcc tctatccaat attctgtttt caaaagctca
10621 tggttttgag ggtcaaccca attaaatgct ggaggattgg gataaggcaa agtggaccag
10681 ggaattgctt catttgcttg tgaaaaaaa ccaaacagaa ctagacagtt ttctaagttt
10741 ggctggaagg acgtgcatgg atgagatgac ctttcatata ctctctgtcc cggtccctca
10801 gacactgggt tttcccattt tcacactatc ttgcctagga cacccttct actggctgaa
10861 atcctatcta tgcaccaagt ccaaagactc tccctccttc aggaagtccc tgactgtccc
10921 cagaaggctg tttcctccct cctccaagtg ccctgagggc tggcattgga ttgcctttgc
10981 catggggttc tgctgtcggg aatgcaggcc tcgtctgctc aaggggaggc catgcattca
11041 gcatgcaggt gagatgcagc acctggccca ggccttgcac acgcaggtgc tctcttagtg
11101 ctccctggca aggatgggaa ggcatgttca gtcctaggag taggaagggg cagaggtgtt
11161 gatggcccct acagagcggc caaggacaag gagctgctgt tcgaaacagc cttcctgctc
11221 cccaacctgc ctcccaccca acaggttttg catatactct actgggaaga gggacacacc
11281 cgactgcatc actgccctcc aagtctctcc ctgccctgtc cagcatccag gagcacccct
11341 agttgggaa gcttctgtga ctccccctac aacagcctag gatggagtgg ggtttgtgaa
11401 caaatgcaga aggcagtctt agggaggtca gctgacatgc ccctggcctg tggctgggaa
11461 gtagcagagg ctaaggttct tccccgctct ggggttgcca ggagtagcac tggatcagtc
11521 aggtgacagg gctctcctct ctctgagcag gtccggtggc agccttcaag gtcgccacgc
11581 cgtattccct gtatgtctgt cccgagggc agaacgtcac cctcacctgc aggctcttgg
11641 gccctgtgga caaagggcac gatgtgacct tctacaagac gtggtaccgc agctcgaggg
11701 gcgaggtgca gacctgctca gagcgccggc ccatccgcaa cctcacgttc caggaccttc
11761 acctgcacca tggaggccac caggctgcca acaccagcca cgacctggct cagcgccacg
11821 ggctggagtc ggcctccgac caccatggca acttctccat caccatgcgc aacctgaccc
11881 tgctggatag cggcctctac tgctgcctgg tggtggagat caggcaccac cactggagc
11941 acaggggtcca tggtgccatg gagctgcagg tgcagacagg tgagggcatc ctgcacgtga
12001 cagcctggcg tgtgtggagg gctgcctgtc tgatggtgtg accattcatg acactgtgct
12061 gggcagagtg tgaggctgca tgggtaacac tggcactcca gggagtgtgt gggtgagatg
12121 gggtggtcaa gggtgtgtgg agtgtggggtt tgtagttagc tggagtgatg gagagggagg
12181 gtgtacctgg ctccatttgt gacagtgaga cttttaatg tgtgaggctg taggtacctg
12241 ggctgggagt gtgactgctc atgatgacat catggctgct gtgggtatag gcatcagtgg
12301 gactgattgg tgccctgggg catgactcag tggatggctg aatggctgtt ggagaatata
12361 tgcgtgtgtg tgtctgtctg ttcaggtgag agtgcaaggg cccatggttc ggatagaggt
12421 gtgggcacca gcgggtattc acatgcccct gggagtggca tgaaatgggg cagggtgaga
12481 acatgccagg gtgtgtgtgg gtgcaaacgt gtgcaggctg ccactgggcc aacactgccg
12541 agtaggcact agcgtgagaa cctggggcag gaggggaca ctggcctgga caagcctccc
12601 tggcctcctg ggcctgacac ccacctaatg gccccttctgt ttgttcccac aggcaaagat
12661 gcaccatcca actgtgtggt gtacccatcc tcctcccagg agagtgaaag taagggacca
12721 acctcttgcc ccttttgggt tctctgtttt cttctgtcct catcctgcac ccagaccctg
12781 tttggaactc tggcctcatc acccaagcc ctcagaaccc ccggtcctc ctccttttct
12841 gctgctgcac atcccttctg cttcctcctt ggtgcaatcc ccagaagccc actctccttc
12901 catctgctct ggagtctctg ctcctcttga ctctctggag tgactgtgcc ttggcagtga
12961 cctttggcca gggcaagtgc ctcatgacag gtactgggtg ccccaggcag ctaagtgccg
13021 ccctgccac cagcccccta tggcttggga aggctggggg tcctcttggc ctagaattaa
13081 actacttcag atttctgtgt tctgtgtttc tatgttcttc agatgttctc tgttgcaggg
13141 gagggaggag gaagaggttc aggaagggga acagaactac ctttcctgag ttcc

[gap 969 bp]

14164     ttttttcc ttcttggttg taaggagcca gagagaaaac gattgagcag tgttctcaag
14221 acaacttccc tgtcagtaaa acaccaaaaa ggaggccaaa tgtggtggct catgcctata
14281 atcccaacac tttgggaggc caggtgggcc tgaggtcagg agctcgagag cagtctgggc
14341 aaccgtctct actaaaaatg caaaacaatt agctgagtgg ccaggcacgg tggctcacac
14401 ctagaatccc agcactttgg gaggccaagg caggcgtatc atctgaggtc agaagtttga
14461 gaccagcctg gctaacaggg tgaaacccca tttctataaa aatacaaaaa aattagccag
```

FIG. 17

SISP-1 Genomic Sequence (5/8)

```
14521 gcatggtggt gcacgcctgt agtcccagct actcaagagg ctgaggcaag agaatcgctt
14581 gaacccggga gtcagaggtt acagtgagcc gagatcgcgc cactgcactc cagcctgctg
14641 atagagcaag actccatctc aaaaaaaaaa caacccaaaa tttgcctggc atggtggcag
14701 gcatctgtaa tcccagctac tcgggaggct gagacatgag agctgcttga acctgggagg
14761 cagaagttgc agtgagccga gatcacacca ctgcactcca gcctgggtga cagagcgaga
14821 ctctgtccca aaaaatcaaa aaatcactt ttggtagaga tgcactctcg ctatgttgcc
14881 caggctggtc ttgaactcct gggctcaatt gatcttccca ccttgacctc caaagtgctg
14941 ggattacagg tgtgagccac catgcctagc ctcagggaat tcttataaga actctatgaa
15001 gtaggcatca ccatcttctc tgtatccatg gaaagagagg cctagagatg tatgctaact
15061 tgcccaagct cacatagccc agggtagcat agctgggatc tggctgcagg cctgcttagc
15121 tctgcatact caccttcttc ccagcttggg gcagtgcagt gggtagcagt tagcccccg
15181 gtgcttgcca gagaggtgcc ctacagggta agagggcact gccctaaggg tgcctggcgc
15241 tgagaggttg ggtgagaata cccagcagct tggagacaaa atgcaagggc acctccctct
15301 tctgagaaga ggtcttggct tccacacccc tctatacect gtatgtgtca gacatccagt
15361 ggggaccagc ccctgctagg ccctggagat acaaaggcat ccaggaggac atgcacgagg
15421 acctaagccg gaatggggat cagctaaacc acggacccaa caaacccaa ctcaaaggct
15481 acagtgactt tttactcagc tacccttttt tcaaaccaac aaacaggcca agagcaaaat
15541 tagaacatgc attttggtca gagccatgtt ggtcaggctg gtctcgaact cctgggctca
15601 agtgatctac ccgccttggc tccccaaagt gctgggatta caggattgag ccactatgcc
15661 cagccccagt gccagcctct taatgttatc cttgggaagt aagagtgtag cttgactatg
15721 aaataacatg aaagtacaag ttaacctgag gtaggggaat gagactagag aagttggtgc
15781 ccaaggagct cctgcattgc tgagggctg tggtttctca gtgagctcag agaagggggtc
15841 taggcagctc atctcccttt gaacttcttc ccaccccca gcgcagcaga atgtgctgtc
15901 tgctttcacc cagcttcctc cctgggaaac caggcagccc aaccctcagc agccgaactc
15961 cctcctccat atatcccgt gggctaccag gcaggccctg gacaaaggcc gcctgagcag
16021 gccaggcccc tcccatccca ccctgctgtg tcagggcctg gcacactcct tagtgcggtg
16081 tcggcagcta cctctgccag cgcctgatca ccttcccagg ataagcctgg ctctggatgg
16141 tgagtgagta tgcctgcctt ccctgtgag tgccagccca ggcactggcc acgcttgggg
16201 gaaggggtgg ggaactgtgg cgaggctgag ctgcagag atgcctacgg cttcagaaag
16261 cagctggatc cacagacttg tccccaaacc tctgcgcccc tctgccccag cctcaactca
16321 gcccagatcg taaggaagcc tcaggctctc aaagtgaaat taagtcctga tctgatagag
16381 ggtccacata ggggaaatct ctacctgggg atagaagtta ggcagggata tctggccaag
16441 ctcacccctcc aaaggcagat agggaacagg tatcaatgag cacctggcaa agctcacaaa
16501 atgttgctta ctagccgtcc agaggagacc tgctttgatc actagaagag agtgctttgc
16561 aactggcttc tcaaatattg cccacaataa ggtcctttga tgggggtttt gaaatactga
16621 ggtgtctggg ttatagaatg tctttacttt caatattcca cgtcaaaatg cagccttgct
16681 aagatctgca gggaacctgc tgtaatgtgg agcggaactt gctttgtaat tagcatagca
16741 actgttcctg taccagtggg tacttctaaa gtgactgaaa acagtttgtt ctcatttgca
16801 gtatgaacaa acctcctgaa agcttgttta cgctgtcgga ttgtagagca aaacaaaaac
16861 agcctttatt cccaaacaaa tagcggaaag gcaacattta gaccacagcc atttacctct
16921 cagagctctt tggggcgaag ttgacactgt gacaaggtat cccagcccat ctttttggccc
16981 tgggaaaggc taaaattggg aaggaaatgc gtttatgttg gttgtggttc tgagggcacg
17041 tctgttccca gctaaactcc tgcagtcagc agatgccctg aaataaatca aacctcctca
17101 tgctgttggg acagcgaagc ttcgtgtaca ccttttggga gggcaattta gcaatagcct
17161 aaaagaaaat gcacatactc tttggctcag cactttgacc gctaggaatt tactacagat
17221 ttccttgctg agtgagccag gctgcgtgca caagttcatt gctacattat tagttatgct
17281 gaaaatggaa acaacatgtc taccaacagg ggactgcttc aataaattta gtgggagcca
17341 tgtgataaaa ctctaagcag aatgaggcag gggagacaga gagatgtcca agctgtgctc
17401 agtggggaaaa gcattgtcat atgatgctgc gtctgctgta tttgcaggga atataactag
17461 gaccataaca caaaaccgg cacacaggga tgatctcttc agagggggtc ttggtacaag
17521 gggaggagga gattcgaata ttttttaaac ttgtactttt tttggtagtt taataagttt
17581 aaaatggaaa aacattgtac aaggattcac gtttttctag ttctcacccc gggtgtttct
17641 cctgtgactt gtgtggtgag atcaagggt tctagaggcc ccatcccaga gctaaggagt
17701 ctctgggatg agttggggct ttttatctat tatgataaaa catatataat gtaaaatttg
17761 ccatttcaac cattttaagc ctacagtttg gtggcattaa ttcattcac aatgtgcaac
17821 cgtcaccact gtctattttc aaaactttca tcacttaggc ttcttttgac cttgagctct
17881 gtggcatggg gtctgcgaag gccctgctct ccctttttcag agaacaacct gtagccaagg
```

FIG. 18

```
SISP-1 Genomic Sequence (6/8)

17941 gtgttccagc tgtaccttgt gggctgggat gaggactctg ttccctctct tgcctggagc
18001 tgcctgagct gtaggtgaca ggtcttgttt ctgagtgctc cagggcata gggcggcagg
18061 cacagggctc tctttgaaag gagaaccgcc ttatcttcca tgcctctgta ggttgctggg
18121 ggtctagctg tgggactctg gggaaaggcg ggtctcctgc ttcctggcct tccctctctg
18181 agcctcagtt tatgctcagg aggagcaatg ggaatggggc ttcaccttgg ctacctctct
18241 gcccttcag acatcacggc tgcagccctg gctacgggtg cctgcatcgt aggaatcctc
18301 tgcctcccca tcatcctgct cctggtctac aagcaaaggc aggcagcctc caaccgccgt
18361 gagtattcct acctgcctgg ggtgggtgga cggtgcgagt gacctgctcc agccccagt
18421 tcagccctg ggattcgcaa aggcacgatg caggcacaat tccttttcat ttgagagttg
18481 ggagcagctg cacttccgc caggagctgg gcgaaatggc cgagagaaag gaggcatgcc
18541 atttccgggg gccaagtgcc caccagcccc tttggctccc aggcagtgct ggctcggcac
18601 tcaatacatg tcttctgaat gaatgatcat atgcagtagc tcaagttgct ttataaaagc
18661 aagttgctgc cactcagaga tccttggggg acctgtttaa ggtatgggcg tgcttgtttt
18721 gtaattagta gcaattgttg ggacaaaaaa tgatctttgg aatatcagaa gtggaagggg
18781 tcttacagac aacttagctc aacccttctct ttttccagat gagaaggcta agatcagtgg
18841 ggttacataa ctgactgaat gttacgtaac ttagtaagtg gcagagctag gactcaatct
18901 cagagctttc aacgcatgct ctttccaggg aatagaagtc caccatataa taaaaatgct
18961 ctcacttact cctcattgca agtccaagaa tttggtccta ccattgtccc cattttactg
19021 atgggcaaac ggaggcacag agggggttaag taacttgcct aaggaaccac acagcaaata
19081 agtggtgggg ctgggcttta agtcatggc acaaacatct ttcacctccc accctggcca
19141 ggtgacagtg ccccttgcct agttcctgac cctgcccttg agtcttggtt agtctgagtc
19201 ctccaagaag gggctaggga gttttttacc cttgcctccc ctccctggcc tcttccgtc
19261 tgcctggcta cagaggtaac tgagaaagga ttgctctggt gccaggtggc ttttggctcg
19321 caacttattt cctgtggccg gcccttaaca acttgtcatc cctccctccc ctcattcccg
19381 ggggccccca cgtgaagccc catagtgggt cactcggggg ctgtggccac ctcacccttg
19441 ctttcagaac tccctattc ctctcctaga acacaccaca acctacctgc aggaatccc
19501 atggctgggg gtgggtgggg gcaggtaaag ggcttggaac agaagagcaa cgctgggcag
19561 cagggcaggg ggagcaggtg ttgctgtgcc ctccctggtg gaaggctggc ccagagagcc
19621 tgctcaggaa tgaggcactc tcaggaaaaa aagaaaagga aagggctggg agccttgagg
19681 acggcagttt gctggagagg ccaacaggtg tggatttcca tcctgctttg gactgagcct
19741 cagtttcccc agctctaaaa tgggaccaac aaccctcacc ccaaaggtg gcacagagga
19801 tgagatgagg gaataccegt gtgcacctgc acgaagcctg acccatgagt cggctgtaag
19861 caatagccat ggttttgaata gatttcagga acttttgggt aacttccctg tgtttgttct
19921 gttgttgtgc ccctccccca ccatctgttt ccccatcgta atcagcagta aatctcctta
19981 aaacgagaag catctgtggg aggacatggg gtgctgcatg aaagagggaa gttggggtca
20041 ctgcatctaa ttggtggcca gtttgggggg tggggtgtcc caaggctgag gcaagcggca
20101 gcaacttgga tgagaagcag aaagtgagtg aagtggctgg gaagtgatcg gggacttgca
20161 ccttgtaagg tttccctgag agatgtcccc tagaatgcca ccctattagg caatgtaggg
20221 gataggacag agaggaccag gagccctcta attaggaact gacctaaaac actcccaccc
20281 agtaagtcat ggctaaagac cagaacctgg caaatgttca aacaagagac accagttagc
20341 aaattcaaga gttgaccttt gctcgatact taaatcctga aggtctgaca ctgtgtaagt
20401 caagccatag gagaaagcgc tggctgcctt tggtctcctg atggcagata gcgttcttac
20461 actcctggaa aatgcagata gagtttcatt tatcagtcgt caaaatgggc ccctcatgga
20521 ggccccatct gctggacaga cacgcagatc gctgctggac agcacccatg tgaaaagaaa
20581 tggagtccgg agctgtgcag ggcctcctg ggctcgctcc tgttccctgc agggcatctg
20641 ccagcagggg cagggatgtt gtatgggaa gccttcctt ccatgaccag cttctctgtc
20701 tgtctgtccc taggtgccca ggagctggtg cggatggaca ggtaaggccc atggagacct
20761 tcttgagaaa acttcctggg ccggctatcc aggaagagat acttctgtgc agtaggggcc
20821 ctgtttagct gcctagagca gctggtcaga agagcctctg ccatctgctg ctgaagcctg
20881 cacatctgtg cagattggct gttctcctgc caccccgact cagcaggctg agctctgatt
20941 ctgctcagat gtgtcatgca cccaccttcg ggtctcagtg gtcagcctgg gccaggatgg
21001 ggacagggag gaagcactgt ctgggcaga cagtgagaca tgcaaaggag gccagcgggc
21061 ccagcccag ccacagccct tgagctgtgc ctcctgcccg cagagaactc caaggagaaa
21121 gctgttaggc cgctgcaggc cacaagggca gaggctgagg ggtcccagag tggtgcagtg
21181 ggctgggtct aggggcagag gggatgggga ctgtgtattg gtgtgctctg ggcaggaagc
21241 tgccatgcag cctggcctgg aggtgtgtt caggaaccc aagttcctgc cccggtacct
21301 gcaacaccaa acacaaagct cctctaggtg tttgaaaggg atgatcttca agacaggttg
```

FIG. 19

SISP-1 Genomic Sequence (7/8)

```
21361 aaggaagtcc tgcttgcaac tcatctagaa tctaagagtt gcagggtct tcagaagtta
21421 tcccactccc aactgggaag agaagagaac ccctcccctc agctcaagac aggctttggg
21481 gatgttcgat cctaatgcca tcaactctat tgaccaaaga gaaacttgtc cccaaattcc
21541 tgaggctgaa gttctagaag tgtctgtgat ttttggcttc ctggctgtgc ccggggttga
21601 tggtcagacc acagggagga gctgggtct gttctggtgg gccctgatgc cctcagctca
21661 ggacaggtgg gcaggtgcag cccatggcct ttgctctgtg ggcctggctc ctgccttctt
21721 gcttggagat gctgctgagg cttggggatg gggatgtagg tgagagaaag ggaggagaga
21781 aaaactgggg gcagggaggg cagagttcac gctccggaca gcacagatga ccttccattc
21841 tggttctgtg gcagcaacat tcaagggatt gaaaaccccg gctttgaagc ctcaccacct
21901 gcccagggga tacccgaggc caaagtcagg caccccctgt cctatgtggc ccagcggcag
21961 ccttctgagt ctgggcggca tctgctttcg gagcccagca ccccctgtc tcctccaggc
22021 cccggagacg tcttcttccc atccctgggt aagtgtttcc tgaccttcac agcacgatga
22081 cctgtaaggt catgacctca tggcctgcag ggcatcggcc tcactccctg ccctccctga
22141 agagttccac ggcctcacgg ggtggggttg agggtgaggg acagaggggc ccccattcac
22201 ctccctgaag agttccacgg cctcacgggg tggggttgag ggtgagggac agaggggccc
22261 ccattcacct ccctgaagag ttccacggcc tcacggggtg gggttgaggg tgagggacag
22321 aggggccccc attcacctcc ctgaagagtt ccacggcctc acgggtgggg ttgagggtg
22381 aggggcagag ggcccgtt cactttgctt ctccttttct tgcagaccct gtccctgact
22441 ctccaaactt tgaggtcatc tagcccagct ggggacagt gggctgttgt ggctgggtct
22501 gggcaggtg catttgagcc agggctggct ctgtgagtgg cctccttggc ctcggccctg
22561 gttccctccc tcctgctctg ggctcagata ctgtgacatc ccagaagccc agccctcaa
22621 cccctctgga tgctacatgg ggatgctgga cggctcagcc cctgttccaa ggattttggg
22681 gtgctgagat tctccctag agacctgaaa ttcaccagct acagatgcca aatgacttac
22741 atcttaagaa gtctcagaac gtccagccct tcagcagctc tgttctgag acatgagcct
22801 tgggatgtgg cagcatcagt gggacaagat ggacactggg ccaccctccc aggcaccaga
22861 cacagggcac ggtggagaga cttctcccc gtggccgcct tggctcccc gttttgcccg
22921 aggctgctct tctgtcagac ttcctctttg taccacagtg gtctgggc caggcctgcc
22981 tgcccactgg ccatcgccac cttccccagc tgcctcctac cagcagtttc tctgaagatc
23041 tgtcaacagg ttaagtcaat ctggggcttc cactgcctgc attccagtcc ccagagcttg
23101 gtggtcccga aacgggaagt acatattggg gcatggtggc ctccgtgagc aaatggtgtc
23161 ttgggcaatc tgaggccagg acagatgttg ccccacccac tggagatggt gtgagggag
23221 gtgggtgggg ccttctggga aggtgagtgg agaggggcac ctgcccccg ccctccccat
23281 cccctactcc cactgctcag cgcgggccat tgcaagggtg ccacacaatg tcttgtccac
23341 cctgggacac ttctgagtat gaagcgggat gctattaaaa actacatggg gaaacaggtg
23401 caaaccctgg agatggattg taagagccag tttaaatctg cactctgctg ctcctcccc
23461 accccacct tccactccat acaatctggg cctggtggag tcttcgcttc agagccattc
23521 ggccaggtgc gggtgatgtt cccatctcct gcttgtgggc atgccctggc tttgttttta
23581 tacacatagg caaggtgagt cctctgtgga attgtgattg aaggatttta aagcagggga
23641 ggagagtagg gggcatctct gtacactctg ggggtaaaac agggaaggca gtgcctgagc
23701 atggggacag gtgaggtggg gctgggcaga ccccctgtag cgtttagcag gatgggggcc
23761 ccaggtactg tggagagcat agtccagcct gggcatttgt ctcctagcag cctacactgg
23821 ctctgctgag ctgggcctgg gtgctgaaag ccaggatttg gggctaggcg ggaagatgtt
23881 cgcccaattg cttgggggt tgggggatg gaaaaggga gcacctctag gctgcctggc
23941 agcagtgagc cctgggcctg tggctacagc cagggaaccc cacctggaca catggccctg
24001 cttctaagcc ccccagttag gcccaaagga atggtccact gagggcctcc tgctctgcct
24061 gggctgggcc aggggctttg aggagaggt aaacataggc ccggagatgg ggctgacacc
24121 tcgagtggcc agaatatgcc caaaccccgg cttctccctt gtccctaggc agaggggggt
24181 cccttctttt gttccctctg gtcaccacaa tgcttgatgc cagctgccat aggaagaggg
24241 tgctggctgg ccatggtggc acacacctgt cctcccagca ctttgcaggg ctgaggtgga
24301 aggaccgctt aagcccaggt gttcaaggct gctgtgagct gtgttcgagc cactacactc
24361 cagcctgggg acggagcaaa actttgcctc aaaacaaatt ttaaaaagaa agaaagaagg
24421 aaagagggta tgttttcac aattcatggg ggcctgcatg gcaggagtgg ggacaggaca
24481 cctgctgttc ctggagtcga aggacagcc cacagcccag attccggttc tcccaactca
24541 ggaagagcat gccctgccct ctggggaggc tggcctgacc ccagccctca gctgctgacc
24601 ttgaggcaga gacaacttct aagaatttgg ctgccagacc ccaggcctgg ctgctgctgt
24661 gtggagaggg aggcggcccg cggcagaaca gccaccgcac ttcctcctca gcttcctctg
24721 gtgcggccct gccctctctt ctctggaccc ttttacaact gaacgcatct gggcttcgtg
```

FIG. 20

SISP-1 Genomic Sequence (8/8)

```
24781 gtttcctgtt ttcagcgaaa tttactctga gctcccagtt ccatcttcat ccatggccac
24841 aggccctgcc tacaacgcac tagggacgtc cctccctgct gctgctgggg aggggcaggc
24901 tgctggagcc gccctctgag ttgcccggga tggtagtgcc tctgatgcca gccctggtgg
24961 ctgtgggctg gggtgcatgg gagagctggg tgcgagaaca tggcgcctcc aggggcggg
25021 aggagcacta ggggctgggg caggaggctc ctggagcgct ggattcgtgg cacagtctga
25081 ggccctgaga gggaaatcca tgcttttaag aactaattca ttgttaggag atcaatcagg
25141 aattagggc catcttacct atctcctgac attcacagtt taatagagac ttcctgcctt
25201 tattccctcc cagggagagg ctgaaggaat ggaattgaaa gcaccatttg gagggttttg
25261 ctgacacagc ggggactgct cagcactccc taaaaacaca ccatggaggc cactggtgac
25321 tgctggtggg caggctggcc ctgcctgggg gagtccgtgg cgatgggcgc tggggtggag
25381 gtgcaggagc cccaggacct gcttttcaaa agacttctgc ctgaccagag ctcccactac
25441 atgcagtggc ccagggcaga ggggctgata catggccttt ttcagggggt gctcctcgcg
25501 gggtggactt gggagtgtgc agtgggacag ggggctgcag gggtcctgcc accaccgagc
25561 accaacttgg ccctgggt cctgcctcat gaatgaggcc ttccccaggg ctggcctgac
25621 tgtgctgggg ctgggttaa cgttttctca gggaaccaca atgcacgaaa gaggaactgg
25681 ggttgctaac caggatgctg ggaacaaagg cctcttgaag cccagccaca gccagctga
25741 gcatgaggcc cagcccatag acggcacagg ccacctggcc cattccctgg gcattccctg
25801 ctttgcattg ctgcttctct tcaccccatg gaggctatgt caccctaact atcctggaat
25861 gtgttgagag ggattctgaa tgatcaatat agcttggtga gacagtgccg agatagatag
25921 ccatgtctgc cttgggcacg ggagagggaa gtggcagcat gcatgctgtt tcttggcctt
25981 ttctgttaga atacttggtg cttttccaaca cactttcaca tgtgttgtaa cttgtttgat
26041 ccaccccctt ccctgaaaat cctgggaggt tttattgctg ccatttaaca cagagggcaa
26101 tagaggttct gaaaggtctg tgtcttgtca aaacaagtaa acggtggaac tacgactaaa
```

FIG. 21

SISP-1 mRNA
GGGTCTCAGAAACATCAGAGAGAGGTTTGTAGTTTCGCTCTGGAGGGCAGAACAGCCGGAAGAAGAACCAACTGCTGGTTATCTCA
GGCTGGAGGTGGTAGCTGAAGGGGGTGTGGACAGTAAGGATTTGCCGGGAAAAAGGAAGGGTCAGGACATTTCGTGAAGTGGGAGG
ACTTGAGCTGAGCCCTGAGGGATGAGAAGAATTAGGAGGGGAGAGACATTCCAGTGGTGCCAGCAGTGCTGGGTGTGGGTGCAAGA
GCAGAGGCACTAGAAGTTAGGGTGCATCAGAGTGTCCTGCAGATATCCAGGCACCAGGGAGGGAGGGCGGGTGCACAGCCAGGCGG
ACAGCTGAGGCCTCTGCCGGAGGGGAGCTTGCAGGATGTGCTGTGGGCACGCCAACAGGTGTTGCCTGCATATCTGTGTGTGTCC
CGGGGTAGGGATGTGCTGATCTTGGCGTGTAGTCCTGCACCTGTTCTGTGTGTGTGTGTGTGTGTGTGTGTGTGTGTGCG
CGCGCGCATGCACTCAGGGTGCTCCAGGCTCTGAATCTACAGTT<u>AAA</u>C<u>TGG</u>C<u>TCCAGCTTG</u>CCTAGCTCTTCACAATGTCAGATTT
CATTCATTCACTCATTTACTCACTCATTCCACAGCTGGGAGTGCCTACCACATACCAAGCCCTGGTCTGGCTGGAGGATGTAGGGT
ACAAGTCTCTGTCCCCAGATCACTCAAAGGCTGGTGGCTGAGGGCAGATGCAAGCCATGGTAACGTCTATCACGCTGTTAGAGGTA
GATCTACTTCTTAGGCTGCGCAGCAATAATAATTTCTCTCCAAAAGGACTGGGGGACGGTAGAACGGGCTTTAAACTGCCGATCAA
GTGGAGCTGACTCGCTGGGACGCACGCTGGCTCCCCACCCACGGGCCGGCCTCCGGGAAGCCCCTCCCACGCGGCCCTCGGAGAG
GCAGTTCCCCCACACGGCCCCCGGGGGCGCTGCGCGAAGGGGCGGGTGCCTGGAGCACGGCGCTGGGGCCGCCCGCAGCGCTCA
CTCGCTCGCACTCAGTCGCGGGAGGCTTCCCCGCGCCGGCCGCGTCCCGCCCGCTCCCCGGCACCAGAAGTTCCTCTGCGCGTCCG
ACGGCGACATGGGCGTCCCCACGGCCCTGGAGGCCGGCAGCTGGCGCTGGGGATC
CCTGCTCTTCGCTCTCTTCCTGGCTGCGTCCCTAGGTCCGGTGGCAGCCTTCAAGGTCGCCACGCCGTATTCCCTGTATGTCTGTC
CCGAGGGGCAGAACGTCACCCTCACCTGCAGGCTCTTGGGCCCTGTGGACAAAGGGCACGATGTGACCTTCTACAAGACGTGGTAC
CGCAGCTCGAGGGGCGAGGTGCAGACCTGCTCAGAGCGCCGGCCCATCCGCAACCTCACGTTCCAGGACCTTCACCTGCACCATGG
AGGCCACCAGGCTGCCAACACCAGCCACGACCTGGCTCAGCGCCACGGGCTGGAGTCGGCCTCCGACCACCATGGCAACTTCTCCA
TCACCATGCGCAACCTGACCCTGCTGGATAGCGGCCTCTACTGCTGCCTGGTGGTGGAGATCAGGCACCACCACTCGGAGCACAGG
GTCCATGGTGCCATGGAGCTGCAGGTGCAGACAGGCAAAGATGCACCATCCAACTGTGTGGTGTACCCATCCTCCTCCCAGGAGAG
TGAAAACATCACGGCTGCAGCCCTGGCTACGGGTGCCTGCATCGTAGGAATCCTCTGCCTCCCCCTCATCCTGCTCCTGGTCTACA
AGCAAAGGCAGGCAGCCTCCAACCGCCGTGCCCAGGAGCTGGTGCGGATGGACAGCAACATTCAAGGGATTGAAAACCCCGGCTTT
GAAGCCTCACCACCTGCCCAGGGGATACCCGAGGCCAAAGTCAGGCACCCCCTGTCCTATGTGGCCCAGCGGCAGCCTTCTGAGTC
TGGGCGGCATCTGCTTTCGGAGCCCAGCACCCCCCTGTCTCCTCCAGGCCCCGGAGACGTCTTCTTCCCCATCCCTGGACCCTGTCC
CTGACTCTCCAAACTTTGAGGTCATCTAGCCCAGCTGGGGACAGTGGGCTGTTGTGGCTGGGTCTGGGGCAGGTGCATTTGAGCC
AGGGCTGGCTCTGTGAGTGGCCTCCTTGGCCTCGGCCCTGGTTCCCTCCCTCCTGCTCTGGGCTCAGATACTGTGACATCCCAGAA
GCCCAGCCCCTCAACCCCTCTGGATGCTACATGGGGATGCTGGACGGCTCAGCCCCTGTTCCAAGGATTTTGGGGTGCTGAGATTC
TCCCCTAGAGACCTGAAATTCACCAGCTACAGATGCCAAATGACTTACATCTTAAGAAGTCTCAGAACGTCCAGCCCTTCAGCAGC
TCTCGTTCTGAGACATGAGCCTTGGGATGTGGCAGCATCAGTGGGACAAGATGGACACTGGGCCACCCTCCCAGGCACCAGACACA
GGGCACGGTGGAGAGACTTCTCCCCCGTGGCCGCCTTGGCTCCCCGTTTTGCCCGAGGCTGCTCTTCTGTCAGACTTCCTCTTTG
TACCACAGTGGCTCTGGGGCCAGGCCTGCCTGCCCACTGGCCATCGCCACCTTACCCAGCTGCCTCCTACCAGCAGTTTCTCTGAA
GATCTGTCAACAGGTTAAGTCAATCTGGGGCTTCCACTGCCTGCATTCCAGTCCCCAGAGCTTGGTGGTCCCGAAACGGGAAGTAC
ATATTGGGGCATGGTGGCCTCCGTGAGCAAATGGTGTCTTGGGCAATCTGAGGCCAGGACAGATGTTGCCCCACCCACTGGAGATG
GTGCTGAGGGAGGTGGGTGGGGCCTTCTGGGAAGGTGAGTGGAGAGGGGCACCTGCCCCCCGCCCTCCCCATCCCCTACTCCCACT
GCTCAGCGCGGGCCATTGCAAGGGTGCCACACAATGTCTTGTCCACCCTGGGACACTTCTGAGTATGAAGCGGGATGCTATTAAAA
ACTACATGGGGAAACAGGTGCAAAAAAAAAAAAAAAAAAAAAAA

FIG. 22

SISP-1 mRNA without 5' and 3' untranslated region

```
  1 atgggcgtcc ccacggccct ggaggccggc agctggcgct ggggatccct gctcttcgct
 61 ctcttcctgg ctgcgtccct aggtccggtg gcagccttca aggtcgccac gccgtattcc
121 ctgtatgtct gtcccgaggg gcagaacgtc accctcacct gcaggctctt gggccctgtg
181 gacaaagggc acgatgtgac cttctacaag acgtggtacc gcagctcgag gggcgaggtg
241 cagacctgct cagagcgccg gcccatccgc aacctcacgt tccaggacct tcacctgcac
301 catggaggcc accaggctgc caacaccagc cacgacctgg ctcagcgcca cgggctggag
361 tcggcctccg accaccatgg caacttctcc atcaccatgc gcaacctgac cctgctggat
421 agcggcctct actgctgcct ggtggtggag atcaggcacc accactcgga gcacagggtc
481 catggtgcca tggagctgca ggtgcagaca ggcaaagatg caccatccaa ctgtgtggtg
541 tacccatcct cctcccagga gagtgaaaac atcacggctg cagccctggc tacgggtgcc
601 tgcatcgtag gaatcctctg cctcccctc atcctgctcc tggtctacaa gcaaaggcag
661 gcagcctcca accgccgtgc ccaggagctg gtgcggatgg acagcaacat tcaagggatt
721 gaaaaccccg gctttgaagc ctcaccacct gcccagggga tacccgaggc caaagtcagg
781 cacccctgt cctatgtggc ccagcggcag ccttctgagt ctgggcggca tctgctttcg
841 gagcccagca ccccctgtc tcctccaggc cccggagacg tcttcttccc atccctggac
901 cctgtccctg actctccaaa ctttgaggtc atctag
```

FIG. 23

SISP-1 mRNA with 5' and 3' untranslated region (1/2)
*Nucleotides in untranslated region are shown in italicized letters.*

<EXON 1 including Untranslated region>

*gcgtcccgcc cgctccccgg caccagaagt tcctctgcgc gtccgacggc ga*catgggcg tccccacggc cctggaggcc ggcagctggc gctggggatc cctgctcttc gctctcttcc tggctgcgtc ccta

<EXON2> ggtccg gtggcagcct tcaaggtcgc cacgccgtat tccctgtatg tctgtcccga ggggcagaac gtcaccctca cctgcaggct cttgggccct gtggacaaag ggcacgatgt gaccttctac aagacgtggt accgcagctc gaggggcgag gtgcagacct gctcagagcg ccggcccatc cgcaacctca cgttccagga ccttcacctg caccatggag gccaccaggc tgccaacacc agccacgacc tggctcagcg ccacgggctg gagtcggcct ccgaccacca tggcaacttc tccatcacca tgcgcaacct gaccctgctg gatagcggcc tctactgctg cctggtggtg gagatcaggc accaccactc ggagcacagg gtccatggtg ccatggagct gcaggtgcag acag

<EXON3> gcaaag atgcaccatc caactgtgtg gtgtacccat cctcctccca ggagagtgaa a

<EXON4> acatcacgg ctgcagccct ggctacgggt gcctgcatcg taggaatcct ctgcctcccc ctcatcctgc tcctggtcta caagcaaagg caggcagcct ccaaccgcc

<EXON5> g tgcccaggag ctggtgcgga tggacag

FIG. 24

SISP-1 mRNA with 5' and 3' untranslated region (2/2)

\<EXON6\> caa cattcaaggg attgaaaacc ccggctttga agcctcacca
cctgcccagg ggatacccga ggccaaagtc aggcaccccc tgtcctatgt ggcccagcgg
cagccttctg agtctgggcg gcatctgctt tcggagccca gcaccccct gtctcctcca
ggccccggag acgtcttctt cccatccctgg \<EXON7 including untranslated region\>

*accctgtcc ctgactctcc aaactttgag gtcatctagc ccagctgggg gacagtgggc
tgttgtggct gggtctgggg caggtgcatt tgagccaggg ctggctctgt gagtggcctc
cttggcctcg gccctggttc cctccctcct gctctgggct cagatactgt gacatcccag
aagcccagcc cctcaacccc tctggatgct acatggggat gctggacggc tcagccctg
ttccaaggat tttggggtgc tgagattctc ccctagagac ctgaaattca ccagctacag
atgccaaatg acttacatct taagaagtct cagaacgtcc agcccttcag cagctctcgt
tctgagacat gagccttggg atgtggcagc atcagtggga caagatggac actgggccac
cctcccaggc accagacaca gggcacggtg gagagacttc tccccgtgg ccgccttggc
tccccgttt tgcccgaggc tgctcttctg tcagacttcc tctttgtacc acagtggctc
tggggccagg cctgcctgcc cactggccat cgccaccta cccagctgcc tcctaccagc
agtttctctg aagatctgtc aacaggttaa gtcaatctgg ggcttccact gcctgcattc
cagtccccag agcttggtgg tcccgaaacg ggaagtacat attggggcat ggtggcctcc
gtgagcaaat ggtgtcttgg gcaatctgag gccaggacag atgttgcccc acccactgga
gatggtgctg agggaggtgg gtggggcctt ctgggaaggt gagtggagag gggcacctgc
ccccgccct ccccatcccc tactcccact gctcagcgcg ggccattgca agggtgccac
acaatgtctt gtccaccctg ggacacttct gagtatgaag cgggatgcta ttaaaaacta
catgggaaa caggtgcaaa*

Met G V P T A L E A G S W R W G S L L F A L F L A A S L G P V A A F K V A
T P Y S L Y V C P E G Q N V T L T C R L L G P V D K G H D V T F Y K T W Y
R S S R G E V Q T C S E R R P I R N L T F Q D L H L H H G G H Q A A N T S
H D L A Q R H G L E S A S D H H G N F S I T M R N L T L L D S G L Y C C I
V V E I R H H H S E H R V H G A M E L Q V Q T G K D A P S N C V V Y P S S
S Q E S E N I T A A A L A T G A C I V G I L C P L I L L V Y K Q R Q A
A S N R R A Q E L V R M D S N I Q G I E N P G F E A S P P A Q G I P E A K
V R H P L S Y V A Q R Q P S E S G R H L L S E P S T P L S P P G P G D V E
F P S L D P V P D S P N F E V I Stop

SEQUENCE LISTING

```
<160> NUMBER OF SEQ ID NOS: 10

<210> SEQ ID NO 1
<211> LENGTH: 1950
<212> TYPE: DNA
<213> ORGANISM: Homo sapiens
<220> FEATURE:
<221> NAME/KEY: CDS
<222> LOCATION: (54)..(986)

<400> SEQUENCE: 1
gcgtcccgcc cgctccccgg caccagaagt tcctctgcgc gtccgacggc gac          53 atg ggc gtc ccc acg gcc ctg gag gcc ggc agc tgg cgc tgg gga tcc   101
Met Gly Val Pro Thr Ala Leu Glu Ala Gly Ser Trp Arg Trp Gly Ser
  1               5                  10                  15 ctg ctc ttc gct ctc ttc ctg gct gcg tcc cta ggt ccg gtg gca gcc   149
Leu Leu Phe Ala Leu Phe Leu Ala Ala Ser Leu Gly Pro Val Ala Ala
             20                  25                  30 ttc aag gtc gcc acg ccg tat tcc ctg tat gtc tgt ccc gag ggg cag   197
Phe Lys Val Ala Thr Pro Tyr Ser Leu Tyr Val Cys Pro Glu Gly Gln
         35                  40                  45 aac gtc acc ctc acc tgc agg ctc ttg ggc cct gtg gac aaa ggg cac   245
Asn Val Thr Leu Thr Cys Arg Leu Leu Gly Pro Val Asp Lys Gly His
     50                  55                  60 gat gtg acc ttc tac aag acg tgg tac cgc agc tcg agg ggc gag gtg   293
Asp Val Thr Phe Tyr Lys Thr Trp Tyr Arg Ser Ser Arg Gly Glu Val
 65                  70                  75                  80 cag acc tgc tca gag cgc cgg ccc atc cgc aac ctc acg ttc cag gac   341
Gln Thr Cys Ser Glu Arg Arg Pro Ile Arg Asn Leu Thr Phe Gln Asp
                 85                  90                  95 ctt cac ctg cac cat gga ggc cac cag gct gcc aac acc agc cac gac   389
Leu His Leu His His Gly Gly His Gln Ala Ala Asn Thr Ser His Asp
            100                 105                 110 ctg gct cag cgc cac ggg ctg gag tcg gcc tcc gac cac cat ggc aac   437
Leu Ala Gln Arg His Gly Leu Glu Ser Ala Ser Asp His His Gly Asn
        115                 120                 125 ttc tcc atc acc atg cgc aac ctg acc ctg ctg gat agc ggc ctc tac   485
Phe Ser Ile Thr Met Arg Asn Leu Thr Leu Leu Asp Ser Gly Leu Tyr
    130                 135                 140 tgc tgc ctg gtg gtg gag atc agg cac cac cac tcg gag cac agg gtc   533
Cys Cys Leu Val Val Glu Ile Arg His His His Ser Glu His Arg Val
145                 150                 155                 160
```

```
cat ggt gcc atg gag ctg cag gtg cag aca ggc aaa gat gca cca tcc    581
His Gly Ala Met Glu Leu Gln Val Gln Thr Gly Lys Asp Ala Pro Ser
            165                 170                 175 aac tgt gtg gtg tac cca tcc tcc tcc cag gag agt gaa aac atc acg    629
Asn Cys Val Val Tyr Pro Ser Ser Ser Gln Glu Ser Glu Asn Ile Thr
        180                 185                 190 gct gca gcc ctg gct acg ggt gcc tgc atc gta gga atc ctc tgc ctc    677
Ala Ala Ala Leu Ala Thr Gly Ala Cys Ile Val Gly Ile Leu Cys Leu
    195                 200                 205 ccc ctc atc ctg ctc ctg gtc tac aag caa agg cag gca gcc tcc aac    725
Pro Leu Ile Leu Leu Leu Val Tyr Lys Gln Arg Gln Ala Ala Ser Asn
210                 215                 220 cgc cgt gcc cag gag ctg gtg cgg atg gac agc aac att caa ggg att    773
Arg Arg Ala Gln Glu Leu Val Arg Met Asp Ser Asn Ile Gln Gly Ile
225                 230                 235                 240 gaa aac ccc ggc ttt gaa gcc tca cca cct gcc cag ggg ata ccc gag    821
Glu Asn Pro Gly Phe Glu Ala Ser Pro Pro Ala Gln Gly Ile Pro Glu
                245                 250                 255 gcc aaa gtc agg cac ccc ctg tcc tat gtg gcc cag cgg cag cct tct    869
Ala Lys Val Arg His Pro Leu Ser Tyr Val Ala Gln Arg Gln Pro Ser
            260                 265                 270 gag tct ggg cgg cat ctg ctt tcg gag ccc agc acc ccc ctg tct cct    917
Glu Ser Gly Arg His Leu Leu Ser Glu Pro Ser Thr Pro Leu Ser Pro
        275                 280                 285 cca ggc ccc gga gac gtc ttc ttc cca tcc ctg gac cct gtc cct gac    965
Pro Gly Pro Gly Asp Val Phe Phe Pro Ser Leu Asp Pro Val Pro Asp
    290                 295                 300 tct cca aac ttt gag gtc atc tagc ccagctgggg gacagtgggc tgttgtggct  1020
Ser Pro Asn Phe Glu Val Ile
305                 310 gggtctgggg caggtgcatt tgagccaggg ctggctctgt gagtggcctc cttggcctcg  1080
gccctggttc cctccctcct gctctgggct cagatactgt gacatcccag aagcccagcc  1140
cctcaacccc tctggatgct acatggggat gctggacggc tcagcccctg ttccaaggat  1200
tttggggtgc tgagattctc ccctagagac ctgaaattca ccagctacag atgccaaatg  1260
acttacatct taagaagtct cagaacgtcc agcccttcag cagctctcgt tctgagacat  1320
gagccttggg atgtgcagc atcagtggga caagatggac actgggccac ctcccaggc   1380 accagacaca gggcacggtg gagagacttc tcccccgtgg ccgccttggc tccccgtttt  1440
tgcccgaggc tgctcttctg tcagacttcc tctttgtacc acagtggctc tggggccagg  1500
cctgcctgcc cactggccat cgccacctta cccagctgcc tcctaccagc agtttctctg  1560
aagatctgtc aacaggttaa gtcaatctgg ggcttccact gcctgcattc cagtccccag  1620
agcttggtgg tcccgaaacg ggaagtacat attggggcat ggtggcctcc gtgagcaaat  1680
ggtgtcttgg gcaatctgag gccaggacag atgttgcccc acccactgga gatggtgctg  1740
agggaggtgg gtggggcctt ctgggaaggt gagtggagag gggcacctgc ccccgcccct  1800
ccccatcccc tactcccact gctcagcgcg ggccattgca agggtgccac acaatgtctt  1860
gtccaccctg ggacacttct gagtatgaag cgggatgcta ttaaaaacta catggggaaa  1920
caggtgcaaa aaaaaaaaa aaaaaaaaa                                     1950
```

<210> SEQ ID NO 2
<211> LENGTH: 311
<212> TYPE: PRT
<213> ORGANISM: Homo sapiens

<400> SEQUENCE: 2

```
Met Gly Val Pro Thr Ala Leu Glu Ala Gly Ser Trp Arg Trp Gly Ser
 1               5                  10                  15

Leu Leu Phe Ala Leu Phe Leu Ala Ala Ser Leu Gly Pro Val Ala Ala
                20                  25                  30

Phe Lys Val Ala Thr Pro Tyr Ser Leu Tyr Val Cys Pro Glu Gly Gln
            35                  40                  45

Asn Val Thr Leu Thr Cys Arg Leu Leu Gly Pro Val Asp Lys Gly His
        50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
130                 135                 140

Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Glu Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
290                 295                 300

Ser Pro Asn Phe Glu Val Ile
305                 310

<210> SEQ ID NO 3
<211> LENGTH: 13194
<212> TYPE: DNA
<213> ORGANISM: Homo sapiens
<220> FEATURE:
<221> NAME/KEY: exon
<222> LOCATION: (89)..(222)
<223> OTHER INFORMATION: Nucleotides 89-141 are an untranslaed region.
<220> FEATURE:
<221> NAME/KEY: exon
<222> LOCATION: (11550)..(11979)
<220> FEATURE:
<221> NAME/KEY: exon
<222> LOCATION: (12653)..(12709)

<400> SEQUENCE: 3
```

-continued

```
gggggcgggt gcctggagca cggcgctggg gccgcccgca gcgctcactc gctcgcactc    60
agtcgcggga ggcttccccg cgccggccgc gtcccgcccg ctccccggca ccagaagttc   120
ctctgcgcgt ccgacggcga catgggcgtc cccacggccc tggaggccgg cagctggcgc   180
tggggatccc tgctcttcgc tctcttcctg gctgcgtccc taggtccggt ggcagccttc   240
aaggtcgcca cgccgtattc cctgtatgtc tgtcccgagg ggcagaacgt caccctcacc   300
tgcaggctct gggccctgt ggacaaaggg cacgatgtga ccttctacaa gacgtggtac   360
cgcagctcga ggggcgaggt gcagacctgc tcagagcgcc ggcccatccg caacctcacg   420
ttccaggacc ttcacctgca ccatggaggc caccaggctg ccaacaccag ccacgacctg   480
gctcagcgcc acgggctgga gtcggcctcc gaccaccatg gcaacttctc catcaccatg   540
cgcaacctga ccctgctgga tagcggcctc tactgctgcc tggtggtgga gatcaggcac   600
caccactcgg agcacagggt ccatggtgcc atggagctgc aggtgcagac aggcaaagat   660
gcaccatcca actgtgtggt gtacccatcc tcctcccagg atagtgaaaa catcacggct   720
gcagccctgg ctacgggtgc ctgcatcgta ggaatcctct gcctccccct catcctgctc   780
ctggtctaca gcaaaggca ggcagcctcc aaccgccgtg cccaggagct ggtgcggatg   840
gacagcaaca ttcaagggat tgaaaacccc ggctttgaag cctcaccacc tgcccagggg   900
atacccgagg ccaaagtcag gcaccccctg tcctatgtgg cccagcggca gccttctgag   960
tctgggcggc atctgctttc ggagcccagc acccccctgt ctcctccagg ccccggagac  1020
gtcttcttcc catccctgga ccctgtccct gactctccaa actttgaggt catctagccc  1080
agctggggga cagtgggctg ttgtggctgg gtctggggca ggtgcatttg agccagggct  1140
ggctctgtga gtggcctcct tggcctcggc cctggttccc tccctcctgc tctgggctca  1200
gatactgtga catcccagaa gcccagcccc tcaacccctc tggatgctac atggggatgc  1260
tggacggctc agcccctgtt ccaaggattt tggggtgctg agattctccc ctagagacct  1320
gaaattcacc agctacagat gccaaatgac ttacatctta agaagtctca gaacgtccag  1380
cccttcagca gctctcgttc tgagacatga gccttgggat gtggcagcat cagtgggaca  1440
agatggacac tgggccaccc tcccaggcac cagacacagg gcacggtgga gagacttctc  1500
ccccgtggcc gccttggctc cccgttttg cccgaggctg ctcttctgtc agacttcctc  1560
tttgtaccac agtggctctg gggccaggcc tgcctgccca ctggccatcg ccaccttccc  1620
cagctgcctc ctaccagcag tttctctgaa gatctgtcaa caggttaagt caatctgggg  1680
cttccactgc ctgcattcca gtcccagag cttggtggtc ccgaaacggg aagtacatat  1740 tgggcatgg tggcctccgt gagcaaatgg tgtcttgggc aatctgaggc caggacagat  1800
gttgccccac ccactggaga tggtgctgag ggaggtgggg ggggccttct gggaaggtga  1860
gtggagaggg gcacctgccc cccgccctcc ccatccccta ctcccactgc tcagcgcggg  1920
ccattgcaag ggtgccacac aatgtcttgt ccacctgggg acacttctga gtatgaagcg  1980
ggatgctatt aaaaactaca tgggaaaaca ggtgcaaacc ctggagatgg attgtaagag  2040
ccagtttaaa tctgcactct gctgctcctc ccccacccc accttccact ccatacaatc  2100
tgggcctggt ggagtcttcg cttcagagcc attcggccag gtgcgggtga tgttcccatc  2160
tcctgcttgt gggcatgccc tggctttgtt tttatacaca taggcaaggt gagtcctctg  2220
tggaattgtg attgaaggat tttaaagcag gggaggagag taggggcat ctctgtacac  2280 tctggggta aaacagggaa ggcagtgcct gagcatgggg acaggtgagg tggggctggg  2340 cagacccct gtagcgttta gcaggatggg ggccccaggt actgtggaga gcatagtcca  2400
```

```
gcctgggcat tgtctccta gcagcctaca ctggctctgc tgagctgggc ctgggtgctg    2460
aaagccagga tttggggcta ggcgggaaga tgttcgccca attgcttggg gggttgggggg   2520 gatggaaaag gggagcacct ctaggctgcc tggcagcagt gagccctggg cctgtggcta    2580
cagccaggga accccacctg gacacatggc cctgcttcta agccccccag ttaggcccaa    2640
aggaatggtc cactgagggc ctcctgctct gcctgggctg ggccagggc tttgaggaga     2700 gggtaaacat aggcccggag atggggctga cacctcgagt ggccagaata tgcccaaacc   2760
ccggcttctc ccttgtccct aggcagaggg gggtcccttc ttttgttccc tctggtcacc   2820
acaatgcttg atgccagctg ccataggaag agggtgctgg ctggccatgg tggcacacac   2880
ctgtcctccc agcactttgc agggctgagg tggaaggacc gcttaagccc aggtgttcaa   2940
ggctgctgtg agctgtgttc gagccactac actccagcct ggggacggag caaaactttg   3000
cctcaaaaca aattttaaaa agaaagaaag aaggaaagag ggtatgtttt tcacaattca   3060
tgggggcctg catggcagga gtggggacag gacacctgct gttcctggag tcgaaggaca   3120
agcccacagc ccagattccg gttctcccaa ctcaggaaga gcatgccctg ccctctgggg   3180
aggctggcct ggccccagcc ctcagctgct gaccttgagg cagagacaac ttctaagaat   3240
ttggctgcca gacccaggc ctggctgctg ctgtgtggag agggaggcgg cccgcagcag    3300
aacagccacc gcacttcctc ctcagcttcc tctggtgcgg ccctgccctc tcttctctgg   3360
acccttttac aactgaacgc atctgggctt cgtggtttcc tgttttcagc gaaatttact   3420
ctctacaggg cctaatggag tgcccagggc ctggaaggc attggtgagc ttcactggga   3480
ctagattctc caaagcctgg agtatgaagg gtgcatgggc tgcgtccagc tacctgtgag   3540
cccctgtagg ccctcacagt ctgaaatgcc catggaggtg cctacaggtt ctcttcttaa   3600
agttgtcagg agatggggac attgcaactt gaaggcaagc ctggccctgg gtttgcttat    3660
cttggtggat ctttcttaca tctgatcttt ttacattcgg tccattcact ttggctggcc    3720
atcaccaaag acaaagacag tggccaccat ctttctcatc agtaatccaa taatgaggtt   3780
gctctgctac ttaccaagcc aagcaagccc attcctttag cctttctgcg taggatctta   3840
tttcccatgg ggacctgggg tcaaaccctg cctctgctgt tcactcatca tgggaacaca   3900
aacacacact tcccctttgt ctgtgcaatg gacaggttgg gtgacgtggt ctcagtgagg   3960
ctgaccaccc tcctctgaag gttaattcca tgatggtgtt tccctagctt cagtcatttg   4020
cttatcacct ttgtgatctc tgcagtgtct gcctttcata atatttactt attttttct    4080 ttaaatctac tcattctttt atttgagtat gtagatcttt aaaaggaaac tttttatcgc   4140
tgtcattagt ggaaagccag tatcacttgt cataaataga acaaaaccat aaaagaacgt   4200
aacaggaaaa ccatataagg gtattgaatt ctagttggaa actttagcct gggaaggctc   4260
ggagtctgaa aactgctgct ttcccttgca aaaattaaa ataaaataaa atttaaaaag    4320
aaaaggagat tagcaagtga gagaaagatg ttttagagac atattagcat caaactgaga   4380 cttttctcttt gatgtaatca ggactgaaat aattgtaaag ggataaccct cttctatata   4440
tgattcaatg ttatttaatg taaaaccaaa agtaaaacta tgtggtagac gtggccaggc   4500
aagctgggct ttcattggtc atgacatttg tccgtcttca agaaggaggt ggggcctcca   4560
gtcagtcccc agctacctct attctctaga gagtagtcag atggcaccag acctccagag   4620
gctgactacc tggggttcaga tcctgacacc atcacttatt agttgtgagg ctgtgggcaa   4680
gatactaatc tctctgtgct tccgttttct catctgtaaa atggagatga tactagtacc   4740
```

```
tacctcatag ggtggaagga ttacataaac taatctatgt aaaagtgttt agaatgaggc   4800
cgagcacagt ggctcatgcc tgtaatccca gcactttggg aggctgaggt gggaggatct   4860
cttgaagcca ggagtttcaa gccaggggac cagcctggac aacataacga acccccatca   4920
ctacgaaaaa tttaaaaatt agctgggcat agtggcatgt gtctgtagtc ctagttggga   4980
ggcaggggtg ggaggataac ttgagcccat gagttcgagg ttacagtggg ctatgatctc   5040
attgtcactg cattccagcc tgagtgaaga gcaagaccct agctcactaa agaaaaccaa   5100
ccaaacggcc aggcacagtg gctcactcct gtaatcccag cacttgggga ggacgaggcg   5160
ggtggatcac atgaggtcag gagttcaaga ccagcctggc caacgtggtg aaaccccgtc   5220
tctactaaaa atacaaaaat tagccaggcg tggtggcggg tgcctgtagt cccagctact   5280
cgggaggctg aggcaggaga gttgcttcaa cctgggaggc ggaggttgca gtgagctgag   5340
attgcaccac tgaactccag cctgggcaac agagcgagac tccatctcaa acaacaacaa   5400
caacaacaac agcaacaaag ccaaccaaac aaacaagcac ttagaatgat gcctggcaca   5460
gagtagtagg gggcaaaaag acttgagctg gaccctgagg acgtcttcac agcatagaag   5520
cgtgagggtg gctggctgga gccgggagcc tgagctgcac acagtcctcc tccaaaaggg   5580
cctggggagt ctgggagggg ttcatccaca gaagcatcca cgggccggga cctctggcca   5640
gctgcctagg ccctccccgg ggaggcatgc tagcctccag ctccagcccc ggatgcacgg   5700
aggctttccc aaggtgctgg aagtgccgct tccttcaata gagcctggct tcccttccc    5760 agcccccttg gtctgatgtg aatggacact tcctgcgggg gcaggtatca ataaacacat   5820
ctgagatgcc ctttgtcctc actggccaga aagccccagg gcagacttgc tggcttcagg   5880
ccctgagcct atgccttgtg acgcttcctt tcttagcctt ggcagcccca gtcctgattg   5940
atccatgcct ctgtttccct ctgcatcttg ataaagacag aacatagtct tttcctacag   6000
ccccagcccc agcctgtgga ccatcctggg ggatggggcc tggcggggag ctggaaccag   6060
gtcccattct ctttgggatg tcctgtgaga ccaaggacgg gacctttgc atctagtgca    6120 gggccagcca cagcaggcaa ttaataactg tttacttgac aacctctagc agctggtcag   6180
agttcagctg tttgggtggg gcttcctagg cccgactaac caagcttggg tcccacctcc   6240
aaaggctagg gcgttgcctt ggcgactgtg ggctaagctc acgccccgtc atgaaaaata   6300
cacaggcctg tccacaccca cacacaccca tcccgtgcac actcacaggg gtcacccggg   6360
gcctgctggg tggagagagg tgaaggtcac aaaaactggc attctgagaa gatgccaaca   6420
agagctcctt tcccttgtac tgggacagaa acatctgagg gtgccacagc tagaaatctc   6480
aggcacaggt ccaggcccaa gttctgagca gatgcccctg atggaactct gcatccccac   6540
agcctccctg cctgggcctg gcccatgtta ggaccttggt aaatatttgt ggaatgaaag   6600
aatgatgttt tcagcttggg tctgaggcag agcaggaatg ttgcacggag ggcgtggagg   6660
tcaatgcacg gtcagttcat ttttttctaaa tagctgaagg atgaggcatc agccccgcct   6720
gcccactgga gggttctgga gaggtgggtg gctcttcctg tctgcagtgc tggcctgtcc   6780
aaggtgtgaa tctcagctca gtcacacagc gctgtgtggc cttgggcaag tcacttctct   6840
gagtctgttt cctcatcttt aaaatgggga tgataccacc catgttgggg gtgttatgag   6900
aactaaatgt gacaggtata agatgctcag caagagccta gcacataata catggtcata   6960
agacagctct tccctcctgc ccacaggatt ttagagctgg cagccctcag gttaagatga   7020
agaaacggag gctcagagaa gcgtgggatc tgcccaaggg cacacaatga gggcacaact   7080
aagtggacac tgaggcccca ggacgttgca atccaagcga gagttttact cctgagactc   7140
```

```
aggctttccc aggttcacgg cactcttcct ctaggtggcc ctgcctcctt acctggtggc    7200
aggtggcggg tggcgggcgg ggggcctggg tcttgacagc agcacggcaa ctggacggtt    7260
cccgcctggc acatgctcag gcccaggccc cgggtcattt tcctgtccca catgcttttg    7320
gccaccctgg agccaggggc tttcctcccc acccactttt cccggtctcc gacaatgacc    7380
caggtgtcca aaaggatctg ctcctgacaa taagcaacat cctctcgcca aagaattgta    7440
attttagccg ggctgcacag cttccctgac aacacacagg catgtgcaca gatgtggagt    7500
ccgcggggca cgtgcaggcc cctctgcgtg ctgtgcgctg ccctctcccc ccatgccatg    7560
ccttcgagtg tcctcctaac gacaggctgc tgtgggcctt gtcccagctg gagtctcaga    7620
cacagtaaat ggggtgtttt ctggccttcc ctccctcccc aggacaaacc cctgtggacc    7680
cttggtttgt cctgtccctc tggcttgtcc tggaccctct cctgtctggc cctcttgctt    7740
gaaaactgaa catcctcccc tgctccccaa acttgaatcc taagacagct ttttctaaa    7800
aggggaacaa ctcctttggg acctgtggga tgggtggcca gtgtgtgagg ggtggggagg    7860
tgtgggggat tgagcaatgc cccctctccc gtactccctg aactctgctt tctctctgat    7920
gcacccaccc gccgtgcatc tcaaggaagt tgcctccagg ggagaacatc ccttccctac    7980
tgctgcgggt gctatgggta caatcctggg gtcattaacc ccattgctta gaccctgagg    8040
gctcccagcc tggtgccctg ccccaccttg ttcacaggga cactcaggcc aacaaccacg    8100
ctagccccac ttgtccacac ctctgtccac ttgagggccc ccaaccccac ccagctcagc    8160
tttgcgcatc ttgctttggc tgccagctct actctgcctg ccctgccata ccctcctctg    8220
gcctgcagcc ccgtgtctgc tgagccagcc cttcggccag cccccaaggt atgtgtgctg    8280
gtggtaaata ctaccgtagc tgaagctgga gctgaattca gctcccagcc ctggggtggc    8340
tctggggtag gaggtgatgt caggcaaagg gagaaagggg cagaagctgg gagaggtgct    8400
ggtgggacct gccacatggc ctgctgggga aggggcagc acagggcccc cttggggcag    8460
gttttgtttc ttcctgggag tacgtgggag agcccttttcc ctaggtcctc ctcacttctg    8520
tttcccggca gagccatagt tttgcagcta caccccacccc actcaggtgt aaggggaag    8580
tccaggccag cacggacaaa accaggggca cagccaagct tcctggggct ccttttccac    8640
tgagcctgct gcaggggtaa gggcagtggg ttagcagagg agagttggct agtcccgtca    8700
ctgccaggct ttccctgggg accctgggtg gatcatctcc tctcttgagt ctgtgggtca    8760
gatttgtagc ataatgggtt tgggcagtag agtcccatgc cagctagccc aagaagccac    8820
actcattcat cacaaactca aatgtccaca ggaccaagaa accacggtga gagagtgaag    8880
caggccaggt ggaattatta gggagtagta cggacggact ctggcgaact ggagtgccgg    8940
tgcccccaa aagctgctac tgagccccag ctgacagttg ccctgtggga aagctggttt    9000
agcattatct tctgatttc taaggagagc tggaagtcag aattttcatg tcaaattcct    9060
ggttttaaa tgttgccatc tcaagaaaat taaaaagatt ttgaggatcc aatgaaatat    9120
gtgtgaaggc tggatgtggc ctgtgggctc ccagtttctg gccttttttt tcatcagtat    9180
agtgtctatg tgtctgagtt taattctagc tctagcactt gcttgctgtg tgatcatcag    9240
tgagttacgt aagttctctg tgccttagtt tcttcatcag tgcaatggga ataaaaacaa    9300
taccttatgg cattgttaga tatgcccatg aaacccttag cgtagtgcac aacacatgct    9360
gtgtcttctt attacggttc tgcctagatc ctgcgttacc tgaagtcccc catgctccag    9420
gctttgagat catacctct ggaactttgg aacttcagtc caaccactt ccctttctgg     9480
```

```
gtctctgtgt ttctgcctga aaaggagacc tgtatcttgc caaagaagtt ctgaaatctc   9540
tgctcaccct gacaatgact ccaaaaatct ggggctccca gacttggctc tctgcctaaa   9600
actccactct tgcagacatg ccgtttgggg ctttggtgcc tttggagact ctcctttaaa   9660
cacaagcgcc ccaggatcgg atcacaagtt gttatcagtc attcacacct tagcaggaaa   9720
gactttaaag ctggcttctc catcccactg tgcttctcac tcctaggagg cacttcttga   9780
cttgctgaat gaattagaga cctgtctagc tcccaagtac caagcgccga ctactcgcat   9840
ggcacttaca gaacacttca tgtgaattat tactaaccgt tgcctcaact ctgccaggga   9900
gatgttttca tttctgggaa aaacatctgt gagtgaggag tcggggctca gcgtctaagt   9960
ggctcacagc tactggtcca gtacaggctg gccagctcca gaagcccac caggctgcct  10020 ccctcctggc tgggcaaggc tttcagctct tccagtgggt cccagcctgc cgccgagggt  10080
cctgggctct aagggcaggg aagggcatc tgaaggagga tgtggcatta tattggttct  10140
gggcaatgcc cctggctggg gcaatgaaaa ggatgtatca gtttggattc tgtacatagt  10200
tctaaccctc cttccctctc tgctagaccc acaacagcct gacatgccat ttaaaataaa  10260
aataccactg gccgggcgta gtgggtcaca cttgtaatcc caagactttg agaggccaag  10320
gcaggagaat tgcttgaagc caggagttca aggtcagcct gggcaacaga gggagactcc  10380
gtctcaaaaa caaataaata aataaaaata acaccaacgc ataataatta tagctatccc  10440
tcagatgtct gcagagggca ttagagctca catcttgtgt tctcatcttt ccctcatcta  10500
gtccttttgc aaccctgcat tgtagccaat agttttctca ctgcacagag gaggaaactg  10560
aggctcatac agttagatag aaacgcggcc tctatccaat attctgtttt caaaagctca  10620
tggttttgag ggtcaaccca attaaatgct ggaggattgg gataaggcaa agtggaccag  10680
ggaattgctt catttgcttg gtgaaaaaaa ccaaacagaa ctagacagtt ttctaagttt  10740
ggctggaagg acgtgcatgg atgagatgac ctttcatata ctctctgtcc cggtccctca  10800
gacactgggt tttcccattt tcacactatc ttgcctagga cacccttct actggctgaa  10860 atcctatcta tgcaccaagt ccaaagactc tccctccttc aggaagtccc tgactgtccc  10920
cagaaggctg tttcctccct cctccaagtg ccctgagggc tggcattgga ttgcctttgc  10980
catggggttc tgctgtcggg aatgcaggcc tcgtctgctc aaggggaggc catgcattca  11040
gcatgcaggt gagatgcagc acctggccca ggccttgcac acgcaggtgc tctcttagtg  11100
ctccctggca aggatgggaa ggcatgttca gtcctaggag taggaagggg cagaggtgtt  11160
gatggcccct acagagcggc caaggacaag gagctgctgt tcgaaacagc cttcctgctc  11220
cccaacctgc ctcccaccca acaggttttg catatactct actgggaaga gggacacacc  11280
cgactgcatc actgccctcc aagtctctcc ctgccctgtc cagcatccag gagcacccct  11340
agttggggaa gcttctgtga ctcccctac aacagcctag gatggagtgg ggtttgtgaa  11400
caaatgcaga aggcagtctt agggaggtca gctgacatgc cctggcctg tggctgggaa  11460 gtagcagagg ctaaggttct tccccgctct ggggttgcca ggagtagcac tggatcagtc  11520
aggtgacagg gctctcctct ctctgagcag gtccggtggc agccttcaag gtcgccacgc  11580
cgtattccct gtatgtctgt cccgagggc agaacgtcac cctcacctgc aggctcttgg  11640
gccctgtgga caaagggcac gatgtgacct tctacaagac gtggtaccgc agctcgaggc  11700
gcgaggtgca gacctgctca gagcgccggc ccatccgcaa cctcacgttc caggaccttc  11760
acctgcacca tggaggccac caggctgcca acaccagccc cgacctggct cagcgccacg  11820
ggctggagtc ggcctccgac caccatggca acttctccat caccatgcgc aacctgaccc  11880
```

```
tgctggatag cggcctctac tgctgcctgg tggtggagat caggcaccac cactcggagc    11940
acagggtcca tggtgccatg gagctgcagg tgcagacagg tgagggcatc ctgcacgtga    12000
cagcctggcg tgtgtggagg gctgcctgtc tgatggtgtg accattcatg acactgtgct    12060
gggcagagtg tgaggctgca tgggtaacac tggcactcca gggagtgtgt gggtgagatg    12120
gggtggtcaa gggtgtgtgg agtgtgggtt tgtagttagc tggagtgatg gagagggagg    12180
gtgtacctgg ctccatttgt gacagtgaga cttttaatg tgtgaggctg taggtacctg    12240
ggctgggagt gtgactgctc atgatgacat catggctgct gtgggtatag gcatcagtgg    12300
gactgattgg tgccctgggg catgactcag tggatggctg aatggctgtt ggagaatata    12360
tgcgtgtgtg tgtctgtctg ttcaggtgag agtgcaaggg cccatggttc ggatagaggt    12420
gtgggcacca gcgggtattc acatgcccct gggagtggca tgaaaatggg cagggtgaga    12480
acatgccagg gtgtgtgtgg gtgcaaacgt gtgcaggctg ccactgggcc aacactgccg    12540
agtaggcact agcgtgagaa cctggggcag gagggggaca ctggcctgga caagcctccc    12600
tggcctcctg ggcctgacac ccacctaatg gcccttctgt ttgttcccac aggcaaagat    12660
gcaccatcca actgtgtggt gtacccatcc tcctcccagg agagtgaaag taagggacca    12720
acctcttgcc ccttttgggt tctctgtttt cttctgtcct catcctgcac ccagaccctg    12780
tttggaactc tggcctcatc accccaagcc ctcagaaccc cccggtcctc ctccttttct    12840
gctgctgcac atcccttctg cttcctcctt ggtgcaatcc ccagaagccc actctccttc    12900
catctgctct ggagtctctg ctcctcttga ctctctggag tgactgtgcc ttggcagtga    12960
cctttggcca gggcaagtgc ctcatgacag gtactgggtg ccccaggcag ctaagtgccg    13020
ccctgcccac cagcccccta tggcttggga aggctggggg tcctcttggc ctagaattaa    13080
actacttcag atttctgtgt tctgtgtttc tatgttcttc agatgttctc tgttgcaggg    13140
gagggaggag gaagaggttc aggaagggga acagaactac ctttcctgag ttcc          13194

<210> SEQ ID NO 4
<211> LENGTH: 11997
<212> TYPE: DNA
<213> ORGANISM: Homo sapiens
<220> FEATURE:
<221> NAME/KEY: exon
<222> LOCATION: (4088)..(4195)
<220> FEATURE:
<221> NAME/KEY: exon
<222> LOCATION: (6551)..(6578)
<220> FEATURE:
<221> NAME/KEY: exon
<222> LOCATION: (7692)..(7885)
<220> FEATURE:
<221> NAME/KEY: exon
<222> LOCATION: (8263)..(9241)
<223> OTHER INFORMATION: Nucleotides 8301-9241 are an untranslated
      region.

<400> SEQUENCE: 4
tttttccttc ttggttgtaa ggagccagag agaaaacgat tgagcagtgt tctcaagaca      60
acttccctgt cagtaaaaca ccaaaaagga ggccaaatgt ggtggctcat gcctataatc     120
ccaacacttt gggaggccag gtgggcctga ggtcaggagc tcgagagcag tctgggcaac     180
cgtctctact aaaaatgcaa acaattagc tgagtggcca ggcacggtgg ctcacaccta     240
gaatcccagc actttgggag gccaaggcag gcgtatcatc tgaggtcaga agtttgagac     300
cagcctggct aacagggtga aaccccattt ctataaaaat acaaaaaaat tagccaggca     360
```

```
tggtggtgca cgcctgtagt cccagctact caagaggctg aggcaagaga atcgcttgaa    420
cccgggagtc agaggttaca gtgagccgag atcgcgccac tgcactccag cctgctgata    480
gagcaagact ccatctcaaa aaaaaaacaa cccaaaattt gcctggcatg gtggcaggca    540
tctgtaatcc cagctactcg ggaggctgag acatgagagc tgcttgaacc tgggaggcag    600
aagttgcagt gagccgagat cacaccactg cactccagcc tgggtgacag agcgagactc    660
tgtcccaaaa aatcaaaaaa atcacttttg gtagagatgc actctcgcta tgttgcccag    720
gctggtcttg aactcctggg ctcaattgat cttcccacct tgacctccaa agtgctggga    780
ttacaggtgt gagccaccat gcctagcctc agggaattct tataagaact ctatgaagta    840
ggcatcacca tcttctctgt atccatggaa agagaggcct agagatgtat gctaacttgc    900
ccaagctcac atagcccagg gtagcatagc tgggatctgg ctgcaggcct gcttagctct    960
gcatactcac cttcttccca gcttgggggca gtgcagtggg tagcagttag cccccggtg    1020
cttgccagag aggtgcccta cagggtaaga gggcactgcc ctaagggtgc ctggcgctga   1080
gaggttgggt gagaataccc agcagcttgg agacaaaatg caagggcacc tccctcttct   1140
gagaagaggt cttggcttcc acacccctct atacctgta tgtgtcagac atccagtggg    1200
gaccagcccc tgctaggccc tggagataca aaggcatcca ggaggacatg cacgaggacc   1260
taagccggaa tggggatcag ctaaaccacg gacccaacaa acccaactc aaaggctaca    1320
gtgactttt actcagctac cctttttca aaccaacaaa caggccaaga gcaaaattag     1380
aacatgcatt ttggtcagag ccatgttggt caggctggtc tcgaactcct gggctcaagt   1440
gatctacccg ccttggctcc ccaaagtgct gggattacag gattgagcca ctatgcccag   1500
ccccagtgcc agcctcttaa tgttatcctt gggaagtaag agtgtagctt gactatgaaa    1560
taacatgaaa gtacaagtta acctgaggta ggggaatgag actagagaag ttggtgccca   1620
aggagctcct gcattgctga ggggctgtgg tttctcagtg agctcagaga aggggtctag   1680
gcagctcatc tccctttgaa cttcttccca ccccccagcg cagcagaatg tgctgtctgc   1740
tttcacccag cttcctccct gggaaaccag gcagcccaac cctcagcagc cgaactccct   1800
cctccatata tccccgtggg ctaccaggca ggccctggac aaaggccgcc tgagcaggcc   1860
aggcccctcc catcccaccc tgctgtgtca gggcctggca cactccttag tgcggtgtcg   1920
gcagctacct ctgccagcgc ctgatcacct tcccaggata agcctggctc tggatggtga   1980
gtgagtatgc ctgccttccc ctgtgagtgc cagcccaggc actggccacg cttgggggaa   2040
ggggtgggga actgtggcga ggctgagctc tgcagagatg cctacggctt cagaaagcag   2100
ctggatccac agacttgtcc ccaaacctct gcgcccctct gccccagcct caactcagcc   2160
cagatcgtaa ggaagcctca ggctctcaaa gtgaaattaa gtcctgatct gatagagggt   2220
ccacataggg gaaatctcta cctggggata gaagttaggc agggatatct ggccaagctc   2280
accctccaaa ggcagatagg gaacaggtat caatgagcac ctggcaaagc tcacaaaatg   2340
ttgcttacta gccgtccaga ggagacctgc tttgatcact agaagagagt gctttgcaac   2400
tggcttctca aatattgccc acaataaggt cctttgatgg gggttttgaa atactgaggt   2460
gtctgggtta tagaatgtct ttactttcaa tattccacgt caaaatgcag ccttgctaag   2520
atctgcaggg aacctgctgt aatgtggagc ggaacttgct ttgtaattag catagcaact   2580
gttcctgtac cagtgggtac ttctaaagtg actgaaaaca gtttgttctc atttgcagta   2640
tgaacaaacc tcctgaaagc ttgtttacgc tgtcggattg tagagcaaaa caaaaacagc   2700
ctttattccc aaacaaatag cggaaaggca acatttagac cacagccatt tacctctcag   2760
```

```
agctctttgg ggcgaagttg acactgtgac aaggtatccc agcccatctt ttggccctgg    2820
gaaaggctaa aattgggaag gaaatgcgtt tatgttggtt gtggttctga gggcacgtct    2880
gttcccagct aaactcctgc agtcagcaga tgccctgaaa taaatcaaac ctcctcatgc    2940
tgttgggaca gcgaagcttc gtgtacacct ttttggaggg caatttagca atagcctaaa    3000
agaaaatgca catactcttt ggctcagcac tttgaccgct aggaatttac tacagatttc    3060
cttgctgagt gagccaggct gcgtgcacaa gttcattgct acattattag ttatgctgaa    3120
aatggaaaca acatgtctac caacagggga ctgcttcaat aaatttagtg ggagccatgt    3180
gataaaactc taagcagaat gaggcagggg agacagagag atgtccaagc tgtgctcagt    3240
gggaaaagca ttgtcatatg atgctgcgtc tgctgtattt gcagggaata taactaggac    3300
cataacacaa aaaccggcac acagggatga tctcttcaga gggggtcttg gtacaagggg    3360
aggaggagat tcgaatattt tttaaacttg tacttttttt ggtagtttaa taagtttaaa    3420
atggaaaaac attgtacaag gattcacgtt tttctagttc tcaccccggg tgtttctcct    3480
gtgacttgtg tggtgagatc aagggggttct agaggcccca tcccagagct aaggagtctc    3540
tgggatgagt tggggctttt tatctattat gataaaacat atataatgta aaatttgcca    3600
tttcaaccat tttaagccta cagtttggtg gcattaatta cattcacaat gtgcaaccgt    3660
caccactgtc tattttcaaa actttcatca cttaggcttc ttttgacctt gagctctgtg    3720
gcatggggtc tgcgaaggcc ctgctctccc ttttcagaga acaacctgta gccaagggtg    3780
ttccagctgt accttgtggg ctgggatgag gactctgttc cctctcttgc ctggagctgc    3840
ctgagctgta ggtgacaggt cttgtttctg agtgctccag gggcataggg cggcaggcac    3900
agggctctct ttgaaaggag aaccgcctta tcttccatgc ctctgtaggt tgctgggggt    3960
ctagctgtgg gactctgggg aaaggcgggt ctcctgcttc ctggccttcc ctctctgagc    4020
ctcagtttat gctcaggagg agcaatggga atggggcttc accttggcta cctctctgcc    4080 cttcagaca tcacggctgc agccctggct acgggtgcct gcatcgtagg aatcctctgc    4140 ctcccctca tcctgctcct ggtctacaag caaaggcagg cagcctccaa ccgccgtgag    4200
tattcctacc tgcctggggt gggtggacgg tgcgagtgac ctgctccagc ccccagttca    4260
gcccctggga ttcgcaaagg cacgatgcag gcacaattcc ttttcatttg agagttggga    4320
gcagctgcac ttcccgccag gagctgggcg aaatggccga gagaaggag gcatgccatt    4380 tccgggggcc aagtgcccac cagccccttt ggctcccagg cagtgctggc tcggcactca    4440
atacatgtct tctgaatgaa tgatcatatg cagtagctca agttgcttta taaaagcaag    4500
ttgctgccac tcagagatcc ttgggggacc tgtttaaggt atgggcgtgc ttgttttgta    4560
attagtagca attgttggga caaaaaatga tctttggaat atcagaagtg aagggggtct    4620
tacagacaac ttagctcaac ccttctttt tccagatgag aaggctaaga tcagtggggt    4680
tacataactg actgaatgtt acgtaactta gtaagtggca gagctaggac tcaatctcag    4740
agctttcaac gcatgctctt tccagggaat agaagtccac catataataa aaatgctctc    4800
acttactcct cattgcaagt ccaagaattt ggtcctacca ttgtccccat tttactgatg    4860
ggcaaacgga ggcacagagg ggttaagtaa cttgcctaag gaaccacaca gcaaataagt    4920
ggtggggctg ggctttaagt catgggcaca aacatctttc acctcccacc ctggccaggt    4980
gacagtgccc cttgcctagt tcctgaccct gccttgagt cttggttagt ctgagtcctc    5040
caagaagggg ctagggagtt ttttaccctt gcctcccctc cctggcctct tcccgtctgc    5100
```

```
ctggctacag aggtaactga gaaaggattg ctctggtgcc aggtggcttt tggctcgcaa    5160
cttatttcct gtggccggcc cttaacaact tgtcatccct ccctcccctc attcccgggg    5220
gcccccacgt gaagcccat  agtgggtcac tcggggctg  tggccacctc acccttgctt    5280
tcagaactcc cctattcctc tcctagaaca caccacaacc tacctgcagg aatacccatg    5340
gctgggggtg ggtgggggca ggtaaagggc ttggaacaga agagcaacgc tgggcagcag    5400
ggcaggggga gcaggtgttg ctgtgccctc cctggtggaa ggctggccca gagagcctgc    5460
tcaggaatga ggcactctca ggaaaaaaag aaaggaaag  ggctgggagc cttgaggacg    5520
gcagtttgct ggagaggcca acaggtgtgg atttccatcc tgctttggac tgagcctcag    5580
tttccccagc tctaaaatgg gaccaacaac cctcacccca aagggtggca cagaggatga    5640
gatgagggaa tacccgtgtg cacctgcacg aagcctgacc catgagtcgg ctgtaagcaa    5700
tagccatggt ttgaatagat ttcaggaact tttgggtaac ttccctgtgt ttgttctgtt    5760
gttgtgcccc tcccccacca tctgtttccc catcgtaatc agcagtaaat ctccttaaaa    5820
cgagaagcat ctgtgggagg acatggggtg ctgcatgaaa gagggaagtt ggggtcactg    5880
catctaattg gtgccagtt  tggggggtgg ggtgtcccaa ggctgaggca agcggcagca    5940
acttggatga gaagcagaaa gtgagtgaag tggctgggaa gtgatcgggg acttgcacct    6000
tgtaaggttt ccctgagaga tgtccctag  aatgccaccc tattaggcaa tgtaggggat    6060
aggacagaga ggaccaggag ccctctaatt aggaactgac cttaaacact cccacccagt    6120
aagtcatggc taaagaccag aacctggcaa atgttcaaac aagagacacc agttagcaaa    6180
ttcaagagtt gacctttgct cgatacttaa atcctgaagg tctgacactg tgtaagtcaa    6240
gccataggag aaaagcgctgg ctgcctttgg tctcctgatg gcagatagcg ttcttcacact    6300 cctggaaaat gcagatagag tttcatttat cagtcgtcaa aatgggcccc tcatggaggc    6360
cccatctgct ggacagacac gcagatcgct gctggacagc acccatgtga aaagaaatgg    6420
agtccggagc tgtgcagggc cctcctgggc tcgctcctgt tccctgcagg gcatctgcca    6480
gcaggggcag ggatgttgta tggggaagcc ttcccttcca tgaccagctt ctctgtctgt    6540
ctgtccctag gtgcccagga gctggtgcgg atggacaggt aaggcccatg gagaccttct    6600
tgagaaaact tcctgggccg gctatccagg aagagatact tctgtgcagt aggggccctg    6660
tttagctgcc tagagcagct ggtcagaaga gcctctgcca tctgctgctg aagcctgcac    6720
atctgtgcag attggctgtt ctcctgccac cccgactcag caggctgagc tctgattctg    6780
ctcagatgtg tcatgcaccc accttcgggt ctcagtggtc agcctgggcc aggatgggga    6840
cagggaggaa gcactgtctg gggcagacag tgagacatgc aaaggaggcc agcgggccca    6900
gccccagcca cagcccttga gctgtgcctc ctgcccgcag agaactccaa ggagaaagct    6960
gttaggccgc tgcaggccac aagggcagag gctgaggggt cccagagtgg tgcagtgggc    7020
tgggtctagg ggcagagggg atggggactg tgtattggtg tgctctgggc aggaagctgc    7080
catgcagcct ggcctggagg gtgtgttcag ggaacccaag ttcctgcccc ggtacctgca    7140
acaccaaaca caaagctcct ctaggtgttt gaaaggatg  atcttcaaga caggttgaag    7200
gaagtcctgc ttgcaactca tctagaatct aagagttgca ggggtcttca gaagttatcc    7260
cactcccaac tgggaagaga agagaacccc tcccctcagc tcaagacagg ctttggggat    7320
gttcgatcct aatgccatca actctattga ccaaagagaa acttgtcccc aaattcctga    7380
ggctgaagtt ctagaagtgt ctgtgatttt tggcttcctg gctgtgcccg gggttgatgg    7440
tcagaccaca gggaggagct ggggtctgtt ctggtgggcc ctgatgccct cagctcagga    7500
```

```
caggtgggca ggtgcagccc atggcctttg ctctgtgggc ctggctcctg ccttcttgct   7560
tggagatgct gctgaggctt ggggatgggg atgtaggtga gagaaaggga ggagagaaaa   7620
actgggggca gggagggcag agttcacgct ccggacagca cagatgacct tccattctgg   7680
ttctgtggca gcaacattca agggattgaa acccccggct ttgaagcctc accacctgcc   7740 cagggggatac ccgaggccaa agtcaggcac cccctgtcct atgtggccca gcggcagcct  7800
tctgagtctg ggcggcatct gctttcggag cccagcaccc ccctgtctcc tccaggcccc   7860
ggagacgtct tcttcccatc cctgggtaag tgtttcctga ccttcacagc acgatgacct   7920
gtaaggtcat gacctcatgg cctgcagggc atcggcctca ctccctgccc tccctgaaga   7980
gttccacggc ctcacggggt gggggttgagg gtgagggaca gaggggcccc cattcacctc   8040
cctgaagagt tccacggcct cacggggtgg ggttgagggt gagggacaga ggggccccca   8100
ttcacctccc tgaagagttc cacggcctca cgggtgggg ttgagggtga gggacagagg   8160 ggccccatt cacctccctg aagagttcca cggcctcacg gggtggggtt gagggtgagg   8220
ggcagagggg ccccgttcac tttgcttctc cttttcttgc agaccctgtc cctgactctc   8280
caaactttga ggtcatctag cccagctggg ggacagtggg ctgttgtggc tgggtctggg   8340
gcaggtgcat ttgagccagg gctggctctg tgagtggcct ccttggcctc ggccctggtt   8400
ccctccctcc tgctctgggc tcagatactg tgacatccca gaagcccagc ccctcaaccc   8460
ctctggatgc tacatgggga tgctggacgg ctcagcccct gttccaagga ttttggggtg   8520
ctgagattct cccctagaga cctgaaattc accagctaca gatgccaaat gacttacatc   8580
ttaagaagtc tcagaacgtc cagcccttca gcagctctcg ttctgagaca tgagccttgg   8640
gatgtggcag catcagtggg acaagatgga cactgggcca ccctcccagg caccagacac   8700
agggcacggt ggagagactt ctccccgtg gccgccttgg ctccccgtt ttgcccgagg    8760 ctgctcttct gtcagacttc ctctttgtac cacagtggcc ctggggccag gcctgcctgc   8820
ccactggcca tcgccacctt ccccagctgc ctcctaccag cagtttctct gaagatctgt   8880
caacaggtta agtcaatctg ggcttccac tgcctgcatt ccagtcccca gagcttggtg    8940
gtcccgaaac gggaagtaca tattgggggca tggtggcctc cgtgagcaaa tggtgtcttg   9000
ggcaatctga ggccaggaca gatgttgccc caccccactgg agatggtgct gagggaggtg   9060
ggtggggcct tctgggaagg tgagtggaga gggcacctg ccccccgccc tccccatccc    9120
ctactcccac tgctcagcgc gggccattgc aagggtgcca cacaatgtct tgtccaccct   9180
gggacacttc tgagtatgaa gcgggatgct attaaaaact acatggggaa acaggtgcaa   9240
accctgagaa tggattgtaa gagccagttt aaatctgcac tctgctgctc ctcccccacc   9300
cccaccttcc actccataca atctgggcct ggtggagtct tcgcttcaga gccattcggc   9360
caggtgcggt tgatgttccc atctcctgct tgtgggcatg ccctggcttt gtttttatac   9420
acataggcaa ggtgagtcct ctgtggaatt gtgattgaag gattttaaag caggggagga   9480
gagtaggggg catctctgta cactctgggg gtaaaacagg gaaggcagtg cctgagcatg   9540
gggacaggtg aggtggggct gggcagaccc cctgtagcgt ttagcaggat gggggcccca   9600
ggtactgtgg agagcatagt ccagcctggg catttgtctc ctagcagcct acactggctc   9660
tgctgagctg ggcctgggtg ctgaaagcca ggatttgggg ctaggcggga agatgttcgc   9720
ccaattgctt gggggttgg ggggatggaa aaggggagca cctctaggct gcctggcagc    9780
agtgagccct gggcctgtgg ctacagccag ggaaccccac ctggacacat ggccctgctt   9840
```

-continued

```
ctaagccccc cagttaggcc caaaggaatg gtccactgag ggcctcctgc tctgcctggg    9900
ctgggccagg ggctttgagg agagggtaaa cataggcccg agatggggc tgacacctcg    9960
agtggccaga atatgcccaa acccccggctt ctcccttgtc cctaggcaga ggggggtccc   10020
ttcttttgtt ccctctggtc accacaatgc ttgatgccag ctgccatagg aagagggtgc   10080
tggctggcca tggtggcaca cacctgtcct cccagcactt tgcagggctg aggtggaagg   10140
accgcttaag cccaggtgtt caaggctgct gtgagctgtg ttcgagccac tacactccag   10200
cctggggacg gagcaaaact ttgcctcaaa acaaattta aaagaaaga agaaggaaa     10260
gagggtatgt ttttcacaat tcatgggggc ctgcatggca ggagtgggga caggacacct   10320
gctgttcctg gagtcgaagg acaagcccac agcccagatt ccggttctcc caactcagga   10380
agagcatgcc ctgccctctg ggaggctgg cctggcccca gccctcagct gctgaccttg   10440
aggcagagac aacttctaag aatttggctg ccagacccca ggcctggctg ctgctgtgtg   10500
gagagggagg cggcccgcgg cagaacagcc accgcacttc ctcctcagct tcctctggtg   10560
cggccctgcc ctctcttctc tggacccttt tacaactgaa cgcatctggg cttcgtggtt   10620
tcctgttttc agcgaaattt actctgagct cccagttcca tcttcatcca tggccacagg   10680
ccctgcctac aacgcactag ggacgtccct ccctgctgct gctggggagg gcaggctgc    10740
tggagccgcc ctctgagttg cccgggatgg tagtgcctct gatgccagcc ctggtggctg   10800
tgggctgggg tgcatgggag agctgggtgc gagaacatgg cgcctccagg gggcgggagg   10860
agcactaggg gctggggcag gaggctcctg gagcgctgga ttcgtggcac agtctgaggc   10920
cctgagaggg aaatccatgc ttttaagaac taattcattg ttaggagatc aatcaggaat   10980
taggggccat cttacctatc tcctgacatt cacagtttaa tagagacttc ctgccttat    11040
tccctcccag ggagaggctg aaggaatgga attgaaagca ccatttggag ggttttgctg   11100
acacagcggg gactgctcag cactccctaa aaacacacca tggaggccac tggtgactgc   11160
tggtgggcag gctggccctg cctggggag tccgtggcga tgggcgctgg ggtggaggtg    11220
caggagcccc aggacctgct tttcaaaaga cttctgcctg accagagctc ccactacatg   11280
cagtggccca gggcagaggg gctgatacat ggcctttttc aggggtgct cctcgcgggg    11340
tggacttggg agtgtgcagt gggacagggg gctgcagggg tcctgccacc accgagcacc   11400
aacttggccc ctgggtcct gcctcatgaa tgaggccttc cccagggctg gcctgactgt    11460
gctgggggct gggttaacgt tttctcaggg aaccacaatg cacgaaagag gaactggggt   11520
tgctaaccag gatgctggga acaaaggcct cttgaagccc agcacagcc cagctgagca    11580
tgaggcccag cccatagacg gcacaggcca cctggcccat tccctgggca ttccctgctt   11640
tgcattgctg cttctcttca ccccatggag gctatgtcac cctaactatc ctggaatgtg   11700
ttgagaggga ttctgaatga tcaatatagc ttggtgagac agtgccgaga tagatagcca   11760
tgtctgcctt gggcacggga gagggaagtg gcagcatgca tgctgtttct tggccttttc   11820
tgttagaata cttggtgctt tccaacacac tttcacatgt gttgtaactt gtttgatcca   11880
ccccctccc tgaaaatcct gggaggtttt attgctgcca tttaacacag agggcaatag   11940
aggttctgaa aggtctgtgt cttgtcaaaa caagtaaacg gtggaactac gactaaa      11997
```

<210> SEQ ID NO 5
<211> LENGTH: 21
<212> TYPE: DNA
<213> ORGANISM: Homo sapiens

<400> SEQUENCE: 5

```
aaactggctc cagcttgcct a                                              21

<210> SEQ ID NO 6
<211> LENGTH: 3023
<212> TYPE: RNA
<213> ORGANISM: Homo sapiens
<220> FEATURE:
<221> NAME/KEY: exon
<222> LOCATION: (1074)..(1207)
<223> OTHER INFORMATION: Nucleotides 1074-1126 are an untranslated
      region.
<220> FEATURE:
<221> NAME/KEY: exon
<222> LOCATION: (1208)..(1636)
<220> FEATURE:
<221> NAME/KEY: exon
<222> LOCATION: (1637)..(1694)
<220> FEATURE:
<221> NAME/KEY: exon
<222> LOCATION: (1695)..(1802)
<220> FEATURE:
<221> NAME/KEY: exon
<222> LOCATION: (1803)..(2024)
<220> FEATURE:
<221> NAME/KEY: exon
<222> LOCATION: (2025)..(3004)
<223> OTHER INFORMATION: Nucleotides 2063-3004 are an untranslated
      region.

<400> SEQUENCE: 6
gggucucaga aacaucagag agagguuugu aguuucgcuc uggagggcag aacagccgga      60
agaagaacca acugcugguu aucucaggcu ggagguggua gcugaagggg guguggacag     120
uaaggauuug ccgggaaaaa ggaagggucg ggacauuucg ugaaguggga ggacuugagc     180
ugagcccuga gggaugagaa gaauuaggag gggagagaca uuccagugguu gccagcagug     240 cuggguguguu gugcaagagc agaggcacua gaaguuaggg ugcaucagag uguccugcag     300
auauccaggc accaggagg gagggcgggu gcacagccag gcggacagcu gaggccucug       360
ccggagggga gcuugcagga ugugcugugg ggcacgccaa caggugguugc cugcauaucu     420 gugugugucc cggggguaggg augugcugau cuuggcgugu aguccugcac cguucugug      480 ugugugugug ugugugugug ugugugugug uguggcgcg cgcaugcacu caggggugcuc     540 caggcucuga aucucaguu aaacuggcuc cagcuugccu agcucuucac aaugucagau       600
uucauucauu cacucauuua cucacucauu ccacagcugg gagugccuac cacauaccaa     660
gcccuggucu ggcuggagga uguagggguac aagucucugu ccccagauca cucaaaggcu    720
gguggcugag ggcagaugca agccauggua acgucuauca cgcuguuaga gguagaucua     780
cuucuuaggc ugcgcagcaa uaauaauuuc ucuccaaaag gacuggggga cgguagaacg     840
ggcuuuaaac ugccgaucaa guggagcuga cucgcuggga cgcacgcugg cuccccaccc      900
acggggccgg ccuccgggaa gccccuccca cgccggcccuc ggagaggcag uuccccaca     960 cggccccccg ggggcgcugc gcgaagggggg cgggugccug gagcacggcg cuggggccgc   1020
ccgcagcgcu cacucgcucg cacucagucg cgggaggcuu ccccgcgccg gccgcgucec     1080 gccccgcuccc cggcaccaga aguuccucug cgcguccgac ggcgacaugg gcguccccac  1140
ggcccuggag gccggcagcu ggcgcugggg aucccugcuc uucgcucucu uccuggcugc   1200
gucccuaggu ccgguggcag ccuucaaggu cgccacgccg uauucccugu augucugucc   1260
cgaggggcag aacgucaccc ucaccugcag gcucuugggc ccuguggaca aagggcacga   1320
ugugaccuuc uacaagacgu gguaccgcag cucgaggggc gaggugcaga ccugcucaga   1380
```

| | |
|---|---|
| gcgccggccc auccgcaacc ucacguucca ggaccuucac cugcaccaug gaggccacca | 1440 |
| ggcugccaac accagccacg accuggcuca gcgccacggg cuggagucgg ccuccgacca | 1500 |
| ccauggcaac uucuccauca ccaugcgcaa ccugacccug cuggauagcg gccucuacug | 1560 |
| cugccuggug guggagauca ggcaccacca cucggagcac agggccaug ugccaugga | 1620 |
| gcugcaggug cagacaggca aagaugcacc auccaacugu guggguacc cauccuccuc | 1680 |
| ccaggagagu gaaaacauca cggcugcagc ccuggcuacg ggugccugca ucguaggaau | 1740 |
| ccucugccuc ccccucaucc ugcuccuggu cuacaagcaa aggcaggcag ccuccaaccg | 1800 |
| ccgugcccag gagcugguge ggauggacag caacauucaa gggauugaaa accccggcuu | 1860 |
| ugaagccuca ccaccugccc agggggauacc cgaggccaaa gucaggcacc cccuguccua | 1920 |
| uguggccag cggcagccuu cugagucugg gcggcaucug cuucggagc ccagcacccc | 1980 |
| ccugucuccu ccaggccccg gagacgucuu cuucccaucc cuggacccug ucccugacuc | 2040 |
| uccaaacuuu gaggucaucu agcccagcug ggggacagug ggcuguugug gcugggucug | 2100 |
| gggcagguge auuugagcca gggcuggcuc ugugaguggc cuccuuggcc ucggcccugg | 2160 |
| uuccccuccu ccugcucugg gcucagauac ugugacaucu cagaagccca gcccucaac | 2220 |
| cccucuggau gcuacauggg gaugcuggac ggcucagccc cuguccaag gauuuugggg | 2280 |
| ugcugagauu cuccccuaga gaccugaaau ucaccagcua cagaugccaa augacuuaca | 2340 |
| ucuuaagaag ucucagaacg uccagcccuu cagcagcucu cguucugaga caugagccuu | 2400 |
| gggauguggc agcaucagug ggacaagaug gacacugggc cacccuccca ggcaccagac | 2460 |
| acagggcacg guggagagac uucuccccg uggccgccuu ggcuccccg uuugcccga | 2520 |
| ggcugcucuu cugucagacu uccucuuugu accacagugg cucuggggcc aggccugccu | 2580 |
| gcccacuggc caucgccacc uuacccagcu gccuccuacc agcaguuucu cugaagaucu | 2640 |
| gucaacaggu uaagucaauc uggggcuucc acugccugca uccaguccc cagagcuugg | 2700 |
| uggucccgaa acgggaagua cauauugggg cauggugcc uccgugagca aauggugucu | 2760 |
| ugggcaaucu gaggccagga cagauguugc cccaccacu ggagauggug cugagggagg | 2820 |
| ugggugggc cuucugggaa ggugagugga gagggcacc ugcccccgc ccuccccauc | 2880 |
| cccuacucc acugcucagc gcgggccauu gcaagggugc cacacaaugu cuugccacc | 2940 |
| cugggacacu ucugaguaug aagcgggaug cuauuaaaaa cuacauggg aaacagguge | 3000 |
| aaaaaaaaaa aaaaaaaaa aaa | 3023 |

<210> SEQ ID NO 7
<211> LENGTH: 3023
<212> TYPE: DNA
<213> ORGANISM: Homo sapiens
<220> FEATURE:
<221> NAME/KEY: mRNA
<222> LOCATION: (1)..(3023)
<223> OTHER INFORMATION: mRNA of SISP-1

<400> SEQUENCE: 7

| | |
|---|---|
| gggtctcaga aacatcagag agaggtttgt agtttcgctc tggagggcag aacagccgga | 60 |
| agaagaacca actgctggtt atctcaggct ggaggtggta gctgaagggg gtgtggacag | 120 |
| taaggatttg ccgggaaaaa ggaagggtca ggacatttcg tgaagtggga ggacttgagc | 180 |
| tgagccctga gggatgagaa gaattaggag gggagagaca ttccagtggt gccagcagtg | 240 |
| ctgggtgtgg gtgcaagagc agaggcacta gaagttaggg tgcatcagag tgtcctgcag | 300 |
| atatccaggc accagggagg gagggcgggt gcacagccag gcggacagct gaggcctctg | 360 |

-continued

```
ccggagggga gcttgcagga tgtgctgtgg ggcacgccaa caggtgttgc ctgcatatct      420
gtgtgtgtcc cggggtaggg atgtgctgat cttggcgtgt agtcctgcac ctgttctgtg      480
tgtgtgtgtg tgtgtgtgtg tgtgtgtgtg tgtgcgcgcg cgcatgcact cagggtgctc      540
caggctctga atctacagtt aaactggctc cagcttgcct agctcttcac aatgtcagat      600
ttcattcatt cactcattta ctcactcatt ccacagctgg gagtgcctac cataccaa       660 gccctggtct ggctggagga tgtagggtac aagtctctgt ccccagatca ctcaaaggct     720
ggtggctgag ggcagatgca agccatggta acgtctatca cgctgttaga ggtagatcta    780
cttcttaggc tgcgcagcaa taataatttc tctccaaaag gactggggga cggtagaacg    840
ggctttaaac tgccgatcaa gtggagctga ctcgctggga cgcacgctgg ctccccaccc    900
acggggccgg cctccgggaa gcccctccca cgcggccctc ggagaggcag ttcccccaca    960 cggcccccg ggggcgctgc gcgaaggggg cgggtgcctg gagcacgcg ctggggccgc     1020 ccgcagcgct cactcgctcg cactcagtcg cgggaggctt ccccgcgccg ccgcgtccc    1080 gcccgctccc cggcaccaga agttcctctg cgcgtccgac ggcgacatgg gcgtccccac    1140
ggccctggag gccggcagct ggcgctgggg atccctgctc ttcgctctct tcctggctgc    1200
gtccctaggt ccggtggcag ccttcaaggt cgccacgccg tattccctgt atgtctgtcc    1260
cgaggggcag aacgtcaccc tcacctgcag gctcttgggc cctgtggaca aagggcacga   1320
tgtgaccttc tacaagacgt ggtaccgcag ctcgaggggc gaggtgcaga cctgctcaga    1380
gcgccggccc atccgcaacc tcacgttcca ggaccttcac ctgcaccatg gaggccacca   1440
ggctgccaac accagccacg acctggctca gcgccacggg ctggagtcgg cctccgacca   1500
ccatggcaac ttctccatca ccatgcgcaa cctgaccctg ctggatagcg gcctctactg   1560
ctgcctggtg gtggagatca ggcaccacca ctcggagcac agggtccatg gtgccatgga   1620
gctgcaggtg cagacaggca aagatgcacc atccaactgt gtggtgtacc catcctcctc    1680
ccaggagagt gaaaacatca cggctgcagc cctggctacg ggtgcctgca tcgtaggaat    1740
cctctgcctc cccctcatcc tgctcctggt ctacaagcaa aggcaggcag cctccaaccg    1800
ccgtgcccag gagctggtgc ggatggacag caacattcaa gggattgaaa accccggctt    1860
tgaagcctca ccacctgccc aggggatacc cgaggccaaa gtcaggcacc cctgtcctta   1920
tgtggcccag cggcagcctt ctgagtctgg gcggcatctg ctttcggagc ccagcacccc   1980
cctgtctcct ccaggccccg agacgtctct cttcccatcc ctggaccctg tcctgactc    2040 tccaaacttt gaggtcatct agcccagctg ggggacagtg ggctgttgtg ctgggtctg    2100 gggcaggtgc atttgagcca gggctggctc tgtgagtggc ctccttggcc tcggccctgg   2160
ttccctccct cctgctctgg gctcagatac tgtgacatcc cagaagccca gcccctcaac   2220
ccctctggat gctacatggg gatgctggac ggctcagccc ctgttccaag gattttgggg   2280
tgctgagatt ctcccctaga gacctgaaat tcaccagcta cagatgccaa atgacttaca   2340
tcttaagaag tctcagaacg tccagccctt cagcagctct cgttctgaga catgagcctt   2400
gggatgtggc agcatcagtg ggacaagatg gacactgggc caccctccca ggcaccagac   2460
acagggcacg gtggagagac ttctcccccg tggccgcctt ggctccccg ttttgcccga     2520 ggctgctctt ctgtcagact tcctctttgt accacagtgg ctctggggcc aggcctgcct     2580
gcccactggc catcgccacc ttacccagct gcctcctacc agcagtttct ctgaagatct    2640
gtcaacaggt taagtcaatc tggggcttcc actgcctgca ttccagtccc cagagcttgg   2700
```

-continued

```
tggtcccgaa acgggaagta catattgggg catggtggcc tccgtgagca aatggtgtct    2760
tgggcaatct gaggccagga cagatgttgc cccacccact ggagatggtg ctgagggagg    2820 tgggtgggc cttctgggaa ggtgagtgga gaggggcacc tgcccccgc cctccccatc      2880 ccctactccc actgctcagc gcgggccatt gcaaggggtgc cacacaatgt cttgtccacc   2940
ctgggacact tctgagtatg aagcgggatg ctattaaaaa ctacatgggg aaacaggtgc    3000
aaaaaaaaaa aaaaaaaaaa aaa                                            3023
```

<210> SEQ ID NO 8
<211> LENGTH: 936
<212> TYPE: DNA
<213> ORGANISM: Homo sapiens
<220> FEATURE:
<221> NAME/KEY: mRNA
<222> LOCATION: (1)..(936)
<223> OTHER INFORMATION: SISP-1 mRNA without 5' and 3' untranslated
      region

<400> SEQUENCE: 8

```
atgggcgtcc ccacggccct ggaggccggc agctggcgct ggggatccct gctcttcgct    60
ctcttcctgg ctgcgtccct aggtccggtg gcagccttca aggtcgccac gccgtattcc    120
ctgtatgtct gtcccgaggg gcagaacgtc accctcacct gcaggctctt gggccctgtg    180
gacaaagggc acgatgtgac cttctacaag acgtggtacc gcagctcgag gggcgaggtg    240
cagacctgct cagagcgccg gcccatccgc aacctcacgt tccaggacct tcacctgcac    300
catggaggcc accaggctgc caacaccagc cacgacctgg ctcagcgcca cgggctggag    360
tcggcctccg accaccatgg caacttctcc atcaccatgc gcaacctgac cctgctggat    420
agcggcctct actgctgcct ggtggtggag atcaggcacc accactcgga gcacagggtc    480
catggtgcca tggagctgca ggtgcagaca ggcaaagatg caccatccaa ctgtgtggtg    540
tacccatcct cctcccagga gagtgaaaac atcacggctg cagccctggc tacgggtgcc    600
tgcatcgtag gaatcctctg cctcccccctc atcctgctcc tggtctacaa gcaaaggcag    660
gcagcctcca accgccgtgc ccaggagctg gtgcggatgg acagcaacat tcaagggatt    720
gaaaaccccg gctttgaagc ctcaccacct gcccaggggga tacccgaggc caaagtcagg    780 cacccctgt cctatgtggc ccagcggcag ccttctgagt ctgggcggca tctgctttcg     840
gagcccagca ccccctgtc tcctccaggc cccggagacg tcttcttccc atccctggac    900
cctgtccctg actctccaaa ctttgaggtc atctag                              936
```

<210> SEQ ID NO 9
<211> LENGTH: 1930
<212> TYPE: DNA
<213> ORGANISM: Homo sapiens
<220> FEATURE:
<221> NAME/KEY: mRNA
<222> LOCATION: (1)..(1930)
<223> OTHER INFORMATION: SISP-1 mRNA with 5' and 3' untranslated region
<220> FEATURE:
<221> NAME/KEY: exon
<222> LOCATION: (1)..(134)
<223> OTHER INFORMATION: exon 1; Nucleotides 1-53 is an untranslated
      region
<220> FEATURE:
<221> NAME/KEY: exon
<222> LOCATION: (135)..(564)
<223> OTHER INFORMATION: exon 2
<220> FEATURE:
<221> NAME/KEY: exon
<222> LOCATION: (565)..(621)
<223> OTHER INFORMATION: exon 3

```
<220> FEATURE:
<221> NAME/KEY: exon
<222> LOCATION: (622)..(729)
<223> OTHER INFORMATION: exon 4
<220> FEATURE:
<221> NAME/KEY: exon
<222> LOCATION: (730)..(757)
<223> OTHER INFORMATION: exon 5
<220> FEATURE:
<221> NAME/KEY: exon
<222> LOCATION: (758)..(951)
<223> OTHER INFORMATION: exon 6
<220> FEATURE:
<221> NAME/KEY: exon
<222> LOCATION: (952)..(1930)
<223> OTHER INFORMATION: exon 7; Nucleotides 990-1930 is an untranslated
      region

<400> SEQUENCE: 9
gcgtcccgcc cgctccccgg caccagaagt tcctctgcgc gtccgacggc gacatgggcg      60
tccccacggc cctggaggcc ggcagctggc gctgggatc cctgctcttc gctctcttcc     120
tggctgcgtc cctaggtccg gtggcagcct tcaaggtcgc cacgccgtat tccctgtatg    180
tctgtcccga ggggcagaac gtcacccctca cctgcaggct cttgggccct gtggacaaag   240
ggcacgatgt gaccttctac aagacgtggt accgcagctc gaggggcgag gtgcagacct    300
gctcagagcg ccgccccatc cgcaaccctca cgttccagga ccttcacctg caccatggag  360
gccaccaggc tgccaacacc agccacgacc tggctcagcg ccacgggctg gagtcggcct    420
ccgaccacca tggcaacttc tccatcacca tgcgcaacct gacccctgctg gatagcggcc   480 tctactgctg cctggtggtg gagatcaggc accaccactc ggagcacagg gtccatggtg    540
ccatggagct gcaggtgcag acaggcaaag atgcaccatc caactgtgtg gtgtacccat    600
cctcctccca ggagagtgaa acatcacgg ctgcagccct ggctacgggt gcctgcatcg     660
taggaatcct ctgcctcccc ctcatcctgc tcctggtcta aagcaaagg caggcagcct     720 ccaaccgccg tgcccaggag ctggtgcgga tggacagcaa cattcaaggg attgaaaacc    780
ccggctttga agcctcacca cctgcccagg ggatacccga ggccaaagtc aggcaccccc    840
tgtcctatgt ggcccagcgg cagccttctg agtctgggcg gcatctgctt tcggagccca    900
gcacccccct gtctcctcca ggccccggag acgtcttctt cccatccctg gaccctgtcc    960
ctgactctcc aaactttgag gtcatctagc ccagctgggg gacagtgggc tgttgtggct   1020
gggtctgggg caggtgcatt tgagccaggg ctggctctgt gagtggcctc cttggcctcg   1080
gccctggttc cctccctcct gctctgggct cagatactgt gacatcccag aagcccagcc   1140
cctcaacccc tctggatgct acatggggat gctggacggc tcagcccctg ttccaaggat   1200
tttggggtgc tgagattctc ccctagagac ctgaaattca ccagctacag atgccaaatg   1260
acttacatct taagaagtct cagaacgtcc agcccttcag cagctctcgt tctgagacat   1320
gagccttggg atgtggcagc atcagtggga caagatggac actgggccac cctcccaggc   1380
accagacaca gggcacggtg gagagacttc tccccgtgg ccgccttggc tccccgtttt    1440
tgcccgaggc tgctcttctg tcagacttcc tctttgtacc acagtggctc tggggccagg   1500
cctgcctgcc cactggccat cgccaccttta cccagctgcc tcctaccagc agtttctctg   1560
aagatctgtc aacaggttaa gtcaatctgg ggcttccact gcctgcattc cagtcccag    1620 agcttggtgg tcccgaaacg ggaagtacat attggggcat ggtggcctcc gtgagcaaat   1680
ggtgtcttgg gcaatctgag gccaggacag atgttgcccc acccactgga gatggtgctg   1740
agggaggtgg gtggggcctt ctgggaaggt gagtggagag gggcacctgc ccccgccct    1800
```

```
-continued ccccatcccc tactcccact gctcagcgcg ggccattgca agggtgccac acaatgtctt    1860
gtccaccctg ggacacttct gagtatgaag cgggatgcta ttaaaaacta catggggaaa    1920
caggtgcaaa                                                           1930

<210> SEQ ID NO 10
<211> LENGTH: 10
<212> TYPE: DNA
<213> ORGANISM: Homo sapiens

<400> SEQUENCE: 10 rrrcwwgyyy                                                           10
```

SISP-1, A NOVEL P53 TARGET GENE AND USE THEREOF

CROSS-REFERENCE TO RELATED APPLICATION

This application claims priority from U.S. Provisional Application Ser. No. 60/767,047, filed on Feb. 28, 2006, the disclosure of which is incorporated herein in its entirely by reference.

FIELD OF THE INVENTION

The present invention relates to a novel p53 target gene SISP-1 (Stress Induced Secreted Protein-1) whose transcription is induced by p53 and a SISP-1 protein encoded by the gene. Furthermore, the present invention relates to the use of the gene/protein for treating diseases associated with abnormal apoptosis such as tumor etc. by modulating apoptosis.

BACKGROUND OF THE INVENTION

Apoptosis, which is also called programmed cell death, is a form of cell death in which a programmed sequence of events leads to the elimination of cells without releasing harmful substances into the surrounding area. Apoptosis plays a crucial role in developing and maintaining health by eliminating old cells, unnecessary cells, and unhealthy cells. Apoptotic processes are of widespread biological significance, being involved, for example, in development, differentiation, proliferation/homeostasis, regulation and function of the immune system and in the removal of defect and therefore harmful cells. However, too little or too much apoptosis can cause many diseases. Defects in apoptosis can result in tumor, autoimmune diseases and spreading viral infections, while neurodegenerative disorders such as Alzheimer, Huntington and Parkinson diseases, AIDS and ischaemic diseases are caused or enhanced by excessive apoptosis (Fadeel B, Orrenius S, Zhivotovsky B. Apoptosis in human disease: a new skin for the old ceremony? *Biochem Biophys Res Commun.* 266(3), 699-717(1999)). Therefore, regulating apoptosis is important in the treatment or prevention of diseases whose pathology is related with apoptosis.

A benign tumor or malignant tumor is a group of diseases characterized by uncontrolled cell division leading to growth of abnormal tissue. Cell multiplication (proliferation) is a normal physiologic process that occurs in almost all tissues and under many circumstances, such as response to injury, immune responses, or to replace cells that have died or have been shed as a part of their lifecycle (in tissues such as skin or the mucous membranes of the digestive tract). Normally the balance between proliferation and cell death is tightly regulated to ensure the integrity of organs and tissues. The uncontrolled and often rapid proliferation of cells can lead to either a benign tumor or a malignant tumor (cancer). The unregulated growth is caused by damage to DNA, resulting in mutations to genes that encode for proteins controlling cell division.

Tumor development is a multistage process that results from the step wise acquisition of genetic alterations. These alterations may involve the dysregulation of a variety of normal cellular functions, leading to the initiation and progression of a tumor. In many tumors, pro-apoptotic proteins have inactivating mutations or the expression of anti-apoptotic proteins is upregulated, leading to the unchecked growth of the tumor and inability to respond to chemotherapy.

P53 is a pro-apoptotic gene present in all cells. P53, which is called as a tumor suppressor gene, plays a critical role in maintaining cellular homeostasis and tumor-free survival of the organism by modulating cell cycle progression or apoptosis (Vogelstein et al., Surfing the p53 network. *Nature* 408: 307-310 (2000). Normally it induces apoptosis by activating caspases 9, 8, 7, and 3. The inactivation of p53 decreases caspase activation and therefore the cell will not undergo apoptosis. Therefore, inactivation of p53 is closely related with development of cancerous states. Mutation in the p53 gene is the most common mutation in cancer; it is present in about half of all cancer tumors, 80% in all colon cancer tumors, 50% of lung cancer tumors, and 40% of breast cancer tumors.

The tumor suppressor p53 gene is activated in response to stress stimuli and functions as a transcription factor to promote antiproliferative responses, including cell cycle checkpoint and apoptosis (Ko, L. J. & Prives, C. p53: puzzle and paradigm. *Genes Dev.* 10, 1054-72 (1996); Levine, A. J. p53, the cellular gatekeeper for growth and division. *Cell* 88, 323-331 (1997); Oren, M. Decision making by p53: life, death and cancer. *Cell Death Differ.* 10, 431-442 (2003); Benchimol, S. p53—an examination of sibling support in apoptosis control. *Cancer Cell* 6, 3-4 (2004); Harms, K., Nozell, S. & Chen, X. The common and distinct target genes of the p53 family transcription factors. *Cell Mol. Life Sci.* 61, 822-842 (2004)). The p53 tumor suppressor gene encodes a transcription factor that is a potent inducer of apoptosis in response to genotoxic/chemotherapeutic agents, preventing the persistence of potentially cancer-prone cells.

The p53 protein functions as a transcription factor with a high affinity for specific DNA target sequences in response to DNA damage or hypoxia. It selectively destroys stressed or abnormal cells to prevent the progression to cancer. Although the number of genes activated by p53 is rather large, the outcome of p53 activation is either cell cycle arrest in G1, in G2 or apoptosis.

Although the mechanism by which p53 activates the G1 arrest is well characterized and involves primarily the transcriptional activation of the cyclin-dependent kinase inhibitor $p21^{Waf1}$, the precise nature of the p53 transcriptional program for p53-dependent apoptosis is still unclear. Among several previously identified p53 pro-apoptotic target genes, at least two pro-apoptotic members of the TNFR superfamily, Fas/Apo1/CD95 and DR5/KILLER, have been shown to be regulated in a p53-dependent manner in response to genotoxic drugs (Wu, G. S. et al. KILLER/DR5 is a DNA damage-inducible p53-regulated death receptor gene. *Nat. Genet.* 17, 141-143 (1997); Owen-Schaub, L. B. et al. Wild-type human p53 and a temperature-sensitive mutant induce Fas/APO-1 expression. *Mol. Cell. Biol.* 15, 3032-3040 (1995); Zalcenstein, A. et al. Mutant p53 gain of function: repression of CD95(Fas/APO-1) gene expression by tumor-associated p53 mutants. *Oncogene* 22, 5667-5676 (2003)), suggesting a potential link between p53-mediated intrinsic pathway of apoptosis and TNF-induced extrinsic pathway of apoptosis. TNF-α is an important cytokine that orchestrates pleiotropic functions not only in the host immunity response but also in control of cell proliferation, differentiation, and apoptosis (Ashkenazi, A. & Dixit, V. M. Death receptors: signaling and modulation. *Science* 281, 1305-1308 (1998); Baud, V. & Karin, M. Signal transduction by tumor necrosis factor and its relatives. *Trends Cell Biol.* 11, 372-377 (2001); Chen, G. & Goeddel, D. V. TNF-R1 signaling: a beautiful pathway. *Science* 296, 1634-1635 (2002); Wajant, H., Pfizenmaier, K. & Scheurich, P. Tumor necrosis factor signaling. *Cell Death Differ* 10, 45-65 (2003); Fesik, S. W. Promoting apoptosis as a strategy for cancer drug discovery. *Nat Rev Cancer* 5:876-885 (2005); Rowinsky, E. K. Targeted induction of apoptosis in cancer management: the emerging role of tumor necrosis factor-related apoptosis-inducing ligand receptor activating agents. *J Clin. Oncol.* 23:9394-9407, (2005)). Physiologically, the secretion of TNF-α is highly localized and transient, but it is shown to be toxic. However, no clear understanding exists in the regulatory mechanisms that enable the efficient production of TNF-α or TRAIL in order to mediate its other functions such as control of cell proliferation and apoptosis.

Drugs that restore the normal apoptotic pathways have the potential for effectively treating diseases that depend on aberrations of the apoptotic pathway to stay alive and spread. Although a number of potential apoptosis inducing agents are currently being explored for cancer drug discovery, most of drugs are toxic to normal cells and show significant side effects. Therefore, a need exists to identify and develop apoptosis targets/inducers for cancer therapy.

The information disclosed in this Background of the Invention section is only for enhancement of understanding the background of the invention and therefore, unless explicitly described to the contrary, it should not be taken as an acknowledgement or any form of suggestion that this information forms the prior art that is already known in this country to a person of ordinary skill in the art.

SUMMARY OF THE INVENTION

Many points of the mechanism of p53-medicated apoptosis remain to be clarified. In order to discover more effective treatment method of diseases associated with apoptosis, it may be necessary to clearly understand the mechanisms by which p53 accomplishes its biological functions associated with apoptosis. Therefore the primary objective of the present invention is to elucidate the mechanism of p53-induced apoptosis. It is also amongst the objects of the present invention to seek to identify a novel pro-apoptotic p53 target gene and a protein encoded by the gene. In addition, the object of the present invention is to provide the use associated apoptosis of the gene and the protein.

The present invention is based on the discovery of a novel p53 target gene SISP-1 (Stress Induced Secreted Protein-1). The present inventor also found out that SISP-1 induces apoptosis. Based on the new findings, the present invention provides a SISP-1 gene and the protein encoded by the gene. In addition, the present invention provides their newly-discovered use for inducing apoptosis and for treating, preventing and diagnosing diseases associated with abnormal apoptosis such as tumor et al.

"SISP-1" of the present invention is identical to "TSSP1" of the U.S. Provisional Application Ser. No. 60/767,047 from which the present invention claims priority. The identity between SISP-1 and TSSP1 is clear from the fact that the amino acid sequence of SISP-1 protein in FIG. 2 of the present invention is the same as that of TSSP-1 in FIG. 1 of the provisional application.

More specifically, the present invention relates to:

(1) A polypeptide comprising an amino acid sequence selected from the group consisting of:

(a) Sequence represented by SEQ ID NO: 2;

(b) Sequences having at least 75% identity to SEQ ID NO: 2;

(c) Sequences having at least 90% identity to SEQ ID NO: 2; and (d) Sequences resulting from the deletion, addition, insertion or substitution of one to ten amino acid residues in the amino acid sequence represented by SEQ ID NO: 2, or derivatives thereof, fragments thereof or species specific homologues thereof, wherein said polypeptide induces apoptosis in cells.

(2) An isolated nucleic acid molecule comprising the sequence selected form the group consisting of:

(a) Sequence encoding a polypeptide of (1) or the complement thereof;

(b) Sequence represented by SEQ ID NO: 1 or the complement thereof, (c) Sequence represented by SEQ ID NO: 3, SEQ ID NO: 4, SEQ, ID NO: 6 or the complement thereof, and (d) Sequence of a nucleic acid that capable of hybridizing under stringent conditions to any one of the nucleic acid consisting of the sequence specified in (a) to (c), or derivatives thereof, fragments thereof or species specific homologues thereof.

(3) An antibody specific to the polypeptide of (1), or fragments thereof, derivatives thereof or homologues thereof.

(4) A recombinant expression vector comprising the nucleic acid molecule of (2).

(5) A viral vector comprising the nucleic acid molecule of (2).

(6) A non-viral vector comprising the nucleic acid molecule of (2).

(7) A host cell transformed with the nucleic acid molecule of (2).

(8) An antisense oligonucleotide comprising nucleotides which are complementary to a nucleotide sequence encoding the polypeptide of (1), wherein the oligonucleotide is capable of inhibiting the expression of said polypeptide.

(9) A method of treating or preventing diseases associated with abnormal cell proliferation comprising administering to a patient a therapeutically effective amount of the polypeptide of (1), the nucleic acid molecule of (2), the viral vector comprising the nucleic acid molecule of (2) and/or the non-viral vector comprising the nucleic acid molecule of (2), in order to induce apoptosis in cells with abnormal proliferation.

(10) The method of (9), wherein said disease is a tumor.

(11) The method of (9), wherein said tumor is selected from the group consisting of bladder carcinoma, blood or bone marrow—hematological malignancies, leukemia, lymphoma, Hodgkin's disease, non-Hodgkin's lymphoma, multiple myeloma, brain tumor, breast cancer, cervical cancer, colorectal cancer—in the colon, rectum, anus, or appendix, esophageal cancer, endometrial cancer—in the uterus, hepatocellular carcinoma—in the liver, gastrointestinal stromal tumor (GIST), laryngeal cancer, lung cancer, mesothelioma—in the pleura or pericardium, oral cancer, osteosarcoma—in bones, ovarian cancer, pancreatic cancer, prostate cancer, renal cell carcinoma—in the kidneys, rhabdomyosarcoma—in muscles, skin cancer (including benign moles and dysplastic nevi), stomach cancer, testicular cancer, and thyroid cancer.

(12) A pharmaceutical composition comprising a therapeutically effective amount of the polypeptide of (1), the nucleic acid molecule of (2), the viral vector comprising the nucleic acid molecule of (2) and/or the non-viral vector comprising the nucleic acid molecule of (2), and a pharmaceutically acceptable carrier or excipient.

(13) A pharmaceutical composition for treating or preventing diseases associated with abnormal cell proliferation comprising a therapeutically effective amount of the polypeptide of (1), the nucleic acid molecule of (2), the viral vector comprising the nucleic acid molecule of (2) and/or the non-viral vector comprising the nucleic acid molecule of (2), and a pharmaceutically acceptable carrier or excipient.

(14) The pharmaceutical composition of (13), wherein said disease is a tumor.

(15) The pharmaceutical composition of (14), wherein said tumor is selected from the group consisting of bladder carcinoma, blood or bone marrow—hematological malignancies, leukemia, lymphoma, Hodgkin's disease, non-Hodgkin's lymphoma, multiple myeloma, brain tumor, breast cancer, cervical cancer, colorectal cancer—in the colon, rectum, anus, or appendix, esophageal cancer, endometrial cancer—in the uterus, hepatocellular carcinoma—in the liver, gastrointestinal stromal tumor (GIST), laryngeal cancer, lung cancer, mesothelioma—in the pleura or pericardium, oral cancer, osteosarcoma—in bones, ovarian cancer, pancreatic cancer, prostate cancer, renal cell carcinoma—in the kidneys, rhabdomyosarcoma—in muscles, skin cancer (including benign moles and dysplastic nevi), stomach cancer, testicular cancer, and thyroid cancer.

(16) A method of inducing apoptosis in a cell comprising a step of administering to a tissue or a subject associated with a disease condition a therapeutic amount of the polypeptide of (1), the nucleic acid molecule of (2), the viral vector comprising the nucleic acid molecule of (2) and/or the non-viral vector comprising the nucleic acid molecule of (2).

(17) The method of (16), wherein said disease is a tumor.

(18) The method of (17), wherein said tumor is selected from the group consisting of bladder carcinoma, blood or bone marrow—hematological malignancies, leukemia, lymphoma, Hodgkin's disease, non-Hodgkin's lymphoma, multiple myeloma, brain tumor, breast cancer, cervical cancer, colorectal cancer—in the colon, rectum, anus, or appendix, esophageal cancer, endometrial cancer—in the uterus, hepatocellular carcinoma—in the liver, gastrointestinal stromal tumor (GIST), laryngeal cancer, lung cancer, mesothelioma—in the pleura or pericardium, oral cancer, osteosarcoma—in bones, ovarian cancer, pancreatic cancer, prostate cancer, renal cell carcinoma—in the kidneys, rhabdomyosarcoma—in muscles, skin cancer (including benign moles and dysplastic nevi), stomach cancer, testicular cancer, and thyroid cancer.

(19) A pharmaceutical composition for inducing apoptosis in a target mammalian tissue comprising a therapeutically effective amount of the polypeptide of (1), the nucleic acid molecule of (2), the viral vector comprising the nucleic acid molecule of (2) and/or the non-viral vector comprising the nucleic acid molecule of (2), and a pharmaceutically acceptable carrier or excipient.

(20) A pharmaceutical composition of (19), wherein said target mammalian tissue is associated with a tumor.

(21) The pharmaceutical composition of (20), wherein said tumor is selected from the group of tumors consisting of bladder carcinoma, blood or bone marrow—hematological malignancies, leukemia, lymphoma, Hodgkin's disease, non-Hodgkin's lymphoma, multiple myeloma, brain tumor, breast cancer, cervical cancer, colorectal cancer—in the colon, rectum, anus, or appendix, esophageal cancer, endometrial cancer—in the uterus, hepatocellular carcinoma—in the liver, gastrointestinal stromal tumor (GIST), laryngeal cancer, lung cancer, mesothelioma—in the pleura or pericardium, oral cancer, osteosarcoma—in bones, ovarian cancer, pancreatic cancer, prostate cancer, renal cell carcinoma—in the kidneys, rhabdomyosarcoma—in muscles, skin cancer (including benign moles and dysplastic nevi), stomach cancer, testicular cancer, and thyroid cancer.

(22) A method for estimating the possibility of the tumor development in a subject or for diagnosing a tumor, comprising assaying a sample of the subject for the expression of SISP-1 protein or the induction of SISP-1 mRNA, wherein SISP-1 protein or SISP-1 mRNA detected below normal in the sample is indicative of either high possibility of the tumor development in the subject or the tumor existence in the subject.

(23) A kit for estimating the possibility of the tumor development in a subject or for diagnosing a tumor, comprising (a) at least one agent reactive with SISP-1 protein or SISP-1 mRNA; and (b) reagents suitable for detecting the expression of SISP-1 protein or inducing of SISP-1 mRNA.

(24) The kit of (23), wherein said at least one agent reactive with SISP-1 protein is an antibody specific to SISP-1 protein or its fragment.

(25) The kit of (23), wherein said at least one agent reactive with SISP-1 mRNA is a complement to SISP-1 mRNA or its fragment.

(26) The kit of any of (23) to (25), wherein said at least one agent is labeled with a detectable marker.

(27) A method for monitoring the efficacy of therapy to treat tumor in a subject, who has undergone or is undergoing treatment for tumor, comprising assaying a sample of the subject for the expression of SISP-1 protein or the induction of SISP-1 mRNA, wherein the detection of normal or elevated SISP-1 protein or SISP-1 mRNA in the sample is indicative of successful therapy to treat tumor and the detection of decreased SISP-1 protein or SISP-1 mRNA below normal in the sample is indicative of a need to continue therapy to treat tumor.

(28) A method for screening a compound for an apoptosis-regulating agent comprising the step of:

(a) culturing a cell containing the nucleic acid molecule of (2) and measuring the expression level of said nucleic acid;

(b) separately from step (a), culturing a sample containing a candidate compound with a cell containing the nucleic acid of (2) under the same condition as step (a) and measuring the expression level of said nucleic acid; and (c) selecting a compound in the sample capable of the higher or lower expression level of said nucleic acid measured in step (b) than that in step (a).

(29) The method for screening of (28), wherein said cell containing the nucleic acid molecule of (2) is a cell containing a vector with the structure in which the nucleic acid molecule of (2) is operably linked to a reporter gene and said measurement refers to the expression level of the reporter gene.

(30) A method for screening a compound for an apoptosis-regulating agent, comprising the step of:

(a) contacting a sample containing a candidate compound with the polypeptide of (1) or the nucleic acid molecule of (2);

(b) detecting the binding ability of the candidate compound in the sample to said polypeptide or nucleic acid molecule; and (c) selecting a compound having the binding ability to said protein or nucleic acid molecule.

(31) A method for screening a compound for an apoptosis-regulating agent, comprising the step of:

(a) preparing an in vitro system comprising tumor cells which is sensitive to the apoptosis by either the polypeptide of (1) or the nucleic acid molecule of (2);

(b) contacting both a sample containing a candidate compound and either the polypeptide of (1) or the nucleic acid molecule of (2) with the in vitro system;

(c) determining the apoptosis level of said tumor cells;

(d) comparing the apoptosis level of said tumor cells which are treated by both the candidate sample and either the polypeptide of (1) or nucleic acid molecule of (2), with the apoptosis level of the tumor cells which are treated only by either the polypeptide of (1) or the nucleic acid molecule of (2); and (e) selecting a compound capable of the higher or lower apoptosis level of the tumor cells than that measured using only either the polypeptide of (1) or the nucleic acid molecule of (2).

(32) The method for screening of (31), wherein the apoptosis-regulating agent is tumor treatment agent.

(33) A kit for screening a compound for an apoptosis-regulating agent, comprising (a) tumor cells which are sensitive to the apoptosis by either the polypeptide of (1) or the nucleic acid molecule of (2); (b) the polypeptide of (1) or the nucleic acid molecule of (2); and (c) reagents suitable for detecting the apoptosis level of the tumor cells.

(34) A kit for screening a compound for an apoptosis-regulating agent, comprising (a) a cell containing a nucleic acid molecule of (2) and (b) reagents suitable for detecting the expression level of the nucleic acid.

(35) A kit for screening a compound for an apoptosis-regulating agent, comprising (a) a cell containing a vector with the structure in which the nucleic acid molecule of (2) is operably linked to a reporter gene and (b) reagents suitable for detecting the expression level of the reporter gene.

(36) The kit for screening a compound for an apoptosis-regulating agent of either (34) or (35), wherein said reagents suitable for detecting the expression level are labeled with a detectable marker.

(37) The kit for screening a compound for an apoptosis-regulating agent of either (34) or (35), wherein one of said reagents suitable for detecting the expression level is an antibody specific to the polypeptide of (1), fragments thereof, derivatives thereof or homologues thereof.

(38) The kit for screening a compound for an apoptosis-regulating agent of either (34) or (35), wherein one of said reagents suitable for detecting the expression level is a complement to SISP-1 mRNA or its fragments. (39) A method for increasing the sensitivity to chemo-drug-induced apoptosis of tumor cells comprising a step of administering to a subject undergoing treatment with chemo-drug a therapeutically effective amount of the polypeptide of (1), the nucleic acid molecule of (2), the viral vector comprising the nucleic acid molecule of (2) and/or the non-viral vector comprising the nucleic acid molecule of (2).

(40) A pharmaceutical composition for increasing the sensitivity to chemo-drug-induced apoptosis of tumor cells comprising a therapeutically effective amount of the polypeptide of (1) or the nucleic acid molecule of (2), the viral vector comprising the nucleic acid molecule of (2) and/or the non-viral vector comprising the nucleic acid molecule of (2), and a pharmaceutically acceptable carrier or excipient.

BRIEF DESCRIPTION OF THE FIGURES

FIG. 1 sets forth the nucleotide sequence of cDNA of SISP-1, which is shown in SEQ ID NO:1.

FIGS. 2A and 2B demonstrate the information of SISP-1. FIG. 2A sets forth the amino acid sequence of SISP-1, which is shown in SEQ ID NO:2. FIG. 2B is a schematic representation of the functional domain of the primary structure.

FIG. 3 shows the p53 binding site in SISP-1 promoter, which is shown in SEQ ID NO:5.

FIG. 5 shows the result of the western blotting analysis of cell lysate and cell culture medium after a carboxyl or N-terminally myc- or HA-tagged SISP-1 was expressed by culture. It demonstrates that SISP-1 is a secreted protein.

FIG. 8A) and human breast cancer cells (MDAMB435; FIG. 8B).

FIG. 12 demonstrates SISP-1 expression in human normal tissues (FIG. 10A) and in tumor cells (FIG. 10B) assayed by Northern blot analysis. The expression is significantly reduced in human breast cancer cells, as compared to normal counterparts.

FIGS. 13 to 20 set forth the nucleotide sequences of SISP-1 gDNA, which are shown in SEQ ID NOs: 3 and 4. Nucleotides in exon are represented in bold faced letters and nucleotides in untranslated region are italicized letters.

FIG. 21 shows the nucleotide sequence of SISP-1 mRNA, which is shown in SEQ ID NO:7. The underlined part is a p53 binding site.

FIG. 22 shows nucleotide sequence of SISP-1 mRNA without 5' and 3' untranslated region, which is set forth in SEQ ID NO:8.

FIGS. 23 and 24 show nucleotide sequence of SISP-1 mRNA with 5' and 3' untranslated region, which is set forth in SEQ ID NO:9. Nucleotides in untranslated region are shown in italicized letters.

DETAILED DESCRIPTION OF THE INVENTION

Figure 4:
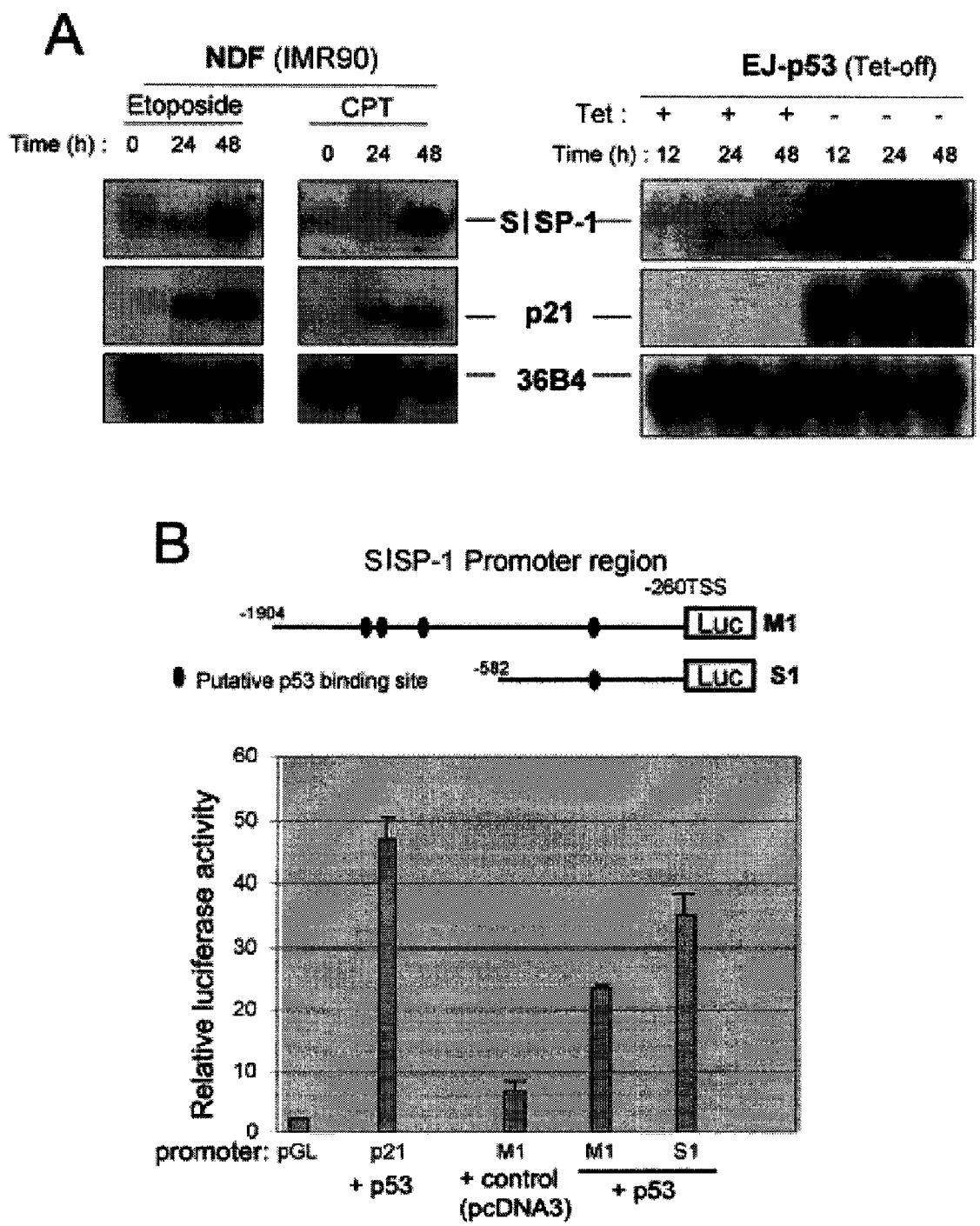
FIGS. 4A and 4B show that SISP-1 is induced in response to genotoxic stress or tumor suppressor p53.

Unless otherwise defined, all technical terms used herein have the same meaning as commonly understood by one of ordinary skill in the pertinent art.

The present invention relates to a novel p53 target gene SISP-1 (Stress Induced Secreted Protein 1) whose transcription is induced by p53 and a SISP-1 protein encoded by the gene. The present inventor found out that the overexpression of SISP-1 in cancer cells is sufficient to induce cell death.

The present inventor performed gene expression array analyses to identify transcriptional targets regulated by p53 during apoptosis, using a p53-inducible cell line. Genes expressed in the presence and absence of p53 were compared. SISP-1, Stress Induced Secreted Protein-1, was identified as a p53 up-regulated gene. SISP-1 is a new gene that has not been reported in public; in particular, the function of this gene has not been reported (especially related the apoptotic function). Its cDNA (FIG. 1; SEQ ID NO: 1) encodes a 311-amino acid protein (FIG. 2A; SEQ ID NO: 2), with a predicted molecular mass of ~35 kDa. Examination of the amino acid sequence identified a high sequence similarity in the N-terminal region (amino acid 29 to 148) of the predicted SISP-1 sequence with the IG-like/death domain motif (FIG. 2B), which often found in the apoptotic proteins and a signal peptide sequence at N-terminus. The inventor of the present invention searched for potential p53 binding site(s) within its genomic sequence. Four potential sites were identified in the promoter region, which revealed an 85% or greater match to the consensus p53-binding sequence. However, the functional analysis of these putative four p53 binding sites revealed that only one of these putative p53 binding sites, 475 bp upstream from the transcription start site, contained activity (FIG. 3).

The present invention provides a SISP-1 protein which induces apoptosis, a nucleic acid molecule comprising sequence encoding SISP-1 protein and their functionally equivalent variants, derivatives, fragments and homologues. A polypeptide comprising sequence of SEQ ID No: 2 is an example of SISP-1 protein. The present invention includes proteins structurally analogous to SISP-1 protein as long as they have the activity to induce apoptosis. Such analogous protein include mutant of SISP-1 protein and SISP-1 protein derived from other organisms. Whether cells undergo apoptosis or not can be determined by usual methods performed by those skilled in the art. For example, as shown Examples 6 to 8, Cell-Death Elisa method can be carried out using a commercial kit.

The present invention includes proteins having amino acid sequences altered from those of the natural SISP-1 due to the artificial or natural substitution, deletion, addition, and/or insertion of amino acids as long as they have the activity to induce apoptosis. Preferably, an amino acid can be substituted with the one having similar property to that of the amino acid to be substituted. For example, since Ala, Val, Leu, Ile, Pro, Met, Phe, and Trp are all classified into the non-polar amino acids, they are thought to have similar properties each other. Non-charged amino acids are exemplified by Gly, Ser, Thr, Cys, Tyr, Asn, and Gln, which acidic amino acids include Asp and Glu, and basic amino acids include Lys, Arg and His. When artificial modification in the proteins is performed, usually 30 amino acids or less, preferably 10 amino acids or less, and more preferably 5 amino acids or less are modified.

The present invention also includes a polypeptide comprising an amino acid sequence having at least 50% identity, preferably 75% identity, more preferably 90% identity to SISP-1 protein, for example, protein comprising sequence of SEQ ID NO:2.

The above proteins can be prepared by known methods for mutagensis, for example, site-directed mutagenesis methods such as the method with deletion-mutant preparation (Kowalski D. et al., J. Biochem., 15, 4457), PCR method, Kunkel method, etc.

The present invention also includes fragment of the protein of this invention. Such fragments may be truncated at the N-terminus or C-terminus, or may lack internal residues, for example, when compared with a full length native protein. Certain fragments lack amino acid residues that are not essential for a desired biological activity of SISP-1 protein. The fragments of the invention can be prepared, for example, by the genetic engineering technique, peptide synthesis methods well-known in the art using solid-phase technique (Merrifield, J. Am. Chem. Soc., 85: 2149-2154 (1963)), or cleavage of the protein of this invention with a suitable peptidase.

The protein of the present invention can be prepared not only as a natural protein but also as a recombinant protein prepared by the gene recombination technique. The recombinant protein may be prepared, as described below, by culturing cells transformed with DNA encoding the SISP-1 protein to express the protein therein and then recovering.

The present invention also relates to a nucleic acid molecule encoding the protein of this invention. The type of the nucleic acid molecule encoding the proteins of this invention is not limited as long as they are capable of encoding the proteins, and includes cDNA, genomic DNA, mRNA, synthetic or recombinantly produced nucleic acid, and nucleic acids comprising nucleotide sequences resulted from the degeneracy of genetic codes, all of which can be prepared by methods that are well-known in the art. For example, to prepare genomic DNA of SISP-1, genomic DNA is extracted from cells expressing SISP-1 protein, which is subsequently used for the construction of a genomic library using vectors such as plasmid, phage, cosmid, BAC, and PAC followed by colony hybridization or plaque hybridization depending on the vectors to screen the SISP-1 genomic DNA using a probe with a sequence specific for the SISP-1 gene of the present invention. Alternately, PCR for the amplification of cDNA encoding SISP-1 protein using primers specific for SISP-1 of the present invention can be used instead of the said colony hybridization or plaque hybridization. For the preparation of cDNA of SISP-1, mRNA extracted from cells expressing SISP-1 protein can be used to synthesize first strand cDNA by reverse-transcription followed by construction of cDNA library and colony hybridization or plaque hybridization or PCR as described above.

SEQ ID NO: 1, and SEQ ID NO: 3 and 4, and SEQ ID NO: 6 are examples of cDNA, gDNA and mRNA of SISP-1, respectively. The present invention also includes a complementary to nucleic acid molecule encoding the protein of this invention or to complementary strand thereof. Preferably, the polynucleotides specifically hybridize to nucleic acid molecule comprising the sequence of SEQ ID NO: 1, SEQ ID NO: 3, SEQ ID No. 4, SEQ ID NO: 6 or the sequence encoding SISP-1 protein. Herein, the phrase "specifically hybridize" means that no significant cross-hybridization to DNAs encoding other proteins occurs under the usual hybridization conditions, and preferably under stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions ", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50<RTI/, tg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

The nucleic acid molecule of the present invention also encompasses those having nucleotide sequences altered from those of the natural SISP-1 due to the insertions, deletions, or substitutions of nucleotide that may be generated spontaneously or artificially by methods that are well-known in the art, e.g., by primer-directed PCR (Kramer, W. & Fritz, H J. Methods in Enzymology (1987) 154:350-367), "error-prone" PCR (Cadwell, R. C. and G. F. Joyce, PCR methods Appl (1992) 2:28-33), "gene-shuffling" called PCR-reassembly of overlapping DNA fragments, and the like. Also encompassed by the present invention is a mutant at the nucleic acid level that does not change an amino acid such as a degenerate variant due to the degeneracy of the genetic code.

The nucleic acid molecules encoding the protein of this invention are useful in producing recombinant proteins. They can be used to prepare the protein of this invention by inserting the nucleic acid (for example, DNA of SEQ ID NO:1, 3 or 4 or mRNA of SEQ ID NO: 6) which encodes the protein of this invention into an appropriate expression vector, transducing suitable cells by the vector, culturing the resulting transformant, and purifying the protein expressed by the transformant.

The vector may, for example, be in the form of a plasmid, cosmid, viral particle, or phage. Suitable host cells for cloning or expressing the DNA in the vectors herein include prokaryote, yeast, or higher eukaryote cells. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed.(IRL Press, 1991).

Expression and cloning vectors usually contain a promoter operably linked to the SISP-1 encoding nucleic acid sequence to direct mRNA synthesis. Promoters recognized by a variety of potential host cells are well known. Promoters suitable for use with prokaryotic hosts include the p-lactamase and lactose promoter systems, alkaline phosphatase, a tryptophan (trp) promoter system and hybrid promoters such as the tac promoter. Promoters for use in bacterial systems also will contain a Shine-Dalgarno (S. D.) sequence operably linked to the DNA encoding SISP-1.

Examples of suitable promoting sequences for use with yeast hosts include the promoters for 3phosphoglycerate kinase or other glycolytic enzymes. SISP-1 transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

The nucleic acid molecule encoding the protein of the present invention may also be applied to the gene therapy of disorders caused by its mutation. Examples of vectors used for the gene therapy are viral vectors such as retroviral vector, adenoviral vector, adeno-associated viral vector, vaccinia viral vector, lentiviral vector, herpes viral vector, alphaviral vector, EB viral vector, papilomaviral vector, and foamyviral vector, and non-viral vector such as cationic liposome, ligand DNA complex, and gene gun. Gene transduction may be carried out in vivo and ex vivo, and also co-transduction with a gene of other cytokines may be carried out.

The present invention also provides an antibody specific to the proteins of this invention. The antibodies of this invention include polyclonal antibody, monoclonal antibody, human antibody and humanized antibody. "Antibody fragments" comprise a portion of an intact antibody, preferably the antigen binding or variable region of the intact antibody. Examples of antibody fragments include Fab, Fab', F(ab') 2, and Fv fragments; diabodies; linearantibodies (Zapataetal., ProteinEng., 8 (10): 1057-1062 (1995)); single-chain antibody molecules; and multi specific antibodies formed from antibody fragments. Papain digestion of antibodies produces two identical antigen-binding fragments, called "Fab" fragments, each with a single antigen-binding site, and a residual "Fc" fragment. Pepsin treatment yields an F (ab') 2 fragment that has two antigen-combining sites and is still capable of cross-linking antigen. "Fv" is the minimum antibody fragment which contains a complete antigen-recognition and— binding site. This region consists of a dimer of one heavy— and one light-chain variable domain in tight, non-covalent association.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intra peritoneal injections. The immunizing agent may include the proteins of the present invention or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The monoclonal antibodies to be used in accordance with the present invention may be made by the hybridoma method first described by Kohler et al., Nature,256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Markset al., J. Mol. Biol., 222: 581-597 (1991).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-68551984]).

"Humanized" forms of non-human (e.g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see, Jones et al., Nature, 321: 522-525 (1986); Reichmann et al., Nature, 332: 323-329 [1988]; and Presta, Curr. Op. Struct. Biol., 2: 593-596 (1992).

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding.

The term "diabodies" refers to small antibody fragments with two antigen-binding sites, which fragments comprise a heavy-chain variable domain (VH) connected to a light-chain variable domain (VJ in the same polypeptide chain (VH-VL). By using a linker that is too short to allow pairing between the two domains on the same chain, the domains are forced to pair with the complementary domains of another chain and create two antigen-binding sites.

The present invention also provides an antisense oligonucleotide of the nucleic acid encoding the proteins of this invention. The antisense oligonucleotide of this invention would suppress the expression of the proteins of the present invention, and useful in developing reagents for elucidating mechanisms of disorders associated with p53-dependent apoptosis and gene therapy drugs for the treatment of the apoptosis-related disorders. The antisense oligonucleotides are preferably antisense to at least continuous 15 or more, 30 or more, preferably 15 to 30 nucleotides in the nucleotide sequence of SEQ ID NO:1, 3 or 4 and more preferably the continuous nucleotides comprises the transcription initiation codon.

The present inventor found out that SISP-1 induces apoptosis, in particular p53-dependent apoptosis and apoptosis in response to chemo-drugs. SISP-1 mRNA induction was confirmed by Northern blot analysis in several cell lines upon ectopic p53 expression. Importantly, SISP-1 mRNA is significantly induced upon exposure to cancer therapeutic drugs in cells containing functional p53, but not in p53-null or p53-mutated cells. In addition, SISP-1 activates pro-apoptotic markers and down-regulates a pro-survival protein.

The present inventor confirmed that SISP-1 expression in numerous tumor cell lines (e.g. tet-inducible-SISP-1 U2OS cells and adenoviral SISP-1-infected HCT116 and EJ cells) causes apoptosis and demonstrated a pro-apoptotic role for SISP-1. However, normal cells were resistant to SISP-1 induced apoptosis.

The present invention showed that N-terminal cleavage of SISP-1 produces a secreted protein that is believed to function as a pro-apoptotic cytokine, and is associated with DR5/TRAIL receptor trimerization and activation. Moreover, it showed that SISP-1 increases the sensitivity of U2OS cells to TRAIL-induced apoptosis.

On the basis of the findings, the present invention provides the use of SISP-1 gene/protein for inducing apoptosis, for diagnosing, preventing or treating diseases associated with abnormal apoptosis and for screening a compound for the apoptosis regulators.

The present invention relates to a method of treating or preventing diseases associated with abnormal cell proliferation comprising administering to a patient a therapeutically effective amount of the protein of this invention (for example, SISP-1 polypeptide, derivative thereof, fragment thereof and homologous thereof), the nucleic acid molecule of this invention (for example, a nucleic acid molecule encoding said protein of the present invention, gDNA of SISP-1, cDNA of SISP-1, mRNA of SISP-1, and their derivative, fragment, and homologous), the viral vector comprising the nucleic acid molecule of this invention and/or the non-viral vector comprising the nucleic acid molecule of this invention, in order to induce apoptosis in cells with abnormal proliferation. Said disease can be a tumor.

"Tumor," as used herein, refers to all neoplastic cell growth and proliferation, whether malignant or benign, and all pre-cancerous and cancerous cells and tissues. Malignant tumor include, but not limited to, bladder carcinoma, blood or bone marrow—hematological malignancies, leukemia, lymphoma, Hodgkin's disease, non-Hodgkin's lymphoma, multiple myeloma, brain tumor, breast cancer, cervical cancer, colorectal cancer—in the colon, rectum, anus, or appendix, esophageal cancer, endometrial cancer—in the uterus, hepatocellular carcinoma—in the liver, gastrointestinal stromal tumor (GIST), laryngeal cancer, lung cancer, mesothelioma—in the pleura or pericardium, oral cancer, osteosarcoma—in bones, ovarian cancer, pancreatic cancer, prostate cancer, renal cell carcinoma—in the kidneys, rhabdomyosarcoma—in muscles, skin cancer (including benign moles and dysplastic nevi), stomach cancer, testicular cancer, and thyroid cancer.

The present invention also provides a pharmaceutical composition comprising a therapeutically effective amount of the protein of this invention, the nucleic acid molecule of this invention, a viral vector comprising the nucleic acid molecule of this invention and/or a non-viral vector comprising the nucleic acid molecule of this invention, and a pharmaceutically acceptable carrier or excipient.

The present invention also provides a pharmaceutical composition for treating or preventing diseases associated with abnormal cell proliferation comprising a therapeutic amount of the protein of this invention, the nucleic acid molecule of this invention, the viral vector comprising the nucleic acid molecule of this invention and/or the non-viral vector comprising the nucleic acid molecule of this invention, and a pharmaceutically acceptable carrier or excipient. Said disease can be a tumor.

In addition, the present invention provides a method of inducing apoptosis in a cell comprising a step of administering to a tissue or a subject associated with a disease condition a therapeutically effective amount of the protein of this invention, the nucleic acid molecule of this invention, the viral vector comprising the nucleic acid molecule of this invention and/or the non-viral vector comprising the nucleic acid molecule of this invention. Said disease condition can be a tumor. The subject is a patient to be treated, wherein the patient is a human as well as a veterinary patient.

The present invention also provides a pharmaceutical composition for inducing apoptosis in a target mammalian tissue comprising a therapeutically effective amount of the protein of this invention, the nucleic acid molecule of this invention, the viral vector comprising the nucleic acid molecule of this invention and/or the non-viral vector comprising the nucleic acid molecule of this invention, and a pharmaceutically acceptable carrier or excipient.

As shown Examples 6 and 7, SISP-1 sensitizes tumor cells to the chemo-drug-induced apoptosis.

Based on the experimental results in the Examples, the present invention includes a method for increasing the sensitivity to chemo-drug-induced apoptosis of tumor cells comprising a step of administering to a subject undergoing treatment with chemo-drug a therapeutically effective amount of protein of this invention, nucleic acid molecule of this invention, the viral vector comprising the nucleic acid molecule of this invention and/or the non-viral vector comprising the nucleic acid molecule of this invention.

Further, the present invention also includes a pharmaceutical composition for increasing the sensitivity to chemo-drug-induced apoptosis of tumor cells comprising a therapeutically effective amount of the protein of this invention, the nucleic acid molecule of this invention, the viral vector comprising the nucleic acid molecule of this invention and/or the non-viral vector comprising the nucleic acid molecule of this invention, and a pharmaceutically acceptable carrier or excipient.

The pharmaceutical composition of the present invention is administered in a manner compatible with the dosage formulation, and in a therapeutically effective amount, for example intravenously, intraperitoneally, intramuscularly, subcutaneously, and intradermally. It may also be administered by any of the other numerous techniques known to those of skill in the art, see for example the latest edition of Remington's Pharmaceutical Science, the entire teachings of which are incorporated herein by reference. For example, for injections, the pharmaceutical composition of the present invention may be formulated in adequate solutions including but not limited to physiologically compatible buffers such as Hank's solution, Ringer's solution, or a physiological saline buffer. The solutions may contain formulatory agents such as suspending, stabilizing, and/or dispersing agents. Alternatively, the pharmaceutical composition of the present invention may be in powder form for combination with a suitable vehicle, e.g., sterile pyrogen-free water, before use. Further, the composition of the present invention may be administered per se or may be applied as an appropriate formulation together with pharmaceutically acceptable carriers, diluents, or excipients that are well-known in the art. In addition, other pharmaceutical delivery systems such as liposomes and emulsions that are well-known in the art, and a sustained-release system, such as semi-permeable matrices of solid polymers containing the therapeutic agent, may be employed. Various sustained-release materials have been established and are well-known to one skilled in the art. Further, the composition of the present invention can be administered alone or together with another therapy conventionally used for the treatment of tumor, such as surgical operation, hormone therapy, chemotherapy, or biological agents.

The quantity to be administered and timing may vary within a range depending on the formulation, the route of administration, and the tissue or subject to be treated, e.g., the patient's age, body weight, overall health, and other factors. The dosage of protein or nucleic acid of the present invention preferably will be in the range of about 0.01 ug/kg to about 10 g/kg of patient weight, preferably 0.01 mg/kg to 100 mg/kg.

When using the pharmaceutical composition of the invention as a gene therapeutic agent, the pharmaceutical composition may be administered directly by injection or by administering a vector integrated with the nucleic acid. For the nucleic acid molecule, the amount administered depends on the properties of the expression vector, the tissue to be treated, and the like. For viral vectors, the dose of the recombinant virus containing such viral vectors will typically be in the range of about $10^3$-about $10^{12}$ pfu/kg per kg of body weight.

The expression level of SISP-1 gene in normal tissues is high while that in tumor cells is low. Therefore, it is possible to estimate that the possibility of the tumor development or tumor existence in a subject is high in case the expression level of SISP-1 in the subject is lower than that in a normal.

Gene expression may be measured in a sample directly, for example, by conventional Southern blotting, Northern blotting to quantitate the transcription of mRNA (Thomas, Proc. Natl. Acad. Sci. USA, 77:5201 5205 (1980)), dot blotting (DNA analysis), or in situ hybridization, using an appropriately labeled probe, based on the sequences of SISP-1. Alternatively, antibodies may be employed that can recognize specific duplexes, including DNA duplexes, RNA duplexes, and DNA-RNA hybrid duplexes or DNA-protein duplexes.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence SISP-1 polypeptide or against a synthetic peptide based on the DNA sequences of SISP-1 gene.

The present invention provides a method for estimating the possibility of the tumor development in a subject or for diagnosing a tumor, comprising assaying a sample of the subject for the expression of SISP-1 protein or the induction of SISP-1 mRNA, wherein SISP-1 protein or SISP-1 mRNA detected below normal in the sample is indicative of either high possibility of the tumor development in the subject or the tumor existence in the subject.

The present invention also provides a kit for estimating the possibility of the tumor development in a subject or for diagnosing a tumor, comprising (a) at least one agent reactive with SISP-1 protein or SISP-1 mRNA; and (b) reagents suitable for detecting the expression of SISP-1 protein or inducing of SISP-1 mRNA. Said at least one agent reactive with SISP-1 protein can be an antibody specific to SISP-1 protein or its fragment. Alternatively, said at least one agent reactive with SISP-1 mRNA can be a complement to SISP-1 mRNA or its fragment. Further, said at least one agent is labeled with a detectable marker.

In addition, the present invention provides a method for monitoring the efficacy of therapy to treat tumor in a subject, who has undergone or is undergoing treatment for tumor, comprising assaying a sample of the subject for the expression of SISP-1 protein or the induction of SISP-1 mRNA, wherein the detection of normal or elevated SISP-1 protein or SISP-1 mRNA in the sample is indicative of successful therapy to treat tumor and the detection of decreased SISP-1 protein or SISP-1 mRNA below normal in the sample is indicative of a need to continue therapy to treat tumor.

The present invention provides several methods for screening a compound for an apoptosis-regulating agent.

One method for screening a compound for an apoptosis-regulating agent comprises the step of: (a) culturing a cell containing the nucleic acid molecule of this invention and measuring the expression level of said nucleic acid; (b) separately from step (a), culturing a sample containing a candidate compound with a cell containing the nucleic acid of this invention under the same condition as step (a) and measuring the expression level of said nucleic acid; and (c) selecting a compound in the sample capable of the higher or lower expression level of said nucleic acid measured in step (b) than that in step (a). Said cell containing the nucleic acid molecule of this invention can be a cell containing a vector with the structure in which the nucleic acid molecule of this invention is operably linked to a reporter gene and said measurement can refers to the expression level of the reporter gene.

Another method for screening a compound for an apoptosis-regulating agent, comprises the step of: (a) contacting a sample containing a candidate compound with the polypeptide of this invention or the nucleic acid molecule of this invention; (b) detecting the binding ability of the candidate compound in the sample to said polypeptide or nucleic acid molecule; and (c) selecting a compound having the binding ability to said protein or nucleic acid molecule.

Another method for screening a compound for an apoptosis-regulating agent, comprises the step of: (a) preparing an in vitro system comprising tumor cells which is sensitive to the apoptosis by either the polypeptide of the present invention or the nucleic acid molecule of the present invention; (b) contacting both a sample containing a candidate compound and either the polypeptide of the present invention or the nucleic acid molecule of the present invention with the in vitro system; (c) determining the apoptosis level of said tumor cells; (d) comparing the apoptosis level of said tumor cells which are treated by both the candidate sample and either the polypeptide of the present invention or the nucleic acid molecule of the present invention, with the apoptosis level of the tumor cells which are treated only by either the polypeptide of the present invention or the nucleic acid molecule of the present invention; and (e) selecting a compound capable of the higher or lower apoptosis level of the tumor cells than that measured using only either the polypeptide of the present invention or the nucleic acid molecule of the present invention. The apoptosis-regulating agent can be a tumor treatment agent.

In addition, the present invention provides a kit for screening a compound for an apoptosis-regulating agent, comprising (a) tumor cells which are sensitive to the apoptosis by either the polypeptide of the present invention or the nucleic acid molecule of the present invention; (b) the polypeptide of the present invention or the nucleic acid molecule of the present invention and (c) reagents suitable for detecting the apoptosis level of the tumor cells.

The present invention further provides a kit for screening a compound for an apoptosis-regulating agent, comprising (a) a cell containing a nucleic acid molecule of the present invention and (b) reagents suitable for detecting the expression level of the nucleic acid. The kit can comprise (a) a cell containing a vector with the structure in which the nucleic acid molecule of the present invention is operably linked to a reporter gene and (b) reagents suitable for detecting the expression level of the reporter gene. Said reagents suitable for detecting the expression level are labeled with a detectable marker. Said reagents suitable for detecting the expression level can be an antibody specific to polypeptide of the present invention, fragments thereof, derivatives thereof or homologues thereof. Alternatively, said reagents suitable for detecting the expression level can be a complement to SISP-1 mRNA or its fragments.

The following examples illustrate the present invention in further detail. However, it is understood that the present invention is not limited by these examples.

EXAMPLE 1

Identification of SISP-1

SISP-1 was isolated as a tumor suppressor p53 responsive gene by using a DNA chip expression array to compare genes expressed in the presence or absence of p53. Affymetrix GeneChips were used for hybridization. Two sets of human expression arrays (human genome U95A, Affymetrix Inc.) were hybridized with fluorescently labeled cRNA probes derived from total RNAs extracted from EJ-p53 cells grown in the presence or absence of tetracycline for 1 and 2 days. Among upregulated genes detected, the transcript for SISP-1 was found to increase in response to p53 induction.

EJ-p53 cells were prepared as follows: pETH was constructed by ligating the DNA fragment (XhoI-HindIII) from pUHD 15-1 (obtained from H. Bujard, ZMBH, Heidelberg), which contains the tTA expression cassette, into the expression vector pSV40-Hyg, which contains the Hyg$^r$ gene. pTet-53 was constructed by subcloning wild-type (wt) p53 cDNA down-stream of the tet-regulated promoter into pUHD10-3 (obtained from H. Bujard) which contains neo$^r$. EJ cells were serially transfected with each plasmid using the calcium phosphate method. Transfectants were selected in the presence of hygromycin (100 μg/ml) and geneticin (750 μg/ml). Stable EJ-ETH clones were tested for transactivator activity using a standard chloramphenicol acetyltransferase (CAT) assay. One clone, EJ-ETH-9, which showed the highest CAT activity, was subsequently transfected with pTet-p53. Individual clones of stable double transfectants, named EJ-p53, were selected for further analysis.

To identify complete mRNA sequences encoding a full SISP-1 protein after the initial hybridization, the hybridized sequences from the GeneChips were then used to further search for a putative complete open reading frame (orf). Based on the orf, the inventor found EST sequences in the public database. Several EST sequences were used to obtain a full SISP-1 coding sequences and any missing sequences were obtained by resequencing the EST sequences. By combining the known EST sequences, resequenced unknown EST sequences and sequences from the genomic sequences from the public databases, the inventor identified the location on the genome (AL 731541.6; Human DNA sequence from clone RP11-472K8 on chromosome 10) and finally deduced a final SISP-1. The inventor deduced exons and introns deduced based on the combined putative SISP-1 mRNA on the genome sequence.

SISP-1 cDNA (SEQ ID NO: 1) encodes a 311-amino acid protein (FIG. 2A; SEQ ID NO: 2), with a predicted molecular mass of ~35 kDa. Examination of the amino acid sequence identified a high sequence similarity in the N-terminal region (amino acid 29 to 148) of the predicted SISP-1 sequence with the 1 G-like/death domain motif (FIG. 2B) and a signal peptide sequence at N-terminus. Also, a putative transmembrane sequence exist between amino acid 194 to 216.

To search for potential p53 binding sites from the promoter region of SISP-1, the MARTINSPECTOR computer program was initially used (Quandt, K. , Frech, K. , Karas, H., Wingender, E. & Werner, T. (1995) *Nucleic Acids Res.* 23, 4878-4884). After identifying potential p53 binding consensus motif 5'-RRRCWWGYYY-3' (R =G or A, W =T or A, Y =C or T) (el-Deiry WS, Kern SE, Pietenpol JA, Kinzler KW, Vogelstein B, Definition of a consensus binding site for p53. *Nat Genet* 1992;1:459) within the promoter region, this result was manually confirmed. The sequence of p53 binding consensus motif is shown as SEQ ID NO: 10. SISP-1 genomic sequence has four potential sites in the promoter region, which revealed an 85% or greater match to the consensus p53-binding sequence (FIG. 3, FIG. 4B). However, only one p53 binding site close the transcription site, that is 475bp upstream from the transcription start site, was found to be active in a functional assay.

EXAMPLE 2

SISP-1 Induction in Response to Tumor Suppressor p53 or Genotoxic Stress

The inventor of the present invention performed RNA blotting (Northern blot analysis) to confirm SISP-1 induction in response to p53 or genotoxic drugs.

IMR90 normal diploid fibroblasts (Obtained from ATCC) were cultured in Dulbecco's modified Eagle's medium (DMEM, Invitrogen)) containing 10% fetal bovine serum (FBS, Hyclone), 100 units/ml of penicillin, and 100 µg/ml of streptomycin at 37° C. For drug treatment, IMR90 cells were grown with or without therapeutic agent etoposide (50 µM) or CPT (camptothecin, 600 nM, Sigma) for 24-48 hours. Then, total RNA was extracted, denatured, electrophoresed through a 1% agarose-formaldehyde gel and transferred to a nylon membrane. Hybridization was performed with $^{32}$P-labeled probes, SISP1, p21 or 36B4 (a loading control) prepared by the randomly primed DNA labeling method. EJ-p53 cells were cultured in the presence or absence of tetracycline (1 µg/ml, Sigma). Total RNA was extracted from EJ-p53 cells for the indicated times (12-48 hours). Northern blot analysis (RNA blotting analysis) was also performed with same probes.

FIG. 4A demonstrates the result of Northern blot analysis. The expression of SISP-1 mRNA was induced in normal cells (IMR90) by the treatment of chemotherapeutic agents etoposide and CPT (camptothecin) (FIG. 4A, left). The expression of SISP-1 mRNA was also induced in EJ-p53 cell in which p53 was expressed by removing tetracycline but not in EJ-p53 cell treated by tetracycline (FIG. 4A, right). The result confirms that SISP-1 is induced in responsive to genotoxic stress or p53.

<Stimulation of Transcriptional Activity of SISP-1 by p53>

To determine whether SISP-1 is a direct target for p53, the inventor searched for potential p53 binding site(s) within its genomic sequence. Four potential sites were identified in the promoter region, which revealed an 85% or greater match to the consensus p53-binding sequence.

Then, the inventor evaluated the p53-dependent transcriptional activity of the SISP-1 promoter region containing 2 kb genomic fragment using a heterologous reporter assay. The inventor made a deletion of the SISP-1 promoter sequence linked to the upstream of the luciferase reporter gene of the pGL3-basic vector and performed reporter assay.

The reporter plasmid pGL3-SISP-1, containing the putative p53-recognition sequences in the SISP-1 promoter, was co-transfected into Saos-2 (obtained from ATCC) cells with either wild-type p53 or mutant p53 (V143A) expression constructs. pGL3-SISP1 was constructed by subcloning the promoter region (including untranslated region) of SISP-1 into pGL3 promoter vector (obtained from Promega; Cat. Number E1761) through inserting PCR product corresponding to the promoter region of SISP1 into the KpnI/XhoI sites of pGL3. PRL-TK (Renilla plasmid, Promega) was also co-transfected for normalization of the luciferase signal. Cells were harvested 48 hours after transfection and the assay was performed using the dual-luciferase reporter assay system (Promega). The p21 promoter-luciferase construct was used for a positive control.

The inventor made a deletion of the SISP-1 promoter sequence linked to the upstream of the luciferase reporter gene of the pGL3-basic vector and performed reporter assays (FIG. 4B). Co-transfection of the luciferase construct of the SISP-1 promoter containing the four potential p53-binding sites (p53-BS) along with a wt-p53 expression plasmid into Saos2 cells lacking wt-p53 increased luciferase activity significantly, while co-transfection with a control vector pcDNA3 vector failed to do so (FIG. 4B). Deletion of a 582 bp fragment containing a putative p53-binding site in the SISP-1 promoter maintained the promoter activity in response to wt-p53 (FIG. 4B, S1). These results suggest that SISP-1 is a transcriptional target for wt-p53.

EXAMPLE 3

The Location/Distribution of SISP-1

To determine the location/distribution of SISP-1, a carboxyl or N-terminally myc- or HA-tagged construct was expressed in 293 kidney cells, and total cell lysates and media were collected and subjected to western blot analysis. SISP-1 expression plasmid containing HA (hemaglutinin) epitope tag at C-terminus or N-terminus was transfected into 293 human kidney epithelial cells (purchased from ATCC). The myc-tagged SISP-1 (C-terminus) expression plasmid was also transfected into 293 cells. Thirty-six hours after transfection, cells were harvested on ice in lysis buffer (20 mM Tris [pH7.4]. 5 mM EDTA, 10 mM $Na_4P_2O_7$, 100 mM NaF, 2 mM $Na_3VO_4$, 1% NP-40, 1 µM PMSF, 10 µg/ml aprotinin, and 10 µg/ml leupeptin). Cell culture medium was also collected for Western blot (protein) analysis. Equal amounts of total cellular proteins per sample were subjected to SDS-PAGE and transferred to a nitrocellulose membrane. Antibodies for Western blotting included anti-HA tag, anti-myc tag and anti-beta-actin (Sigma). Cell culture medium was cleared by the ProteoSeek Albumin/IgG removal kit (BioRad) prior to SDS-PAGE.

FIG. 5 is the result of the Western blot (protein) analysis of cell lysate and cell culture medium. The N-terminally cloned HA-SISP-1 showed no expression in cells as well as in culture media. However, ectopically expressed C-terminally HA-fused SISP-1 was strongly appeared in the cell lysates and culture media. Such an expression pattern of the SISP-HA or SISP-myc strongly suggests SISP-1 as a likely secreted protein.

EXAMPLE 4

Apoptotic Effect of SISP-1 on Human Hematopoietic Tumor Cell Line, Jurkat

Figure 6:
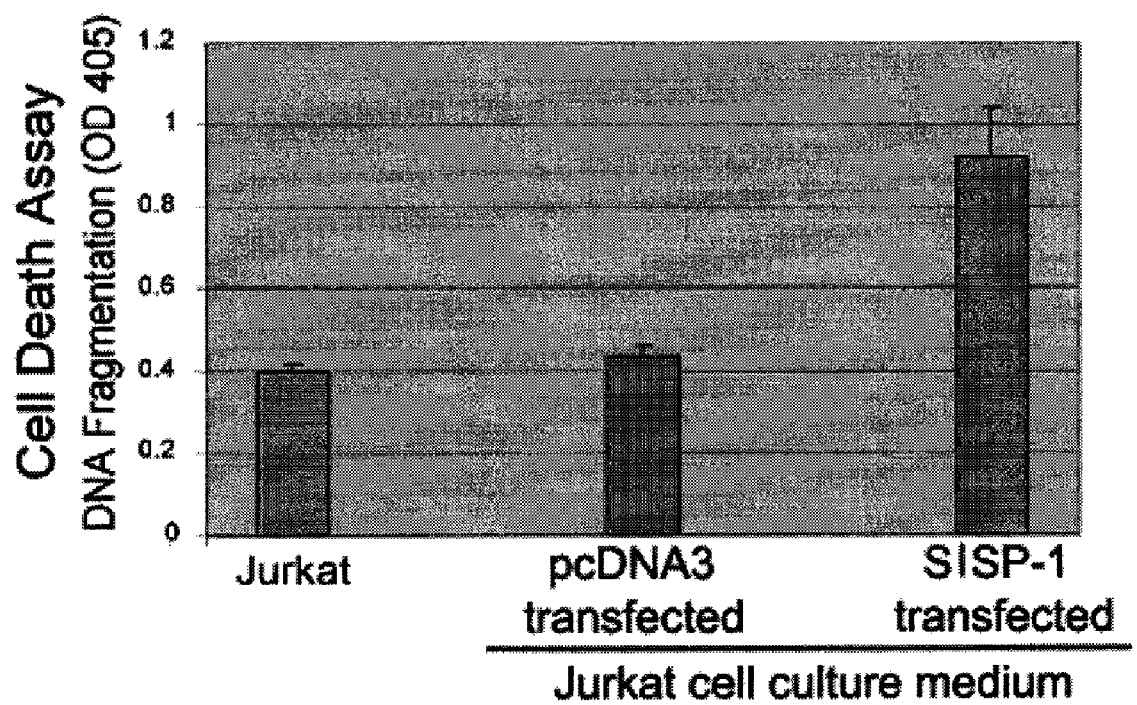
FIG. 6 illustrates the result of Cell Death Elisa showing that SISP-1 containing conditional media kill human leukemia cells (Jurkat cell lines).

SISP-1 was identified as a p53 induced gene and is implicated in the p53-mediated apoptosis. Moreover, the SISP-1 protein has a potential death domain. These observations raise the possibility that SISP-1 might have a role in the cell death process. Thus, the inventor of the present invention first examined whether ectopic expression of SISP-1 had any affect on the cell growth in the human hematopoitic tumor cell line, Jurkat (obtained form ATCC). SISP-1 expression plasmid was constructed by subcloning the orf region (from "atg" to "tag") of SISP-1 into pcDNA3.1(+) through inserting the PCR product corresponding to the orf region into the NheI/XbaI sites of pcDNA3.1 (+). The SISP-1 expression plasmid or control vector (pcDNA3.1(+); obtained from Invitrogen, V790-20) alone was transfected into Jurkat cells. Cell cultures were centrifuged to collect the medium that was used for cell death assays. The medium from either vector control transfected cells or SISP-1 transfected cells was transferred to the parental Jurkat cells Twenty-four hours later, we analyzed for cell death potential of the SISP-1 containing medium by using CELL Death Elisa (Roche). The inventor observed that media from SISP-1 transfected Jurkat cells caused significant apoptosis compared to that of control vector transfected Jurkat cells (FIG. 6).

EXAMPLE 5

SISP-1 Activates Pro-apoptotic Markers and Downregulates a Pro-survival Protein

Figure 7:
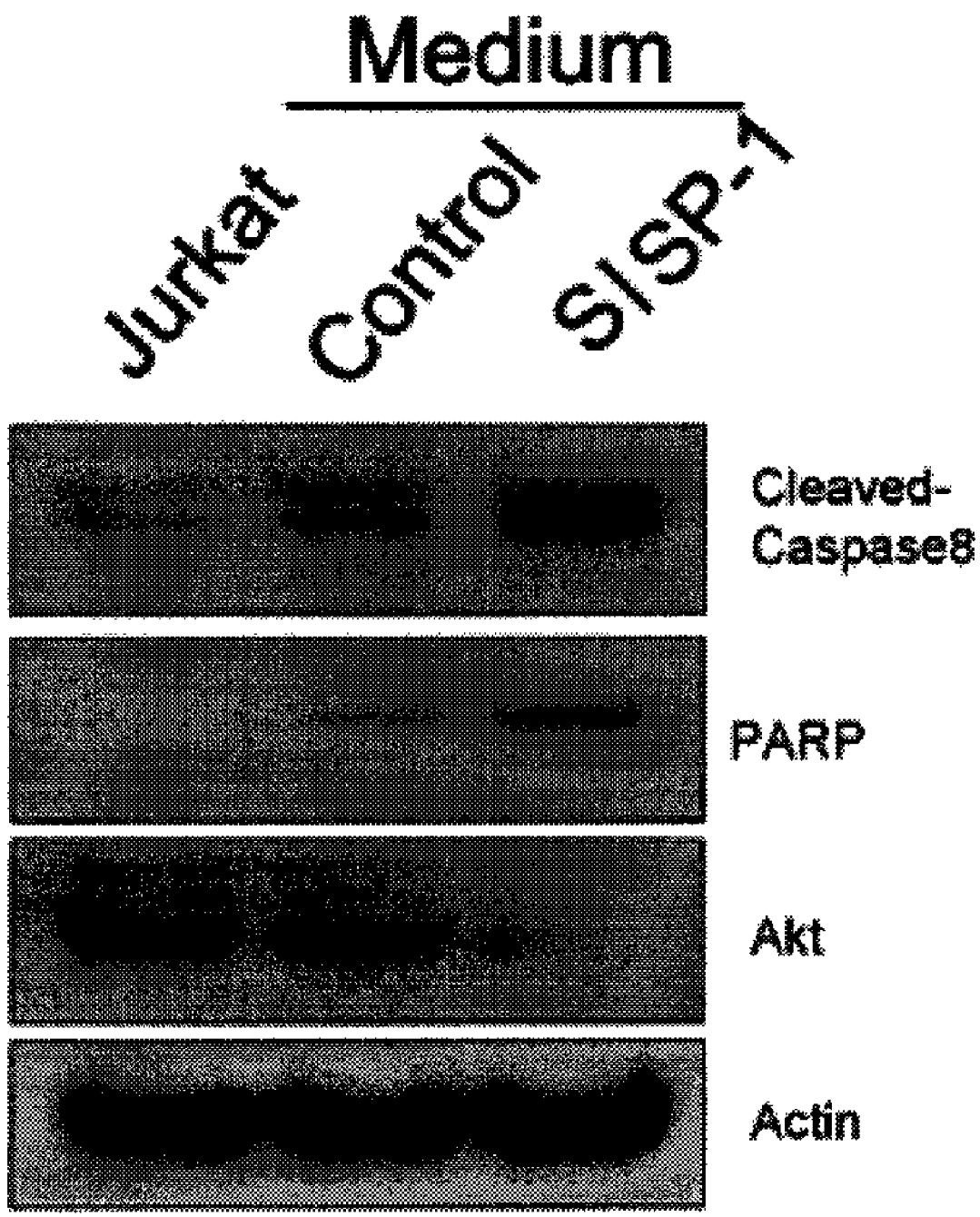
FIG. 7 demonstrates the result of Western blotting analysis showing that SISP-1 activates pro-apoptotic markers, including caspase-8 and PARP, and down-regulates a pro-survival protein AKT.

Cell lysates were isolated from SISP-1 (pcDNA3.1-SISP-1) transfected cells as well as control vector (pcDNA3.1) transfected or parental Jurkat cells. Western blotting was performed using antibodies against caspase-8 (NEB), PARP (Santa Cruz), AKT (NEB) and beta-actin (Sigma). SISP-1 transfected Jurkat cells increased proapoptotic markers including an active form of caspase-8 and PARP cleavage while expression of a survival indicator AKT was significantly decreased in SISP-1 transfected Jurkat cells (FIG. 7).

EXAMPLE 6

Adenovirus-mediated SISP-1 Overexpression Induces Apoptosis and Sensitizes Genotoxic Drug Etoposide-induced Apoptosis Next, the inventor investigated the apoptotic effects of SISP-1 expression in human colon cancer cells and breast carcinoma cells by using adenovirus expressing SISP-1. Adenovirus-mediated SISP-1 overexpression induces apoptosis and sensitizes genotoxic drug etoposide-induced apoptosis in human colon carcinoma cells (HCT116, purchased from ATCC) and human breast cancer cells (MDAMB435, purchased ATCC). Adenoviruses expressing HA-tagged SISP-1 (Ad-SISP-1) or GFP (Ad-GFP as a control) were generated, amplified and titrated. HCT 116 colon carcinoma cells and MDAMB435 breast cancer cells were grown to 50-70% confluency and infected with recombinant adenovirus at multiplicity of infection (MOI) of 15-30. 12 hour post infection, cells were treated with etoposide (ETO, 30 µM, Sigma) for 24 hours. Then, cell death rate was measured by DNA fragmentation assay (Cell death Elisa kit, Roche).

Figure 8:
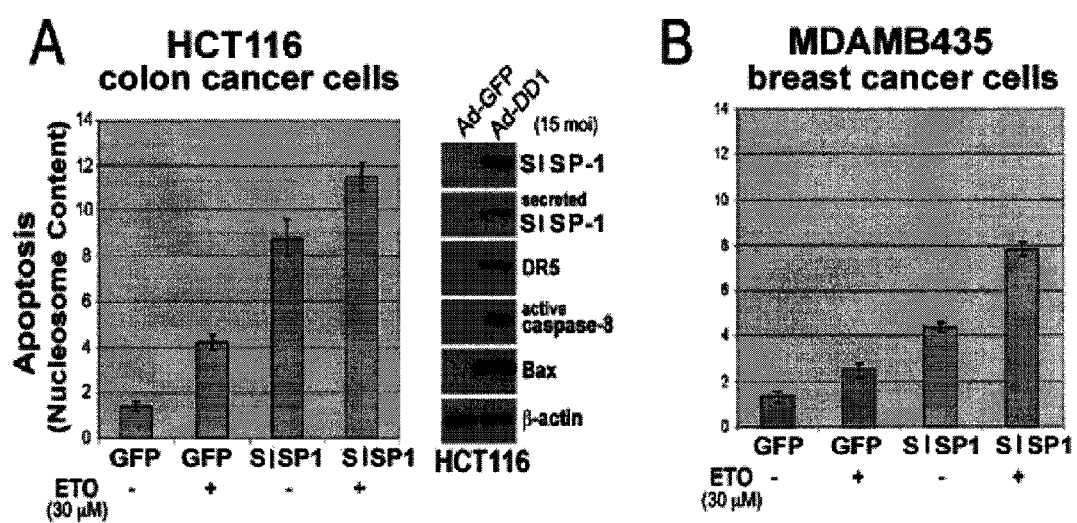
FIGS. 8A and 8B show that adenovirus-mediated SISP-1 overexpression induces apoptosis and sensitizes genotoxic drug ETO (etoposide)-induced apoptosis in human colon carcinoma cells (HCT116.

Ectopic SISP-1 overexpression in these cells markedly increased cell death compared to control adenovirus expressing cells (FIGS. 8A&B). Moreover, a chemotherapeutic agent etoposide selectively sensitized SISP-1 overexpressing cancer cells.

EXAMPLE 7

SISP-1 Significantly Sensitizes a Chemo-drug-induced Apoptosis

The present inventor further examined whether SISP-1 could also sensitize U2OS cells that is known to be quite resistant to chemo-drugs. Tetracycline-regulated inducible expression (Clontech) of SISP-1 significantly sensitizes a chemodrug (etoposide)-induced apoptosis in chemo-resistant osteosarcoma cells (U2OS) and human bladder carcinoma cells (EJ).

U2OS-tet-on-SISP-1 cells were generated by isolating tetracycline regulated stable-clones expressing SISP-1 upon tetracycline addition (doxycycline, Sigma). U2OS-SISP-1 cells were cultured in the presence or absence of doxycycline (1 µg/ml) for 24 hours. Cells were then exposed to low concentration of etoposide at 15 µM and apoptosis rates were measured by cell death assays including Cell-Death Elisa (Roche) and survival assay (crystal-violet staining).

Figure 9:
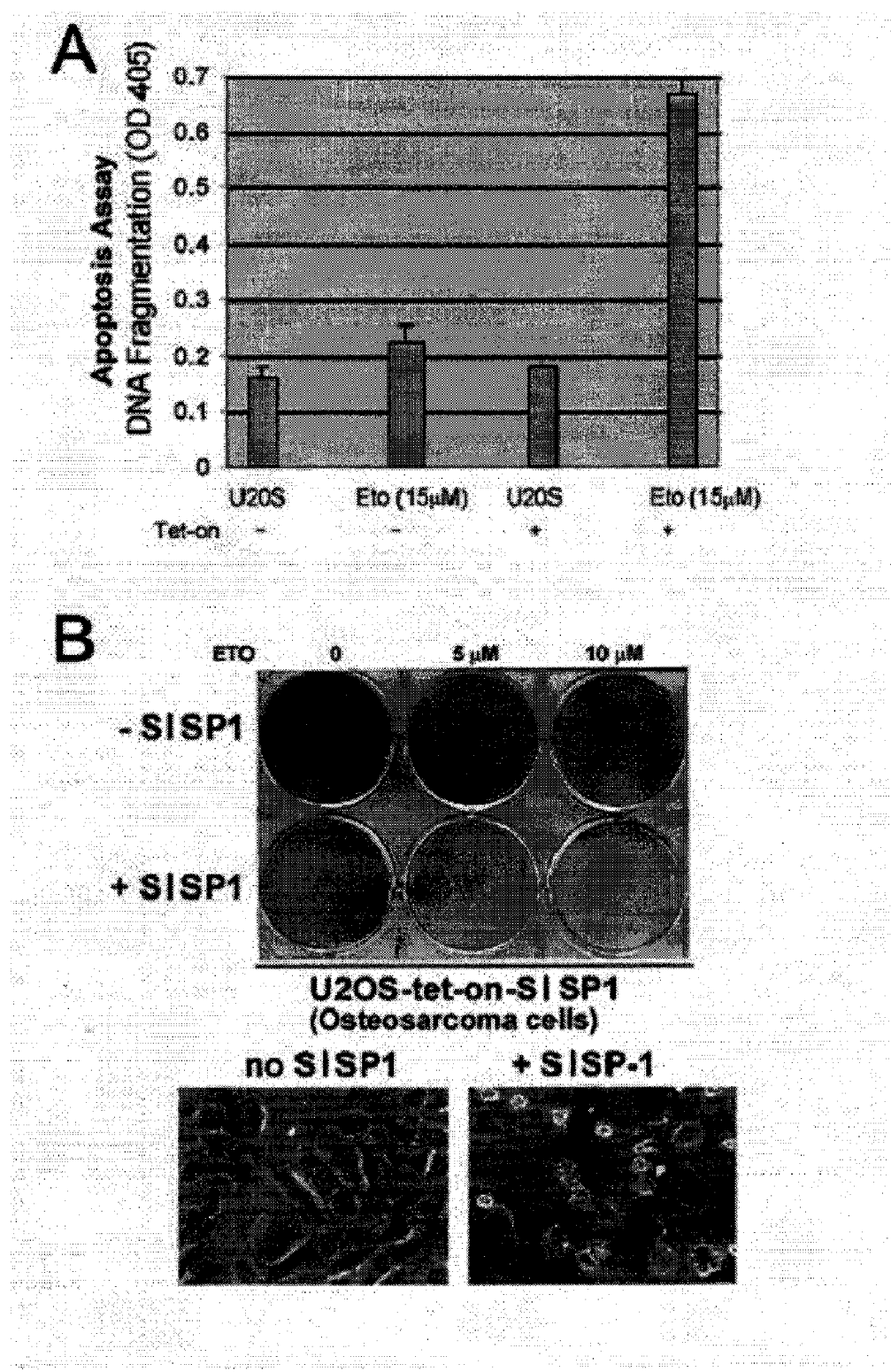
FIGS. 9A and 9B demonstrate that tetracycline-regulated inducible expression of SISP-1 significantly sensitizes a chemodrug (etoposide)-induced apoptosis in chemo-resistant osteosarcoma cells (U2OS). U2OS-tet-on-SISP-1 cells were generated by isolating tetracycline regulated stable-clones expressing SISP-1 upon tetracycline addition. U20S-SISP-1 cells were cultured in the presence or absence of doxycycline. Cells were then exposed to low concentration of etoposide and apoptosis rates were measured by cell death assays including Cell-Death Elisa and survival assay (crystal-violet staining).
Figure 10:
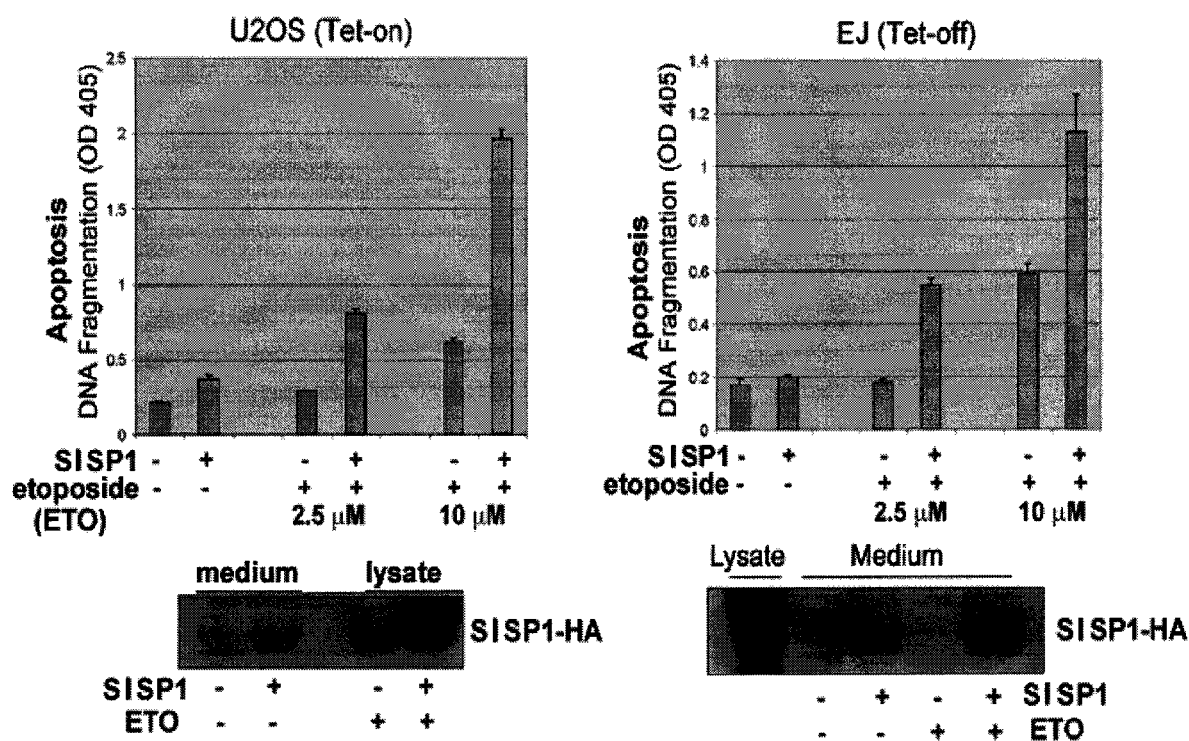
FIG. 10 demonstrates that tetracycline-regulated inducible expression of SISP-1 significantly sensitizes a chemodrug (etoposide)-induced apoptosis in chemo-resistant osteosarcoma cells (U2OS) and human bladder carcinoma cells (EJ).

As shown in FIG. 9A, an inducible SISP-1 expression by tetracycline-regulated expression system significantly enhanced etoposide-mediated apoptosis (>3-folds) whereas SISP-1 or etoposide treatment itself did not induce cell death in U2OS cells. The SISP-1-mediated sensitizing effect was also confirmed by survival assay in lower concentration of etoposide (5 µM and 10 µM) (FIG. 9B). The inventor re-evaluated this effect in a rapidly growing human bladder carcinoma cell line, EJ, since SISP-1 may be used a strong candidate as a new sensitizing molecule that improves the therapeutic efficacy and minimizes the toxicity of chemo-drugs. To further confirm the sensitizing effects of SISP-1 expression in a combination of chemo-drugs, we generated tumor cells containing the tetracycline-regulated inducible expression of SISP-1 using U2OS and EJ lines. Upon SISP-1 induction, treatment with 2.5 µM to 10 µM etoposide very effectively enhanced etoposide-induced cell death (FIG. 10). However, etoposide itself induced a limited cell death over 48 hours.

EXAMPLE 8

Normal Diploid Fibroblasts are Resistant to SISP-1 Induced Apoptosis

The inventor next examined whether SISP-1 induces cell death in normal or normal like cells. IMR90 cells were infected with a recombinant adenovirus expressing GFP (control, Ad-GFP) or SISP-1 (Ad-SISP-1) for 24 hours. Apoptotic cell populations in the IMR90 cells were measured using the cell death detection ELISA. In all cases, error bars indicate ±SD of three independent experiments with each sample in duplicate.

Figure 11:
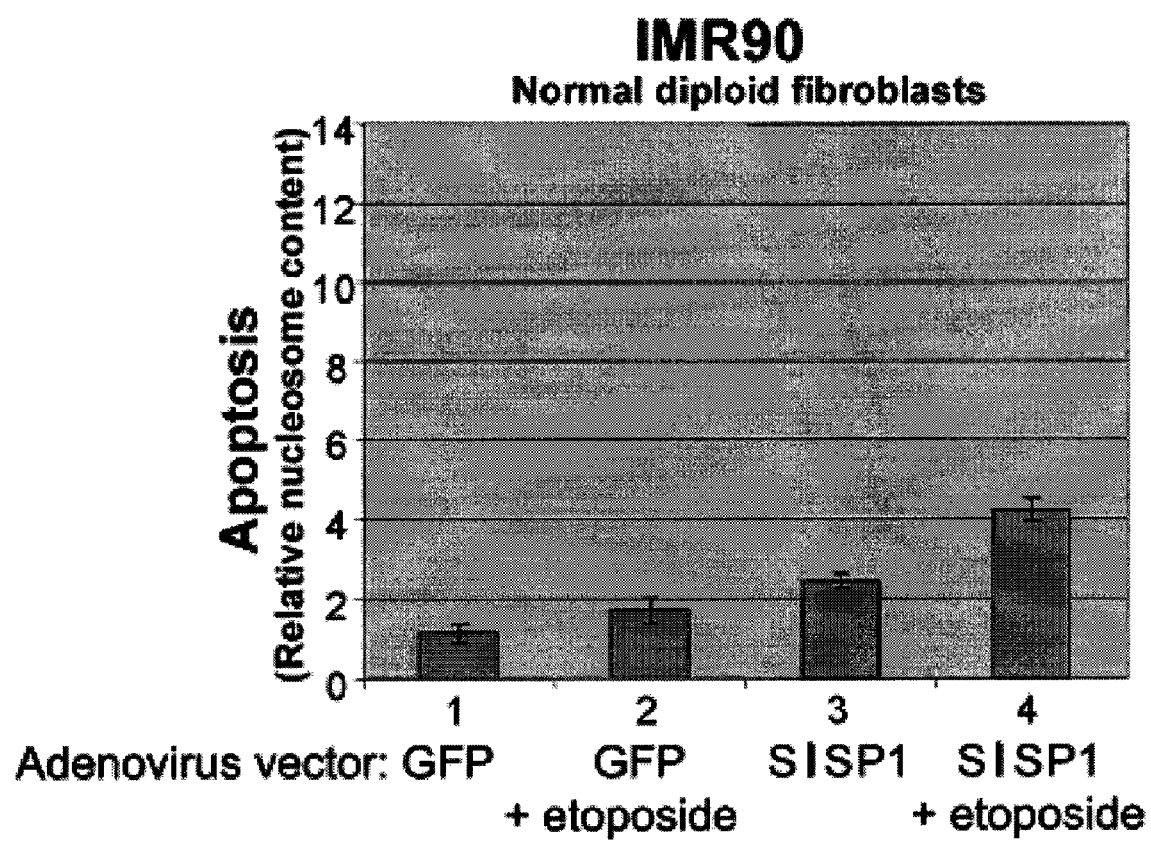
FIG. 11 shows the result from Cell-Death detection ELISA demonstrating that normal diploid fibroblasts (IMR90) are resistant to SISP-1 induced apoptosis.

Unlike the effect of SISP-1 on cancer cells, adenovirus-mediated overexpression of SISP-1 did not induce significant cell death (FIG. 11), suggesting that this normal fibroblast cells are resistant to the apoptotic effects of SISP-1.

EXAMPLE 9

SISP-1 Expression in Human Normal Tissues and Human Cancer Cells

Since SISP-1 expression has cell-death inducing effect on human cancer cells but induced the limited cell death in normal cells, the present inventor evaluated the pattern of SISP-1 expression in normal human tissues.

<Northern Blot Analysis>

Total RNA was extracted using Qiagen RNeasy kit with QIAshredder according to the manufacturer's protocol (Qiagen). Samples were quantified by their absorbance at 260 nm, denatured and equal amounts electrophoresed through 1% agarose gel by the formaldehyde denaturation method. RNA was transferred to a nylon membrane (Bio-Rad) UV-crosslinked using a Stratagene UV-crosslinker, then baked at 80° C. for 1 hour. Hybridization was performed with $^{32}$P-labeled probes including SISP-1 (DD1) and 36B4 (a loading control) prepared by the randomly primed DNA labeling method (Invitrogen). After washing with 2-0.5% SSC/0.1% SDS, the blots were autoradiographed using Kodak's BioMax M S film.

A shown in FIG. 12A, SISP-1 expression was universally expressed in most of organs including lung, placenta, small intestine and kidney, spleen, but most dominantly in blood leukocyte and slightly lesser in heart and placenta, suggesting that SISP-1 is required for maintaining normal cell function and may not be toxic to normal cells in the aspect of therapeutics. The present inventor also found that SISP-1 expression was significantly reduced in human breast cancer cells when compared with normal mammary epithelial cells (FIG. 12B).

I claim:

1. An isolated nucleic acid molecule selected form the group consisting of:
   (a) a nucleic acid consisting of the nucleotide sequence of SEQ ID NO: 1, or a full-length complement thereof;
   (b) a nucleic acid consisting of the nucleotide sequence of SEQ ID NO: 3 and SEQ ID NO: 4, or a full-length complement thereof; and
   (c) a nucleic acid consisting of the nucleotide sequence of SEQ ID NO:6, or a full-length complement thereof.

2. A recombinant expression vector comprising the nucleic acid molecule of claim 1.

3. A viral vector comprising the nucleic acid molecule of claim 1.

4. A non-viral vector comprising the nucleic acid molecule of claim 1.

5. A host cell transformed with the nucleic acid molecule of claim 1.

* * * * *